United States Patent
Friedman

(10) Patent No.: US 12,017,091 B2
(45) Date of Patent: Jun. 25, 2024

(54) IONIZING-RADIATION BEAMLINE MONITORING SYSTEM

(71) Applicant: Integrated Sensors, LLC, Palm Beach Gardens, FL (US)

(72) Inventor: Peter S. Friedman, Palm Beach Gardens, FL (US)

(73) Assignee: Integrated Sensors, LLC, Palm Beach Gardens, FL (US)

( * ) Notice: Subject to any disclaimer, the term of this patent is extended or adjusted under 35 U.S.C. 154(b) by 0 days.

(21) Appl. No.: 18/462,606

(22) Filed: Sep. 7, 2023

(65) Prior Publication Data

US 2023/0414969 A1 Dec. 28, 2023

Related U.S. Application Data

(63) Continuation of application No. 17/451,517, filed on Oct. 20, 2021, now Pat. No. 11,779,778, which is a
(Continued)

(51) Int. Cl.
*A61N 5/10* (2006.01)
*A61N 5/00* (2006.01)
(Continued)

(52) U.S. Cl.
CPC ............. *A61N 5/1067* (2013.01); *A61N 5/00* (2013.01); *A61N 5/1045* (2013.01);
(Continued)

(58) Field of Classification Search
None
See application file for complete search history.

(56) References Cited

U.S. PATENT DOCUMENTS

| | | | |
|---|---|---|---|
| 4,257,688 A | * | 3/1981 | Matsumura ............... A61B 3/14 351/210 |
| 4,345,153 A | | 8/1982 | Yin |

(Continued)

FOREIGN PATENT DOCUMENTS

| | | |
|---|---|---|
| CN | 107589440 A | 1/2018 |
| CN | 107589441 A | 1/2018 |

(Continued)

OTHER PUBLICATIONS

Almurayshid et al., "Quality assurance in proton beam therapy using a plastic scintillator and a commercially available digital camera", Radition Oncology Physics, Jun. 14, 2017, DOI: 10.1002/acm2.212143.

(Continued)

*Primary Examiner* — Hoon K Song
(74) *Attorney, Agent, or Firm* — Potomac Law Group, PLLC

(57) ABSTRACT

Embodiments are directed generally to an ionizing-radiation beamline monitoring system that includes a vacuum chamber structure with vacuum compatible flanges through which an incident ionizing-radiation beam enters the monitoring system. Embodiments further include at least one scintillator within the vacuum chamber structure that can be at least partially translated in the ionizing-radiation beam while oriented at an angle greater than 10 degrees to a normal of the incident ionizing-radiation beam, a machine vision camera coupled to a light-tight structure at atmospheric/ambient pressure that is attached to the vacuum chamber structure by a flange attached to a vacuum-tight viewport window with the camera and lens optical axis oriented at an angle of less than 80 degrees with respect to a normal of the scintillator, and at least one ultraviolet ("UV") illumination source facing the scintillator in the ionizing-radiation beam for monitoring a scintillator stability comprising scintillator radiation damage.

17 Claims, 33 Drawing Sheets

Related U.S. Application Data continuation of application No. 17/332,047, filed on May 27, 2021, now Pat. No. 11,154,728, which is a continuation of application No. 17/091,310, filed on Nov. 6, 2020, now Pat. No. 11,027,152, which is a continuation-in-part of application No. 16/811,471, filed on Mar. 6, 2020, now Pat. No. 10,828,513, which is a continuation-in-part of application No. 16/697,439, filed on Nov. 27, 2019, now abandoned, which is a continuation of application No. 16/529,200, filed on Aug. 1, 2019, now Pat. No. 10,525,285.

(60) Provisional application No. 62/859,952, filed on Jun. 11, 2019, provisional application No. 62/815,006, filed on Mar. 7, 2019, provisional application No. 62/714,937, filed on Aug. 6, 2018.

(51) Int. Cl.
  *G01T 1/40* (2006.01)
  *G01T 1/161* (2006.01)
  *G01T 1/29* (2006.01)

(52) U.S. Cl.
  CPC ......... *A61N 5/1048* (2013.01); *A61N 5/1049* (2013.01); *A61N 5/1064* (2013.01); *G01T 1/40* (2013.01); *A61N 2005/1059* (2013.01); *A61N 5/1077* (2013.01); *A61N 2005/1087* (2013.01); *G01T 1/1612* (2013.01); *G01T 1/29* (2013.01)

(56) References Cited

U.S. PATENT DOCUMENTS

| | | | |
|---|---|---|---|
| 5,668,371 | A | 9/1997 | Deasy et al. |
| 6,087,656 | A | 7/2000 | Kimmich et al. |
| 10,525,285 | B1 | 1/2020 | Friedman |
| 10,828,513 | B2 | 11/2020 | Friedman |
| 11,154,728 | B1 | 10/2021 | Friedman |
| 2004/0104349 | A1 | 6/2004 | Chugg |
| 2006/0262306 | A1* | 11/2006 | Dobschal ............... B82Y 40/00 356/337 |
| 2007/0181815 | A1 | 8/2007 | Ebstein |
| 2011/0204243 | A1 | 8/2011 | Bendahan et al. |
| 2011/0299659 | A1 | 12/2011 | Gray et al. |
| 2012/0018642 | A1 | 1/2012 | Fukuda et al. |
| 2013/0032713 | A1* | 2/2013 | Barbi ............... G01T 1/20188 250/311 |
| 2013/0313442 | A1 | 11/2013 | Wang et al. |
| 2014/0166890 | A1 | 6/2014 | Shimizu et al. |
| 2015/0071408 | A1 | 3/2015 | Ebstein |
| 2015/0099918 | A1 | 4/2015 | Takayanagi et al. |
| 2015/0273242 | A1 | 10/2015 | Balakin |
| 2016/0124094 | A1 | 5/2016 | Melcher et al. |
| 2018/0345042 | A1 | 12/2018 | Voronenko et al. |
| 2019/0022417 | A1 | 1/2019 | Heese |
| 2019/0069856 | A1 | 3/2019 | Achkire et al. |
| 2019/0285470 | A1 | 9/2019 | Bezel et al. |

FOREIGN PATENT DOCUMENTS

| | | |
|---|---|---|
| JP | 2016533505 A | 10/2016 |
| JP | 2018524043 A | 8/2018 |
| WO | 2020033250 A1 | 2/2020 |

OTHER PUBLICATIONS

Bilki et al., "Development of Radiation-Hard Scintillators and Wavelength-Shifting Fibers", International Conference on Technology and Instrumentation in Particle Physics, May 22-26, 2017.
Bilki et al., "Radiation damage studies of new intrinsically radiation-hard scintillators", 978-1-5090-1642-6/16, IEEE, 2016.
Daftari et al., "Scintillator-CCD camera system light output response to dosimetry parameters for proton beam range measurement," 2012, Nuclear Instruments and Methods in Physics Research A, vol. 686, pp. 7-14. (Year: 2012).
Eley et al., "Polyenergetic Data Acquisition Using a Video-Scintillator Detector for Scanned Proton Beams", International Journal of Particle Therapy, Published Mar. 14, 2017, pp. 392-397.
Fluhs et al., "Polyethylene Naphthalate Scintillator: A Novel Detector for the Dosimetry of Radioactive Ophthalmic Applicators", Ocular Oncology and Pathology, Basic Science Research, Published Jun. 6, 2015.
Fukumura et al., "Simple range measurement of therapeutic ion beams using visible rays in a bare plastic scintillator block," 1998, Nuclear Instruments and Methods in Physics Research A, vol. 416, pp. 148-151. (Year: 1998).
International Preliminary Report on Patentability issued in the corresponding International Application No. PCT/US2019/044832, mailed on Feb. 9, 2021.
Jeong et al., Feasibility study of a plastic scintillating plate-based treatment beam fluence monitoring system for use in pencil beam scanning proton therapy, published Dec. 2, 2019, Med. Phys. 47 (2), 2019 American Association of Physicists in Medicine, Feb. 2020, pp. 703-712.
Kharzheev, "Radiation Hardness of Scintillation Detectors Based on Organic Plastic Scintillators and Optical Fibers", Phys. Part. Nuclei. vol. 50, No. 1 (Jan. 2019) 42-76, https://doi.org/10.1134/S1063779619010027.
Kochnev et al., "Effect of ultraviolet radiation on polyethylene naphthalate films irradiated with high-energy heavy ions", Article in High Energy Chemistry, May 2017.
Nakamura et al., "Evidence of deep-blue photon emission at high efficiency by common plastic", Societa Italiana de Fisica, open access, epl, 95 (2011) 22001, doi: 10.1209/0295-5075/95/22001, Jul. 2011.
Onel et al., "New radiation-hard scintillators for FCC detectors", FCC week 2017, May 29-Jun. 2, 2017.
Robertson, "Volumertric scintillation dosimetry for scanned proton beams", Texas Medical Center Library, DigitalCommons@TMC, Aug. 2014.
Rydygier et al., "Studies of scintillator response to 60 MeV protons in a proton beam imaging system", accepted May 20, 2015, pp. 683-687.
Tamborini et al., "Development and characterization of a 2D scintillation detector for quality assurance in scanned carbon ion beams," 2016, Nuclear Instruments and Methods in Physics Research A, vol. 815, pp. 23-30. (Year: 2016).
Tiras et al., "Development of Radiation Hard Scintillators", Proceedings of Science, ICHEP2016, 1197, 38th International Conference on High Energy Physics, Aug. 3-10, 2016, Chicago, USA.

\* cited by examiner

Camera image (Fig. 6A) and analysis (Fig. 6B) of ~ 2.68 mm diameter proton beam irradiating 191 μm thick BoPEN film in a vacuum chamber. Pixel field-of-view is 38.2 μm x 38.2 μm and image exposure was 1 ms.

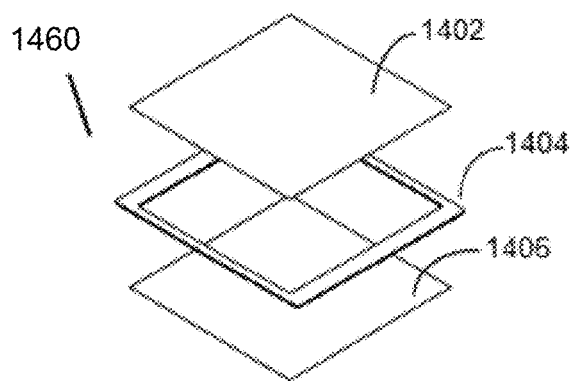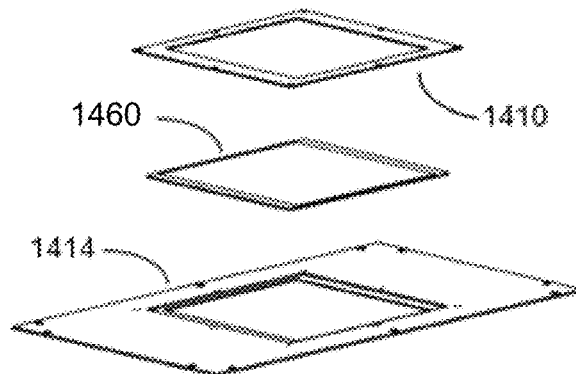
Fig. 14A  Fig. 14B
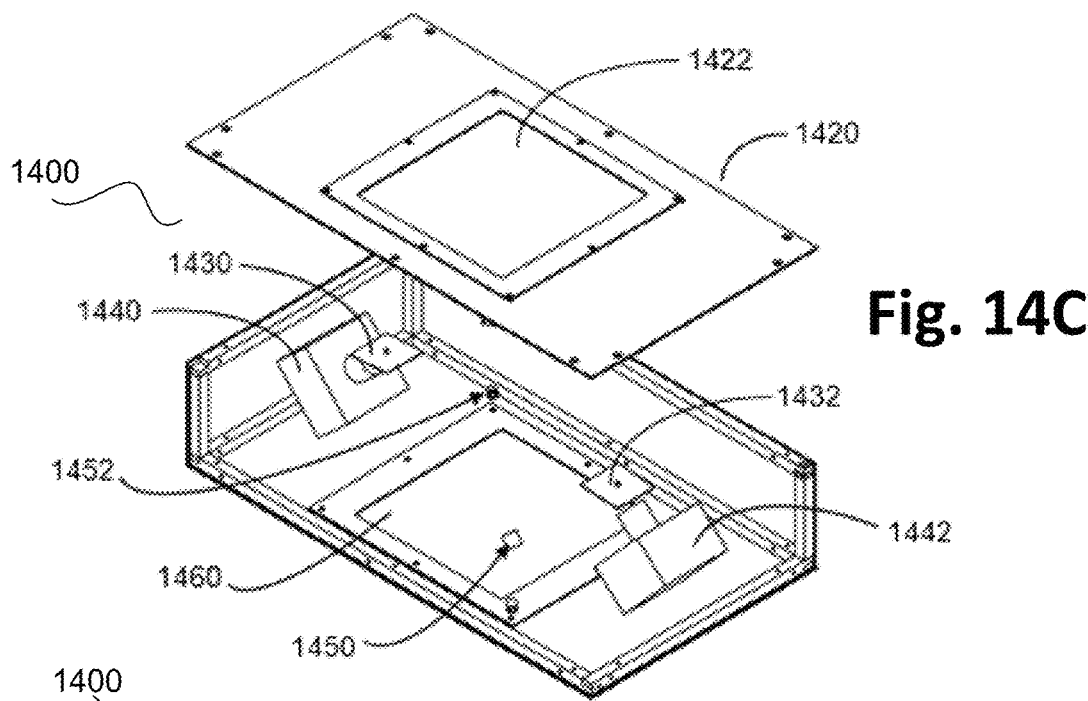
Fig. 14C
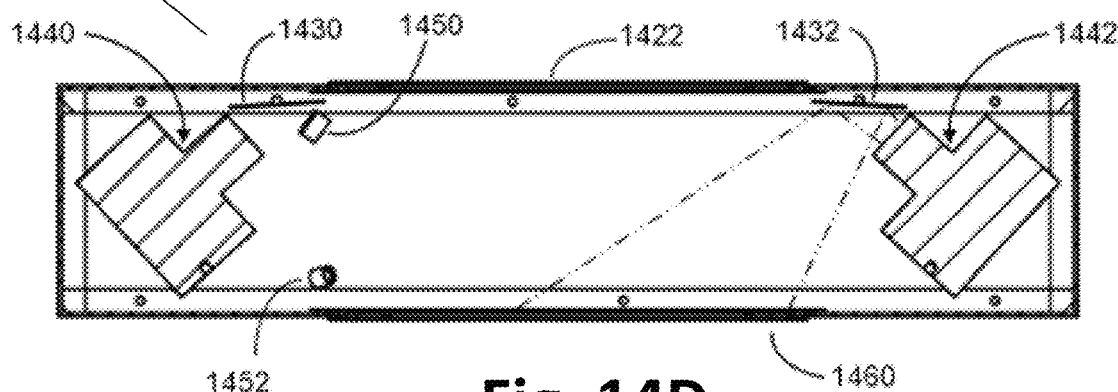
Fig. 14D

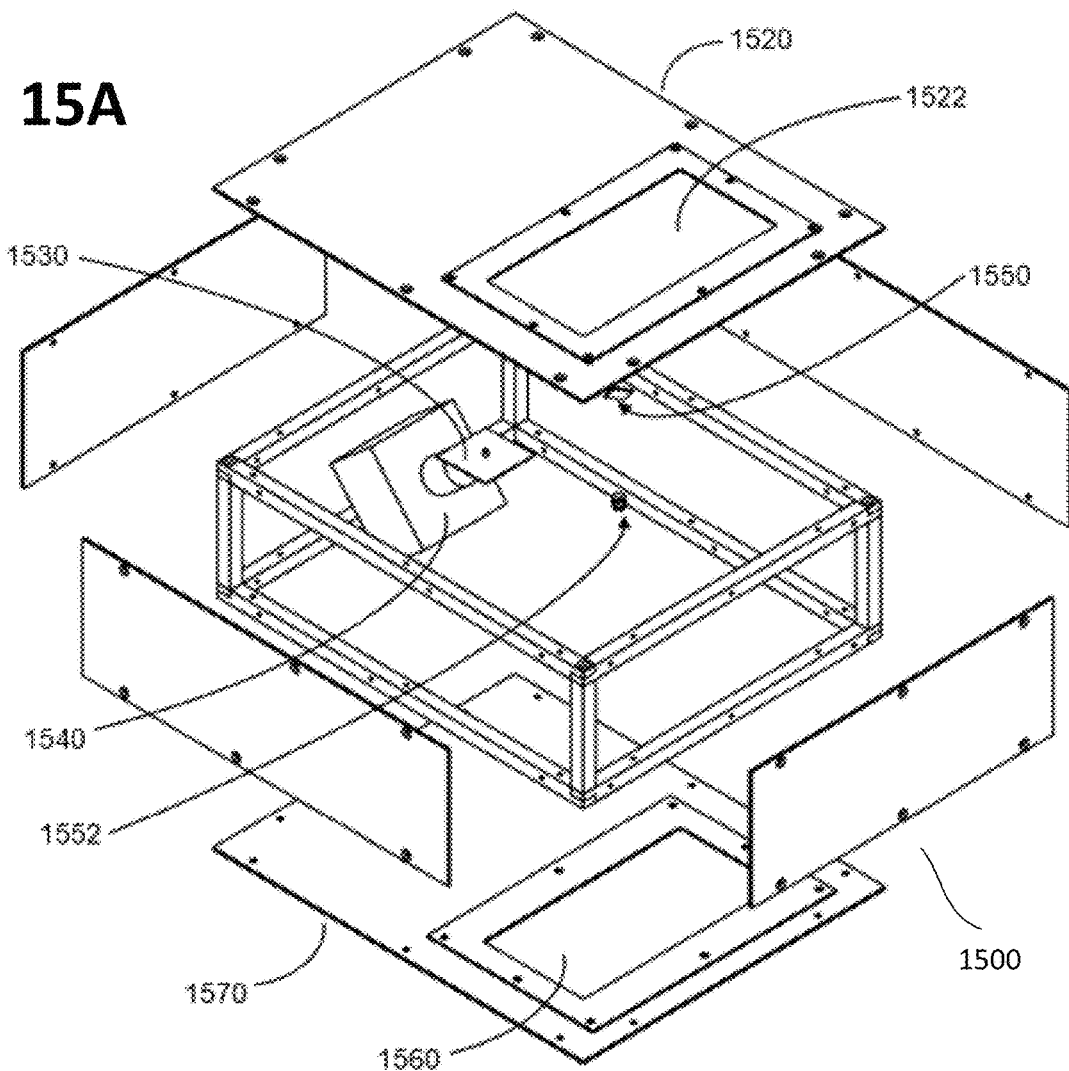
Fig. 15A
Fig. 15B
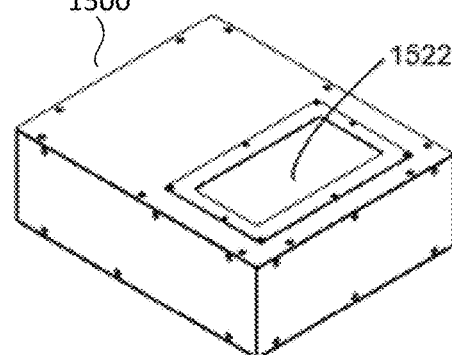
Fig. 15C

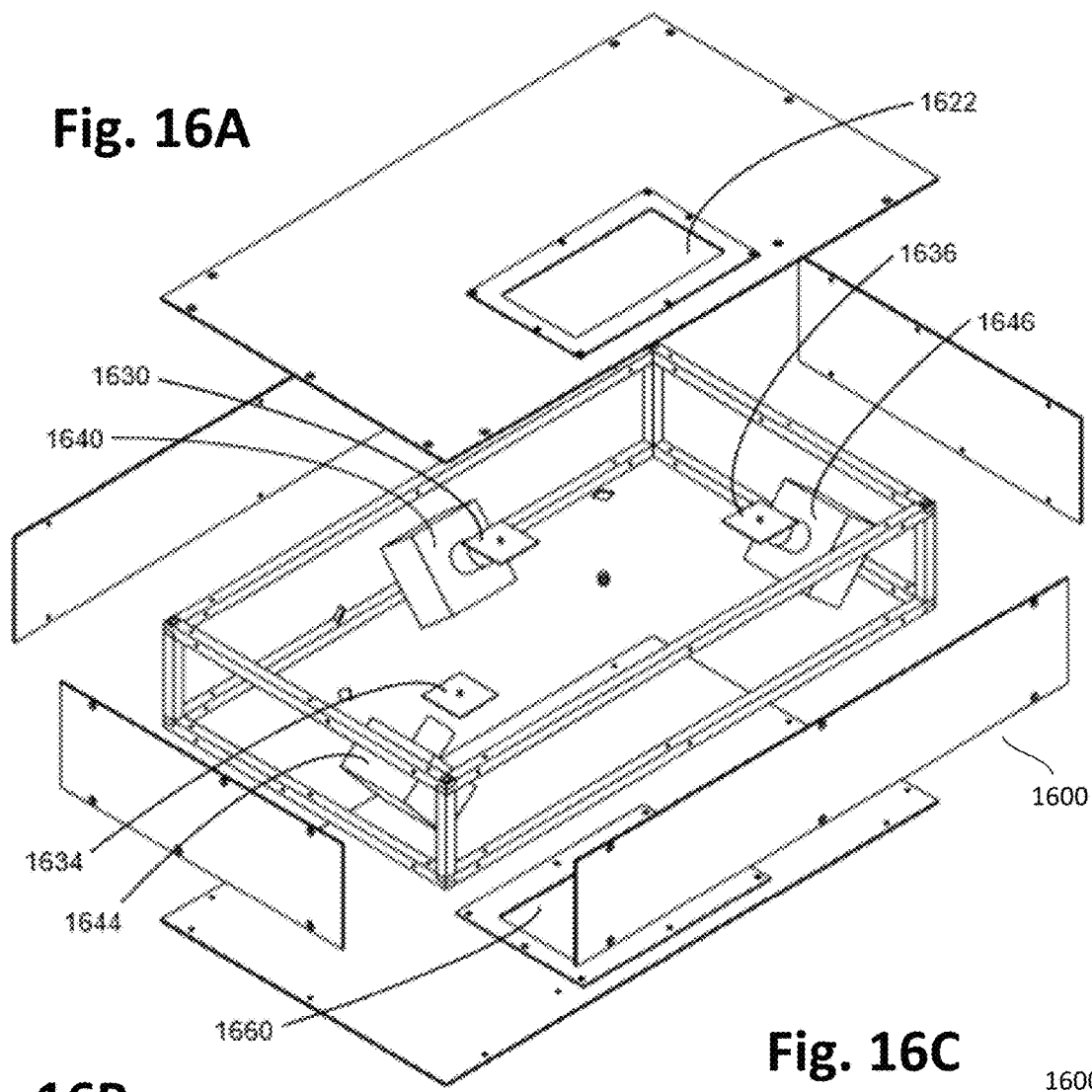
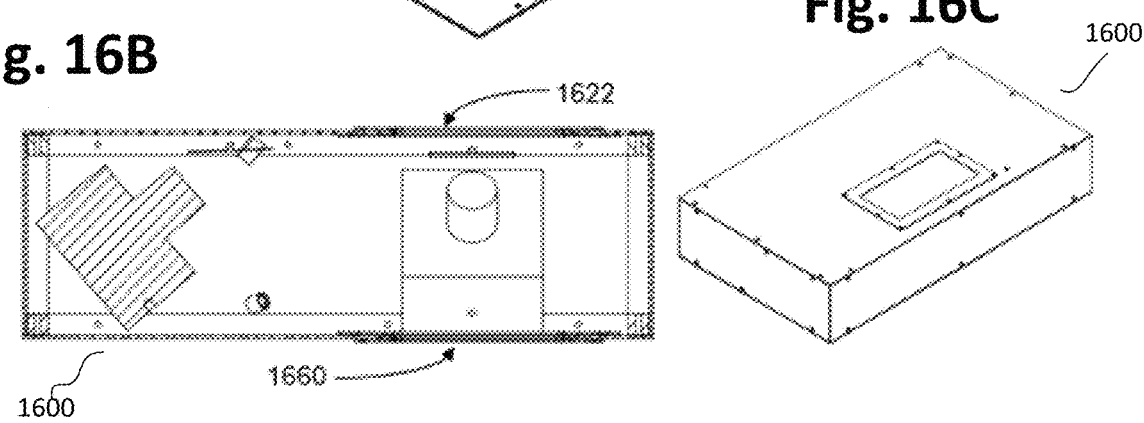

Section A-A

10 µs camera image of ~ 3.6 mm diameter proton beam, moving at 80 mm / ms, irradiating 191 µm thick BoPEN film in vacuum chamber

Four plate light baffle for air circulation

Timing diagram illustrating three sequential camera frames, from two different camera-scintillator systems Image of moving electron beam captured in 21 μs with 2-3 μm spatial resolution

# IONIZING-RADIATION BEAMLINE MONITORING SYSTEM

CROSS-REFERENCE TO RELATED APPLICATIONS

This application is a continuation of U.S. patent application Ser. No. 17/451,517, filed on Oct. 20, 2021, which is a continuation of U.S. patent application Ser. No. 17/332,047, filed on May 27, 2021, which is a continuation of U.S. patent application Ser. No. 17/091,310, filed on Nov. 6, 2020, which is a continuation-in-part of U.S. patent application Ser. No. 16/811,471, filed on Mar. 6, 2020, which is a continuation-in-part of U.S. patent application Ser. No. 16/697,439, filed on Nov. 27, 2019, which is a continuation of U.S. patent application Ser. No. 16/529,200, filed on Aug. 1, 2019, which claims priority to U.S. Provisional Pat. Appln. Ser. No. 62/714,937, filed on Aug. 6, 2018, to U.S. Provisional Pat. Appln. Ser. No. 62/815,006, filed on Mar. 7, 2019, and to U.S. Provisional Pat. Appln. Ser. No. 62/859,952, filed on Jun. 11, 2019. The disclosure of each of these applications is hereby incorporated by reference.

GOVERNMENT LICENSE RIGHTS

The invention was made in part with government support under one SBIR (Small Business Innovation Research) Grant (Number: 5R44CA183437) awarded to Integrated Sensors, LLC by the National Institutes of Health (National Cancer Institute), and two SBIR Assistance Agreements (Award Nos. DE-SC0013292 and DE-SC0019597) awarded to Integrated Sensors, LLC by the U.S. Department of Energy (Office of Science). The government has certain rights in the invention.

FIELD

One embodiment is directed generally to radiation beam monitoring, and in particular to monitoring ionizing beams of particle or photon radiation while having minimal impact on the quality of the radiation beam itself.

BACKGROUND INFORMATION

The most common type of radiation therapy for the treatment of cancer is external beam radiation therapy ("EBRT"). For this treatment, an accelerator is used to generate and precisely deliver relatively high-energy particle or photon beams from outside the body into the tumor. There are a variety of EBRT technologies, with the type of radiation used falling into two general categories: (1) ionizing particles such as protons, ions, electrons, etc., and (2) ionizing photons such as relatively low-MeV gamma rays or X-rays. Ionizing photons are the more common type of radiation employed for EBRT. For particle beam radiation therapy, in addition to protons, carbon ions and electrons, other types of particle beams used or being investigated include helium, oxygen, neon and argon ions, as well as low-energy neutrons (e.g., slow to thermal neutrons). Low-energy neutrons are used, for example, in boron neutron capture therapy ("BNCT") and gadolinium neutron capture therapy ("Gd-NCT").

For both particle and photon EBRT, there are a variety of delivery methods, including intensity modulated radiation therapy ("IMRT"), intensity modulated proton therapy ("IMPT"), three-dimensional conformal radiation therapy ("3D-CRT"), image guided radiation therapy ("IGRT"), volumetric modulated arc therapy ("VMAT"), pencil-beam spot scanning, pencil-beam raster scanning, helical-tomotherapy, stereotactic radiosurgery ("SRS"), stereotactic body radiation therapy ("SBRT"), fractionated stereotactic radiotherapy ("FSRT"), spatially fractionated grid radiation therapy ("SFGRT"), ultrahigh dose-rate flash therapy ("FLASH"), intraoperative radiation therapy ("IORT"), boron neutron capture therapy ("BNCT"), gadolinium neutron capture therapy ("Gd-NCT"), etc.

SUMMARY

Embodiments are directed generally to an ionizing-radiation beamline monitoring system that includes a vacuum chamber structure with vacuum compatible flanges through which an incident ionizing-radiation beam enters the monitoring system. Embodiments further include at least one scintillator within the vacuum chamber structure that can be at least partially translated in the ionizing-radiation beam while oriented at an angle greater than 10 degrees to a normal of the incident ionizing-radiation beam, a machine vision camera coupled to a light-tight structure at atmospheric/ambient pressure that is attached to the vacuum chamber structure by a flange attached to a vacuum-tight viewport window with the camera and lens optical axis oriented at an angle of less than 80 degrees with respect to a normal of the scintillator, and at least one ultraviolet ("UV") illumination source facing the scintillator in the ionizing-radiation beam for monitoring a scintillator stability comprising scintillator radiation damage.

BRIEF DESCRIPTION OF THE DRAWINGS

FIGS. 14A-D illustrate a system that includes a two camera, two mirror, full-size single scintillator/window module beam monitor in a slim light-tight enclosure in accordance with embodiments.

FIGS. 15A-C illustrate a system that includes a one camera, one mirror, half-size rectangular single scintillator beam monitor in accordance with embodiments.

FIGS. 16A-C illustrate a system that includes a three camera version of the embodiments shown in FIGS. 15A-C in accordance with embodiments.

DETAILED DESCRIPTION

Figure 1:
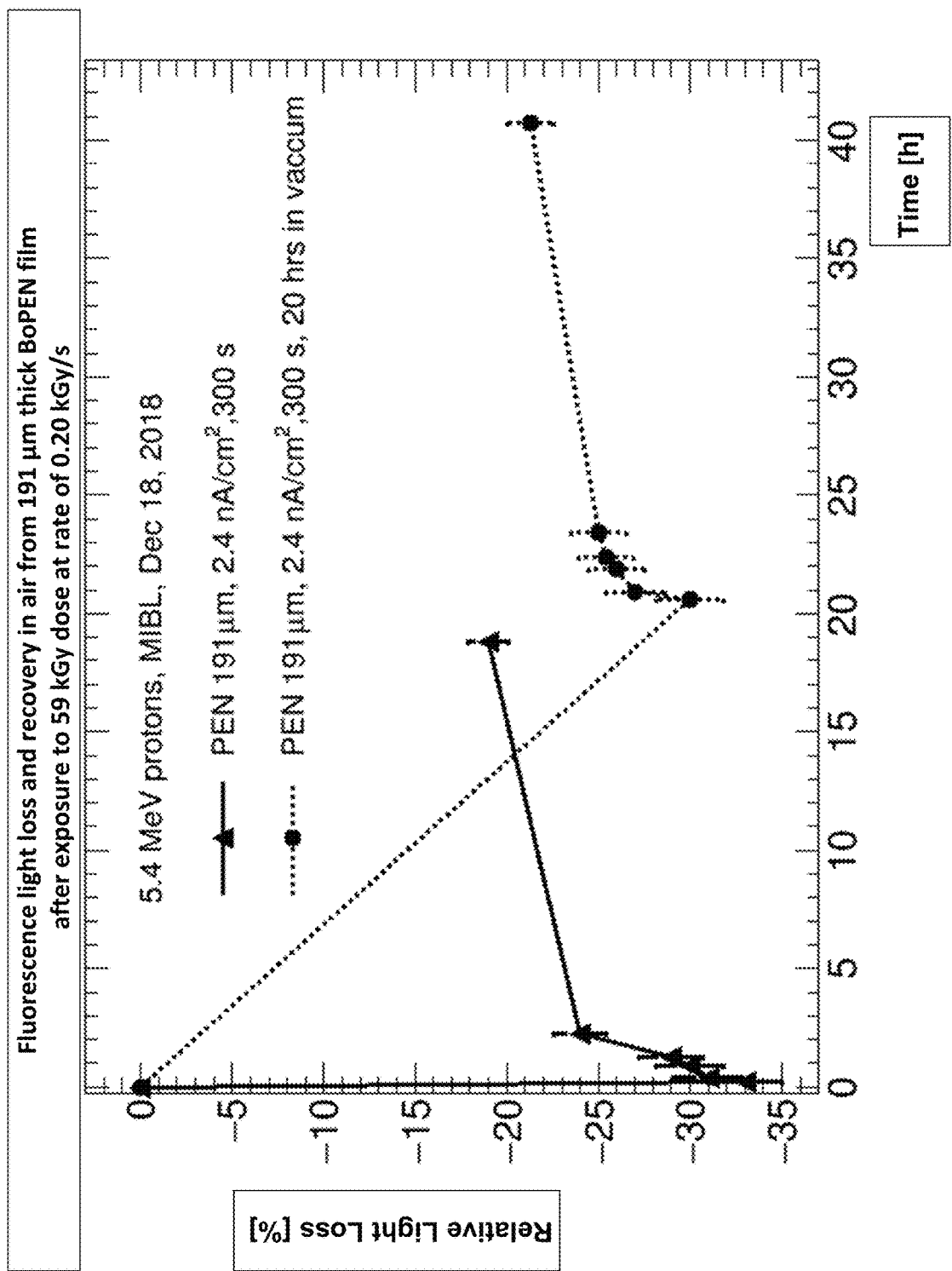
FIG. 1 is a radiation damage recovery plot as a function of time (in hours) for 191 µm thick BoPEN film in accordance to embodiments.

Embodiments are directed generally to ultra-fast transmissive ("UFT") two-dimensional ("2D"), high resolution, ionizing particle and photon beam monitors primarily for applications based on, or related to, external beam radiation therapy ("EBRT"), including the monitoring in "real-time" of beam position and movement, intensity profile including tail, beam fluence/external dosimetry, angular divergence and patient treatment quality assurance.

In embodiments of the present disclosure, the term "ultra-fast" refers to "real-time" on-line monitoring and data analysis of streaming images of an ionizing-radiation beam within approximately 10 ms or less per image, corresponding to a data analysis rate of approximately 100 frames per second ("fps") or faster. For some embodiments, the streaming images can be coming in at rates of 1,000 to 10,000 fps (i.e., 1 ms to 0.1 ms) with the data analysis occurring concurrently. Further, the terms "transmissive" and "highly transmissive" are adjectives used to describe the relatively small amount of energy that a particle or photon loses in transit through a given material or system, which will be different for an entrance or exit window as compared to the scintillator material itself as compared to the integrated beam monitor system comprising the entrance window, exit window, scintillator, and the column of air between the entrance and exit windows. For any given system the relative amount of energy loss will vary greatly at different incident particle or photon energies which can vary over many orders-of-magnitude, and for different types of particles from neutrons to protons to carbon-ions, etc. For an EBRT application such as proton therapy using a proton beam having an incident energy of 210 MeV, the term "highly transmissive" would mean losing no more than about ≤0.1% of its incident energy in transit through the UFT beam monitor system (i.e., losing ≤0.2 MeV), but for the exact same system at 80 MeV "highly transmissive" would mean losing ≤0.5% (i.e., losing ≤0.4 MeV). For this example at the same energies, the term "transmissive" would mean at 210 MeV losing no more than about ≤0.2% of its incident energy in transit through the UFT beam monitor system (i.e., losing ≤0.4 MeV), but for the same system at 80 MeV the term "transmissive" would mean losing ≤1% (i.e., losing ≤0.8 MeV).

The beam monitors in accordance to embodiments incorporate thin and ultra-thin scintillator materials (e.g., scintillator sheet or film material) and are capable of internal, frequent, self-calibration to compensate for a variety of factors including system non-uniformity including camera sensor/pixel response, optical system distortions, slow degradation of the scintillator material due to radiation damage, signal drift due to temperature rise within the monitor enclosure, etc. In embodiments, the term "ultra-thin" refers to both window (i.e., entrance and/or exit window) and scintillator materials having a thickness of ≤0.05 mm, and the term "thin" refers to scintillator materials having a thickness of ≤0.5 mm and thus also includes ultra-thin scintillators.

The integrated detector/monitor in accordance to embodiments has an intrinsic 2D position resolution in the range of ~0.03 mm to 0.2 mm, depending on the application specification requirements, and is highly transparent to the incident ionizing particle or photon beam, thereby resulting in minimal beam scatter, low to extremely low energy straggling, and minimal generation of secondary radiation. Embodiments, in addition to EBRT, can be used for the monitoring of low-luminosity exotic particle beams and/or high-luminosity particle beams generated by research accelerators for scientific experiments, industrial particle and photon beam monitoring for materials processing (e.g., high energy ion implantation, food and medical sterilization, cutting and welding, etc.), materials analysis, non-destructive analysis, radioisotope production, etc. Beam monitors in accordance to embodiments generally do not require a controlled atmosphere or vacuum environment for proper operation, although some embodiments have been designed for operation in vacuum or controlled gaseous environments.

Embodiments for EBRT applications generally result in positioning the beam monitor downstream from the accelerator exit nozzle in an ambient air atmosphere. However, other embodiments are configured to operate within the vacuum environment of the beamline pipe to optimize and/or monitor the beam shape, intensity, position and beam focus prior to reaching the beam exit/nozzle or target region. Embodiments for EBRT applications downstream from the nozzle incorporate a unique folded optical configuration to achieve a thin profile to minimize encroaching upon the confined and narrow space between the beam nozzle exit and the patient.

Due to the ultra-fast response capability of the embodiments of beam monitors, they can provide sub-millisecond and even microsecond beam analysis and feedback to the delivery system, thereby allowing corrective actions to be taken if necessary. For EBRT, this capability can potentially improve the treatment delivery efficacy and protect the patient, especially for recent "FLASH" therapy applications. For nuclear and high energy physics, this capability can provide particle time-of-flight (TOF) information in the range of 50 to 100 μs, or greater.

It is known to use a scintillator, including a plastic scintillator, to detect ionizing radiation, coupled with an electronic photodetection device to quantitatively measure the emitted photons from the scintillator. It is also known to use a digital camera to record the light emitted from an irradiated scintillator in applications ranging from monitoring the beam shape and position of an electron beam, to using X-rays irradiating a scintillator to evaluate the quality of mechanical welds, to optimizing the beam delivery system used in proton beam therapy.

In contrast to known uses, embodiments implement multi-camera folded optical configurations, such as 2, 3, 4, 6, 8, 10, 12 cameras, for advanced beam monitoring systems that provide critical performance and space-saving advantages such as extremely high spatial resolution while minimizing encroachment on the limited space existing between the EBRT exit nozzle and the patient's body. Embodiments also include configurations of relatively compact machine vision cameras with imaging sensors that can stream images live to a computer system that includes a frame grabber for real-time data processing and analysis, the use of machine vision cameras that can be programmed for application specific parameter optimization such as selection of exposure time, gray scale level (i.e., bit depth), acquisition control and frame rate, gain control, black level control, gamma correction for pixel intensity, pixel binning, pixel sharpening, windowing down the area or region of interest to achieve higher frame rates for faster beam analysis. Embodiments further include the use of both single and double scintillator configurations that can be integrated as part of an easy to replace foil-window/scintillator module package, and rolled scintillator-film motorized spool assemblies for automated scintillator film advancement/replacement that uses novel polymer thin film scintillator materials such as biaxially-oriented polyethylene naphthalate ("BoPEN"), biaxially-oriented polyethylene terephthalate ("BoPET"), polyethersulfone ("PES"), etc. that are intrinsic scintillators without the addition of fluor dopants. Embodiments include novel designs for quick replacement of radiation damaged scintillator film or sheet with new scintillator film or sheet without significant service downtime and recalibration time associated with the scintillator replacement process, configurations for real-time beam monitoring systems operating in a vacuum environment, configurations for beam monitoring systems operating in either a naturally circulating or controlled flow-through ambient air or special gaseous environment such as an enriched oxygen gaseous atmosphere to possibly minimize radiation damage by enhancing oxygen assisted radiation damage recovery, configurations incorporating actively cooled camera sensors for enhanced performance and reduced radiation damage of the camera sensor element, configurations incorporating the addition of internal UV sources such as UV-LEDs and internal UV detectors such as UV-photodiodes and appropriate filters such as bandpass filters to achieve internal self-calibration of system non-uniformity and near continuous self-correction for progressive scintillator radiation damage; real-time software correction of optical system distortions, perspective distortions (e.g., keystoning), aberrations and non-uniformities including camera image sensor pixel defects and non-uniformity.

Embodiments include configurations utilizing 3-way tees or wyes, 4-way-cross, 5-way-cross and 6-way-cross vacuum chamber configurations for beamline vacuum operation that allow the use of either two cameras, or two photomultiplier tubes ("PMT"s), or one camera and one PMT, or PMT replacements such as solid state photomultipliers ("SSPM") including silicon photomultipliers ("SiPM"), avalanche photodiodes ("APD"), single-photon avalanche diodes ("SPAD"), etc. Embodiments include high dynamic range ("HDR") computational imaging and with the thinnest scintillator films have extremely low beam energy straggling with minimal generation of secondary ionizing particles and photons.

Embodiments achieve advantages in part by using a scintillator film material, available in continuous rolls (e.g., >1000 ft length) of about 70 cm width and greater, and thicknesses from about 1 μm to 250 μm in conjunction with other components to achieve unexpected results with regard to radiation damage resistance, photon emission, and as a thin and/or ultra-thin film scintillator. Embodiments include designs to take advantage of the new thin and ultra-thin scintillator material which is highly resistant to radiation damage, while being able to minimize and possibly eliminate most problems having to do with scintillator non-uniformity and time consuming scintillator material replacement and system calibration.

Embodiments include an innovative folded-optics design to minimize the product profile/thickness to within about 6-14 cm, depending upon scintillator and camera size and camera angle. Embodiments include an innovative automated, internal, rapid calibration system using UV-LEDs, UV-photodiodes, and UV and VIS bandpass filters, with an estimated time for system calibration of about one minute or less. Embodiments include machine vision cameras that would typically stream images at frame rates from about 10 fps to 40,000 fps.

Embodiments discussed below include an in-line beam monitor design (e.g. FIGS. 11-13) with fast, high gain photomultipliers (e.g., approaching $1 \times 10^7$), coupled with an efficient photon collection system and suitable scintillator and radiation source (e.g., highly ionized particles with an atomic number of ~10 or greater, such as $Ne^{+10}$) capable of generating at least ~200 photoelectrons and achieving on the order of about 100 ps timing resolution, and possibly better than 50 ps timing resolution, which is critically important for time-of-flight ("TOF") experiments.

Embodiments further enhance timing resolution for TOF measurements by increasing photon collection, such as through the use of two PMTs or SSPMs in the opposite arms of a 6-way-cross instead on one PMT (or SSPM) and one camera, or improving the collection of photons from the front side of a scintillator by depositing a reflective coating on the scintillator back side, or roughening the front collection surface of a scintillator to prevent total internal reflection.

Embodiments include multi-camera configurations (e.g. 2, 3, 4, 6, 8, 10, 12, etc., cameras) with FPGA frame grabbers and software that can compile, integrate and analyze streaming images in real-time of the moving beam, while correcting for optical image perspective/keystone distortions, lens distortions, vignetting, scintillator non-uniformity, camera sensor pixel non-uniformity, defective and radiation damaged pixels, etc.

Embodiments include manual or motor controlled push-pull linear positioners and/or rotary drives to advance fresh scintillator film as needed into the incident beam active area. Embodiments include a load-lock vacuum chamber design to change scintillator films without having to break the beamline vacuum. Embodiments include an ultra-thin, light-blocking beam entrance and exit foil and/or polymer window, bonded to a thin frame, that can also be bonded to the scintillator film or sheet material to make a simple window/scintillator replaceable module package that can be dropped into a pocket in the beam monitor front and/or back cover plate and calibrated within a minute or so without having to open up the system enclosure.

Embodiments have a design based on two different in-line scintillators, one sensitive to essentially all particles and high energy photons/gammas except neutrons, and the other doped with a high neutron cross-section isotope such as $B^{10}$, $Li^6$ or Gd in order to make it neutron sensitive. By digitally subtracting the image/signal of the first scintillator from that of the second scintillator, the resulting second scintillator image/signal will be primarily that of the neutron beam and can achieve the high performance at low cost desired in a high gamma discrimination neutron detection system.

Most known EBRT particle accelerators are designed for pencil-beam spot scanning, but a few systems are designed for pencil-beam raster scanning. The beam monitor embodiments disclosed below are compatible with both types of pencil-beam scanning systems, with most configured to operate downstream from the exit nozzle, but some embodiments have been designed to operate upstream of the nozzle in the vacuum environment of the beamline delivery system either in the patient treatment room or prior to the treatment room and switch house and close to the accelerator. The purpose of such systems operating in the beamline vacuum is usually diagnostic to facilitate beam tuning including measurement and optimization of the 2D beam profile in the delivery system, whether for EBRT, or for nuclear and high energy physics. In all cases, the scintillator material should be an extremely thin film so as to be almost transparent with very little low energy straggling so as not to degrade the beam in the process of measuring it. For such applications, the scintillator film in some embodiments should be less than 100 μm thick and possibly as thin as 1 μm.

In embodiments the scintillator film BoPEN is employed in thickness down to 1 μm, and in some embodiments this film is physically attached to a rigid frame as shown in some of the 6-way-cross embodiments disclosed below.

Experimental results showed a 33.0% initial decrease in scintillator fluorescence from a 191 μm thick BoPEN film measured almost immediately after being irradiated for 5 minutes by a low energy proton beam that resulted in a film dose of 59 kGy. Specifically, FIG. 1 is a radiation damage recovery plot as a function of time (in hours) for 191 μm thick BoPEN film exposed at a proton dose rate of 0.20 kGy/s, for 5 minutes, corresponding to a total dose of 59 kGy in accordance to embodiments. In the left plot the relative light loss was measured almost immediately in air after exposure, while in the right plot the sample was kept for ~21 hours in vacuum before being removed and then measured in air. However, after a 19-hour period in an ambient air atmosphere, the fluorescence emission in the left plot had partially recovered and the decrease was measured to be about 19.7%, representing about a 40% radiation damage reversal/recovery in less than one day. As shown in FIG. 1, most of the recovery occurred within the first few hours, but radiation damage recovery in air can continue for many days and even weeks, albeit at a much-reduced rate.

The above BoPEN film (density of 1.36 g/cc) radiation damage experiments employed a 5.4 MeV proton beam that was continuously irradiated for 300 seconds at an incident beam current density of 2.4 nA/cm². Upon passing through the BoPEN film, each 5.4 MeV proton loses about 2.14 MeV. Given the above beam current and integrated exposure time, the BoPEN scintillator film was subjected to 59 kGy of accumulated radiation dose (1Gy=1 J/kg) absorption as calculated below:

$N=(2.4 \times 10^{-9} \text{ coul/sec-cm}^2)*(6.25 \times 10^{18} \text{ protons/coul})*(300 \text{ sec})=4.5 \times 10^{12} \text{ protons/cm}^2$ $J=2.14 \text{ MeV/proton}=(2.14 \times 10^6 \text{ eV/proton})*(1.6 \times 10^{-19} \text{ J/eV})=3.4 \times 10^{-13} \text{ J/proton}$ $$\text{Mass}=(1.36 \text{ g/cm}^3)*(0.0191 \text{ cm})=0.026 \text{ g/cm}^2=2.6\times 10^{-5} \text{ kg/cm}^2$$

$$\text{Dose}=(3.4\times 10^{-13} \text{ J/proton})*(4.5\times 10^{12} \text{ protons/cm}^2)/2.6\times 10^{-5} \text{ kg/cm}^2=1.53 \text{ J}/2.6\times 10^{-5} \text{ kg}=59\times 10^3 \text{ Gy}$$

$$\text{Dose rate}=59 \text{ kGy}/300 \text{ sec}=0.20 \text{ kGy/s}$$

For a transmissive particle beam monitor based on viewing and measuring the beam via its effect on scintillator emission, the effect of radiation damage can be quantified by equating it to the reduction in scintillator yield as measured by relative light loss (i.e., fluorescence signal reduction). With respect to obvious visual radiation damage, none of the more than 30 BoPEN samples irradiated to date, at dosage levels up to ~60 kGy, have shown any visual signs of scintillator discoloration or surface degradation which was an unexpected result. However, BoPEN films have discolored at 400 kGy (see discussion below and Table 1).

In estimating the acceleration factor in experimental uses for different applications, with proton beam therapy being of particular interest, an average conventional daily patient treatment regime delivers ~2 Gy per session. So, the above test that delivered 59,000 Gy to the BoPEN scintillator film in 300 seconds is presumably equivalent to the dose incurred in treating ~30,000 patients. In other words, 1 second of accelerated irradiation in the 5.4 MeV test beam, approximately simulates the radiation received by the scintillator in conventionally treating ~100 patients (a lesser number of patients for FLASH therapy). Or viewed another way, if a typical proton beam treatment room can process about 30 patients per day, then 5 minutes of the above accelerated proton beam test is equivalent to ~1000 days of conventional patient treatments in a one-room facility. This degree of radiation damage resistance, with no obvious visual sign of surface degradation or discoloration in an off-the-shelf commercial polyester film, under such an aggressive, high rate, accelerated testing regime is an unexpected result.

Figure 2:
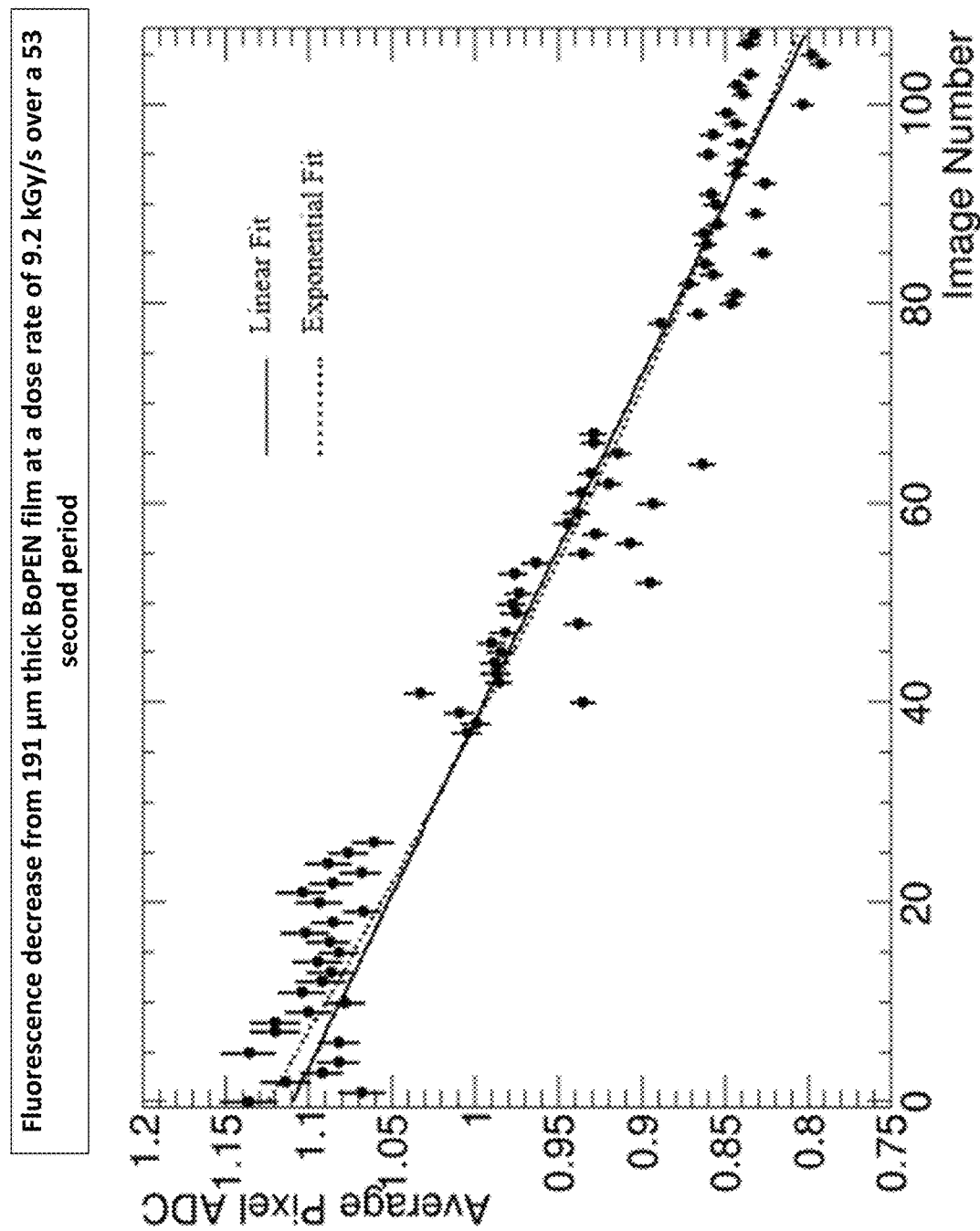
FIG. 2 is a plot of the average pixel signal decrease as a function of time for a 191 µm thick BoPEN film in accordance to embodiments.

FIG. 2 is a plot of the average pixel signal decrease as a function of time for a 191 μm thick BoPEN film exposed at a proton dose rate of 9.2 kGy/s, for 53 seconds, corresponding to a total dose of 490 kGy in accordance to embodiments. The time scale is shown in terms of the camera image numbers recorded at 2 fps of the BoPEN film while being irradiated in a vacuum chamber. It can be seen that even at this high dose rate there is relatively little difference between the linear and exponential fits.

From the BoPEN scintillator test experimental results to date, it appears that at the above dose rate of 0.2 kGy/s that radiation damage is linear with exposure, up to rates approaching 10 kGy/s (as shown in FIG. 2). By assuming linearity, corrections can be made for the increased radiation damage that occurs at the sample back surface by supposing that the average value between the front entrance and back exit surfaces provides a reasonable estimate of the fluorescence coming from the sample middle bulk layer. In making this correction, the bulk fluorescence value from the sample center now becomes 22.2% greater than from the back surface. Thus the measured back surface light loss values can be corrected to obtain a more accurate bulk fluorescence value by multiplying the measured back surface values in FIG. 1 by 77.8%. Making this correction, the 59 kGy dose exposure which caused a 33.0% decrease in initial fluorescence and the 19.7% decrease in fluorescence after 19 hours, respectively becomes a 26% decrease (i.e., 0.778*33%) in initial fluorescence and a decrease after 19 hours.

Hence the measured rad-damage values previously stated and appearing in FIG. 1 are overstated by 22.2% for the 191 μm thick BoPEN films. However, for ultra-thin BoPEN films with a thickness of ≤25 μm, the correction factors would be <1% and negligible. Likewise, for therapeutic particle beams with incident proton energies in the range of 70-225 MeV, even for the thin 191 μm thickness BoPEN film, there is no significant difference between the dose received at the front and back layers, and thus the surface fluorescence signal as measured using a 280 nm UV-LED source (located behind the BoPEN film and 99% absorbed in the first 0.1 μm back surface layer) accurately represents the radiation damage at these energies to the bulk material.

Figure 3:
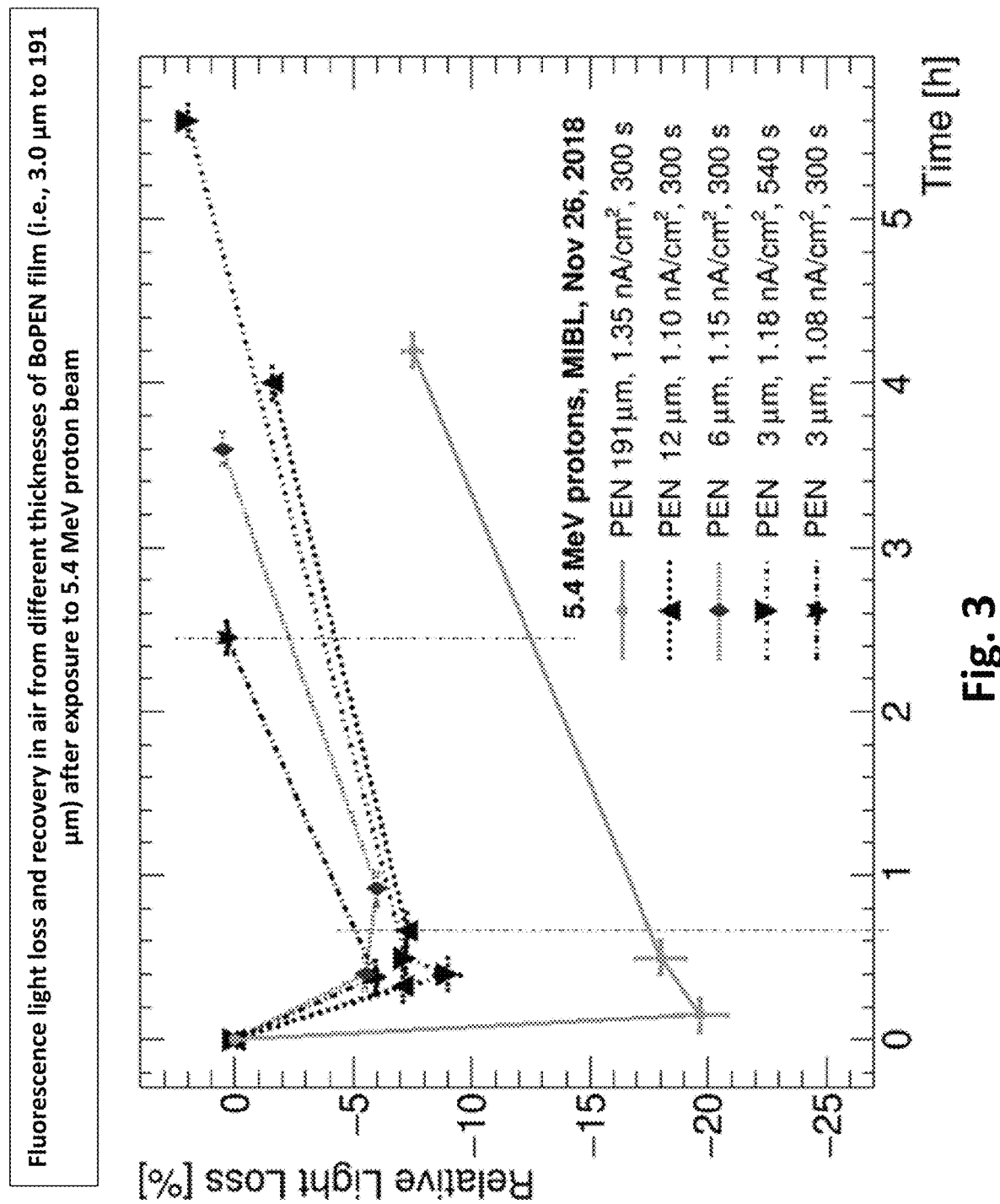
FIG. 3 is a plot of the fluorescence light loss and recovery in air as a function of time for different thicknesses of BoPEN film in accordance to embodiments.

FIG. 3 is a plot of the fluorescence light loss and recovery in air as a function of time for different thicknesses of BoPEN film, ranging from 3.0 μm to 191 μm, after exposure to a 5.4 MeV proton beam in accordance to embodiments.

As can be seen in FIGS. 1 and 3, and in general for all BoPEN films, most of the radiation damage recovery in air occurs within the first few hours. The differential radiation damage effect described above, for thick versus thin scintillator films, explains the apparent differences in relative light loss shown in FIG. 3. For example, in comparing the maximum 7.3% light loss for the 12 μm thick BoPEN film measured after 40 minutes to the 17.5% light loss (from the back surface) for the 191 μm thick BoPEN film plotted after 40 minutes (i.e., dashed vertical line at 0.67 hours), the two values agree within an uncertainty of ±10% (i.e., 7.3% vs. 7.9%). The calculation for 191 μm thick BoPEN film is as follows:

$$\text{Initial adjustment for front surface light loss in 191 μm film}=(1-0.444)*(17.5\%)=9.7\%$$

$$\text{Additional adjustment for difference in beam current density}=(1.10/1.35)*(9.7\%)=7.9\%$$

Further, in experiments there was excellent agreement from two different 191 μm thick BoPEN samples, measured more than three weeks apart, using significantly different beam currents. In particular, the initial 19.7% light loss in FIG. 3, when adjusted for the higher beam current density in FIG. 1 (2.4/1.35), yields an adjusted beam loss value of 35.0% compared to 33.0% in FIG. 1.

In estimating the beam energy lost in transit through the film, and the beam shape and intensity via its fluorescence profile, it is necessary to know the BoPEN film thickness and uniformity. A convenient non-destructive method for measuring film thickness and uniformity is via the front/back surface reflectance generated by spectral interference. This method can accurately measure film thicknesses over the full range from ~1 μm to 250 μm, and to within about ±0.1 μm accuracy. For the films in FIG. 3, the measured thicknesses were: 3.0, 5.8, 12.2 and 191.0 μm, as measured by spectral reflectance in the near-IR over the wavelength range from ~1,000 to 1,900 nm.

The above data indicates that thinner BoPEN scintillator films appear to be more radiation damage resistant than the thicker films (e.g., see the 300 second plots for the 3, 6, 12 and 191 μm thickness BoPEN films in FIG. 3 at both 0.67 and 2.45 hours). This result is completely unexpected and surprising, and counter intuitive to what was previously expected. Explanations for this unexpected result include that radiation damage recovery is significantly faster in the thinner films in air as suggested by the narrow dashed vertical line intersecting the thickness film plots at 2.45 hours and the projections further out at 4-5 hours in which the radiation damage appears to be essentially fully reversed for the thinnest films as compared to the 191 μm thick film. Another explanation includes that radiation damage depends on the probability of free-radical interaction, or a multi-particle free-radical mechanism, and so the thicker films having a greater free-radical density at the exit surface due to dE/dx, also has a higher probability of single or multiple free-radical proximity interactions. Other explanations include that the thinner films have a faster and higher probability of free-radical migration and diffusion to the film air surface, and because the FIG. 3 measurements were all in air, the thinner films have a higher rate of oxygen permeation and diffusion, as well as singlet oxygen escape. Being able to provide a verifiable mechanism to explain the higher radiation damage resistance of the thin films is not necessary, as the unexpected good news is that for BoPEN the thinner scintillator films appear to be more radiation damage resistant (i.e., rad-hard) than the thicker films.

In embodiments, in order to refine the above estimates for the scintillator dose exposure under more realistic clinical proton therapy conditions, an additional 20% scintillator dose can account for patient planning and calibration activity, and weekly machine maintenance. This adjustment means that the previously stated estimate of 30 patients per day, at 2 Gy per patient, corresponding to 60 Gy per day scintillator dosage, might prudently be increased by about 20% to 72 Gy per day. Therefore, the above calculated 59 kGy of accelerated exposure at a test facility, would be equivalent to 819 days of accumulated patient service assuming conventional irradiation treatment (i.e., not FLASH).

If a proton beam facility operates 5 days per week, then 819 days of service corresponds to 164 weeks which would be more than 3.1 years of continuous service. Assuming a linear radiation damage model (e.g., shown in FIG. 3), the previously revised measurement of a 15.6% loss in scintillator efficiency due to radiation damage (i.e., loss in fluorescence after 19 hours) would correspond to a 0.156% efficiency loss every 8.19 days. However, since radiation damage recovery continues well beyond 19 hours, then over the course of 8.19 patient treatment days the accumulated damage will certainly be less than 0.15%. More specifically, for a 5-day patient treatment week the accumulated proton rad-damage is likely ≤0.09% per week for the 191 μm thick BoPEN film assuming a 2 Gy dose to the scintillator per patient.

Figure 4:
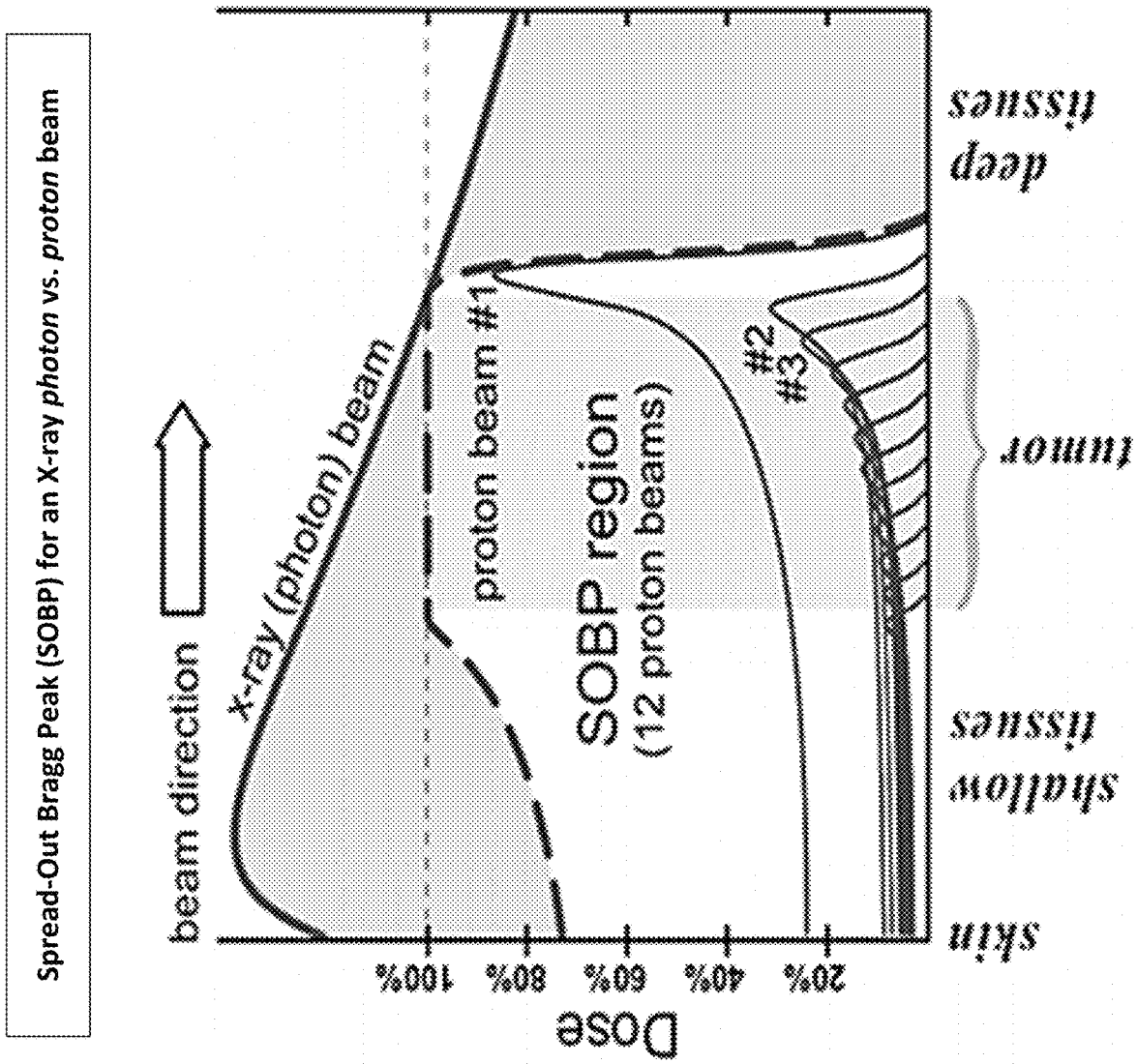
FIG. 4 illustrates an example of the Spread-Out Bragg Peak ("SOBP") for an X-ray photon vs. proton beam in accordance to embodiments.

FIG. 4 illustrates an example of the Spread-Out Bragg Peak ("SOBP") for an X-ray photon vs. proton beam in accordance to embodiments. FIG. 4 shows that the above estimate overstates the rad-damage to the scintillator, because 2 Gy to the patient does not equal to 2 Gy to the scintillator due to the SOBP. The SOBP means that if the tumor receives 2 Gy, then depending upon such factors as the tumor density, thickness and location, which determine the proton beam energy, the radiation dose delivered to the skin, or scintillator will typically fall in the range of about 50% to 75% of the dose to the patient's tumor, and would be about 1.0-1.5 Gy. Therefore, instead of the accumulated BoPEN rad-damage being ≤0.09% per week as estimated above, after correcting for the SOBP, the 191 μm thick BoPEN scintillator should suffer a rad-damage loss of only about 0.04% to 0.07% per week. This result is most surprising and leads to the unexpected conclusion that on a weekly and probably monthly basis the rad-damage to a 191 μm thick BoPEN scintillator is practically negligible, and even more so if a thinner BoPEN scintillator can be used.

Figure 5:
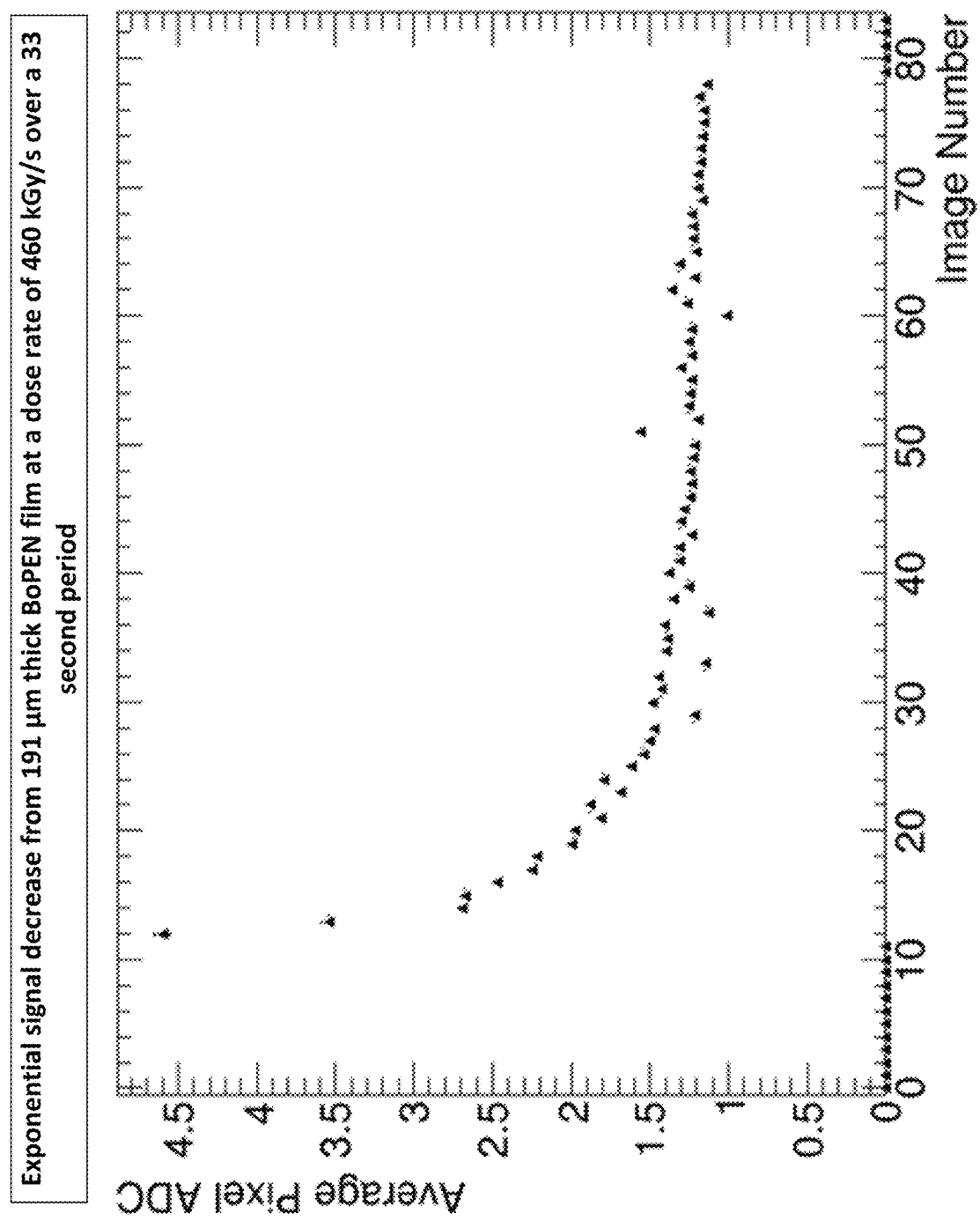
FIG. 5 is a plot showing the exponential fluorescence decrease as recorded by the average camera pixel signal in accordance to embodiments.

FIG. 5 is a plot showing the exponential fluorescence decrease as recorded by the average camera pixel signal measured off of a 191 μm thick BoPEN film exposed at a proton dose rate of 460 kGy/s, for 33 seconds, corresponding to a total dose of 15,000 kGy in accordance to embodiments. The time scale is shown in terms of the camera image numbers recorded at 2 fps of the BoPEN film while being irradiated by a 3.0 MeV proton beam in a vacuum chamber. As shown in FIG. 5, and Table 1 below, at the highest measured dose rates, the radiation damage is not linear with exposure but is exponential. This means that estimates made at these high dose rates (e.g., ≥90 kGy/s) can be misleading in projecting greater scintillator radiation damage than actually incurs at lower dose rates integrated over longer periods of time. In other words, if the accelerated test data has a significant exponential component, then the actual scintillator radiation hardness would be better than stated above.

However, it appears that in the range of accelerated radiation dose rates chosen for modeling the performance of both therapeutic particle beams and for nuclear physics particle beam monitors (i.e., dose rates of ≤9 kGy/s shown in Table 1), projections based on a linear model should provide a good estimate of scintillator performance and any corrections for exponential behavior would be minor as shown in FIG. 2. For example, at a measured dose rate of 9.2 kGy/s, the linear relationship for BoPEN films still appears reasonable (see FIG. 2) corresponding to delivering 0.5 MGy in just 53 seconds (shown in Table 1), which is an unexpected result. Yet at dose rates of ≥90 kGy/s, deviations from linearity are major and calculations based on the assumption of linearity would be erroneous and should only be used for qualitative purposes. At these much higher dose rates, slow to moderate scintillator ablation begins instantaneously (see FIG. 5 and Table 1).

TABLE 1

Summary of MIBL Proton Beam Accelerated Test Results for 191 μm thick BoPEN Scintillator

| Dose Rate (kGy/s) | Current Density (nA/cm²) | Beam Current (nA) | Beam Energy (MeV) | Dose (kGy) | Rad-Damage Observations | Date |
|---|---|---|---|---|---|---|
| 0.11* | 1.35 | 5.4 | 5.4 | 33 | No discoloration. Minimal rad-damage, largely reversible* | Dec. 18, 2018 |
| 0.20 | 2.4 | 9.6 | 5.4 | 59 | No discoloration. Fluorescence loss mostly reversible | Dec. 18, 2018 |
| 3.3 | 40 | 10.0 | 5.4 | 390 | Sample 16: Area darkening disappeared 2 months later | Nov. 26, 2018 |
| 9.2 | 50 | 1 | 3.0 | 490 | Sample 13: No ablation but 0.6%/sec fluorescence decrease | Dec. 18, 2018 |
| 92 | 500 | 10 | 3.0 | 6,100 | Sample 13: Immediate but slow surface ablation | Dec. 18, 2018 |
| 460 | 2,500 | 50 | 3.0 | 15,000 | Sample 13: Immediate fast surface ablation => deep hole | Dec. 18, 2018 |

*Rate of 110 Gy/s with minimal rad-damage is well in excess of the 40 Gy/s rate used for FLASH proton therapy.

None of the BoPEN films receiving dosages up to 59 kGy (i.e., 300 seconds with 5.4 MeV proton beam at a current density of 2.4 nA/cm$^2$) and at a dose rate of 0.20 kGy/sec showed any sign of surface degradation or discoloration despite significant decreases in fluorescence due to rad-damage as shown in FIGS. 1 and 3. Both figures show that measurable radiation damage recovery begins in air almost immediately after exposure and that this recovery can continue for days or even weeks afterwards. However in a vacuum environment, such recovery is either greatly reduced or delayed as shown in FIG. 1.

Rad-damage induced darkening (i.e. yellow-brown discoloration) has been observed in a 191 μm thick BoPEN film using the 5.4 MeV proton beam at a 10 nA current, with a fixed, non-rastered beam focused on a 0.25 cm$^2$ area for 118 seconds. The resulting current density of 40 nA/cm$^2$ yielded a dose rate of 3.3 kGy/s and produced an accumulated dose of 390 kGy. This dose rate was 16 times greater than received by the 59 kGy dose irradiated sample disclosed above. However, when the 390 kGy dose film was viewed two months later, it was discovered that the darkened/discoloration area had completely disappeared, so apparently at least some visually damaged BoPEN films can self-heal/recover in air to the extent that they no longer appear visually discolored.

In order to evaluate the dosage associated with irreversible physical damage (such as burning a hole into the film by proton ablation), a more stable fixed proton beam accelerator was used with a 191 μm thick BoPEN film at a reduced proton kinetic energy of 3.0 MeV and with a much tighter beam focus over an ablated hole area of 0.020 cm$^2$ (i.e., diameter at hole surface was 1.6 mm as disclosed below), at beam currents of 1 nA for 53 seconds, 10 nA for 66 seconds, and 50 nA for 33 seconds. At each beam current a series of images were recorded at a shutter time/exposure of 1 ms, and at a frame rate of 2 fps for all three cases.

Figure 6A:
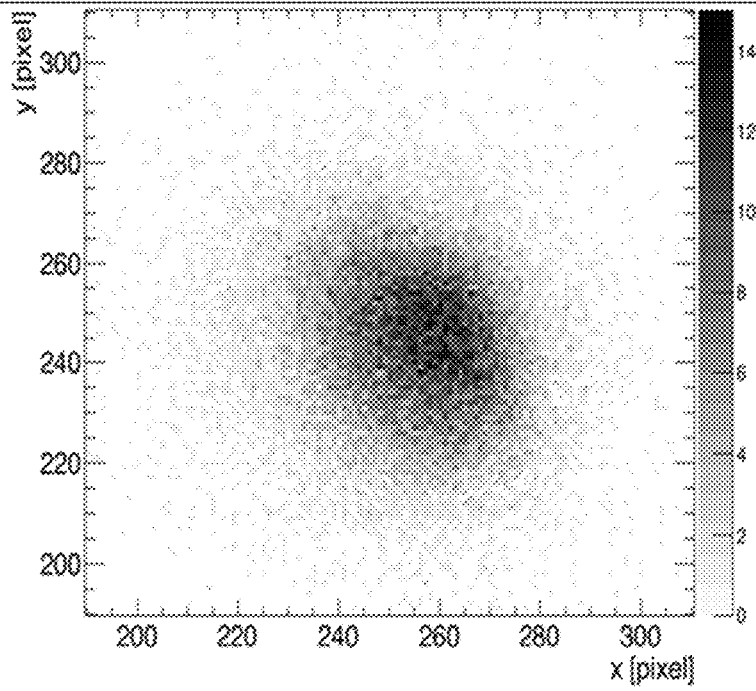
FIGS. 6A-B illustrate two images of a 10 nA, 3.0 MeV proton beam inside a vacuum chamber in accordance with embodiment.
Figure 6B:
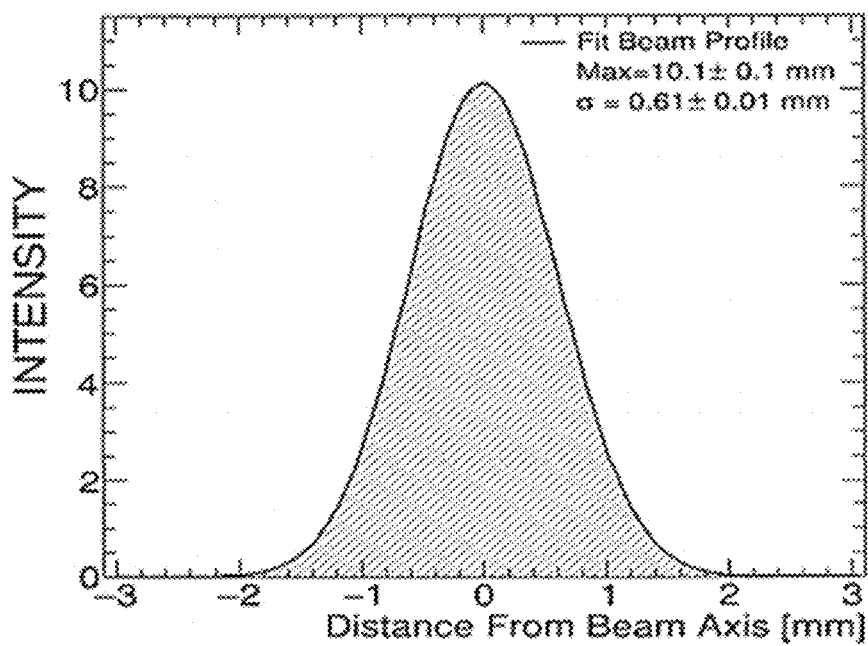

FIGS. 6A-B illustrate two images of the above 10 nA, 3.0 MeV proton beam, having approximately a 2.68 mm diameter, irradiating a 191 μm thick BoPEN film inside a vacuum chamber in accordance with embodiment. FIG. 6A is the digital image recorded with a 1 ms exposure and the pixel image resolution is 38.2 μm. FIG. 6B is a Gaussian fit to FIG. 6A with a measured average σ=0.61 mm and 97% of the beam falling within a 2.2σ radius of 1.34 mm.

The number of images recorded for the above experiment corresponded to 89 images at 1 nA (see disclosure below), 133 images at 10 nA, and 67 images at 50 nA, with the fluorescence pattern and signal intensity recorded for each picture on a pixel-by-pixel basis as seen in FIGS. 6A and 6B for the 1st image taken at a beam current of 10 nA. A complete set of pictures at the three beam currents were taken without breaking vacuum or moving the camera, and by sequentially increasing the beam current after each set of images (i.e., from 1 nA, to 10 nA, to 50 nA) while the beam remained focused on the same scintillator spot area. Therefore, when the BoPEN film was finally removed after the last image at 50 nA, the partially ablated hole/crater represented the sum total from the three beam current doses piled on top of one another. Although the 1 nA beam caused no obvious physical film damage, it did suffer a 0.6% decrease in fluorescence per second of irradiation (i.e., slope was 0.003, see FIG. 2).

As previously disclosed, the fluorescence decrease followed close to a linear fit as seen by the solid line in FIG. 2 (there were two dead periods when images were not taken but beam exposure continued); however, the dotted line in FIG. 2 represents a best fit for an exponential curve which is very close to the linear fit. The linear fit in FIG. 2 corresponds to a current density of 50 nA/cm$^2$, a dose rate of 9.2 kGy/sec, and an accumulated dose of 490 kGy. Since the 10 nA proton beam at 5.4 MeV and 40 nA/cm$^2$ caused yellow discoloration/darkening at a delivered dose of 390 kGy, it is highly probable that the 50 nA/cm$^2$ beam (490 kGy) also caused discoloration of the BoPEN film although it could not be seen since the area was subsequently ablated.

In contrast to the 1 nA fixed beam at 3 MeV, the subsequent 10 nA fixed beam suffered more than an order-of-magnitude larger, 18% decrease in its overall fluorescence in its first second of irradiation as compared to its initial signal, which must be due to immediate surface ablation. Similarly the 50 nA fixed beam suffered a 43% decrease in its overall fluorescence in its first second of irradiation as compared to its initial signal as seen in FIG. 5, and given its deep hole creation in just 33 seconds it can be considered a "fast" ablation.

Figure 7:
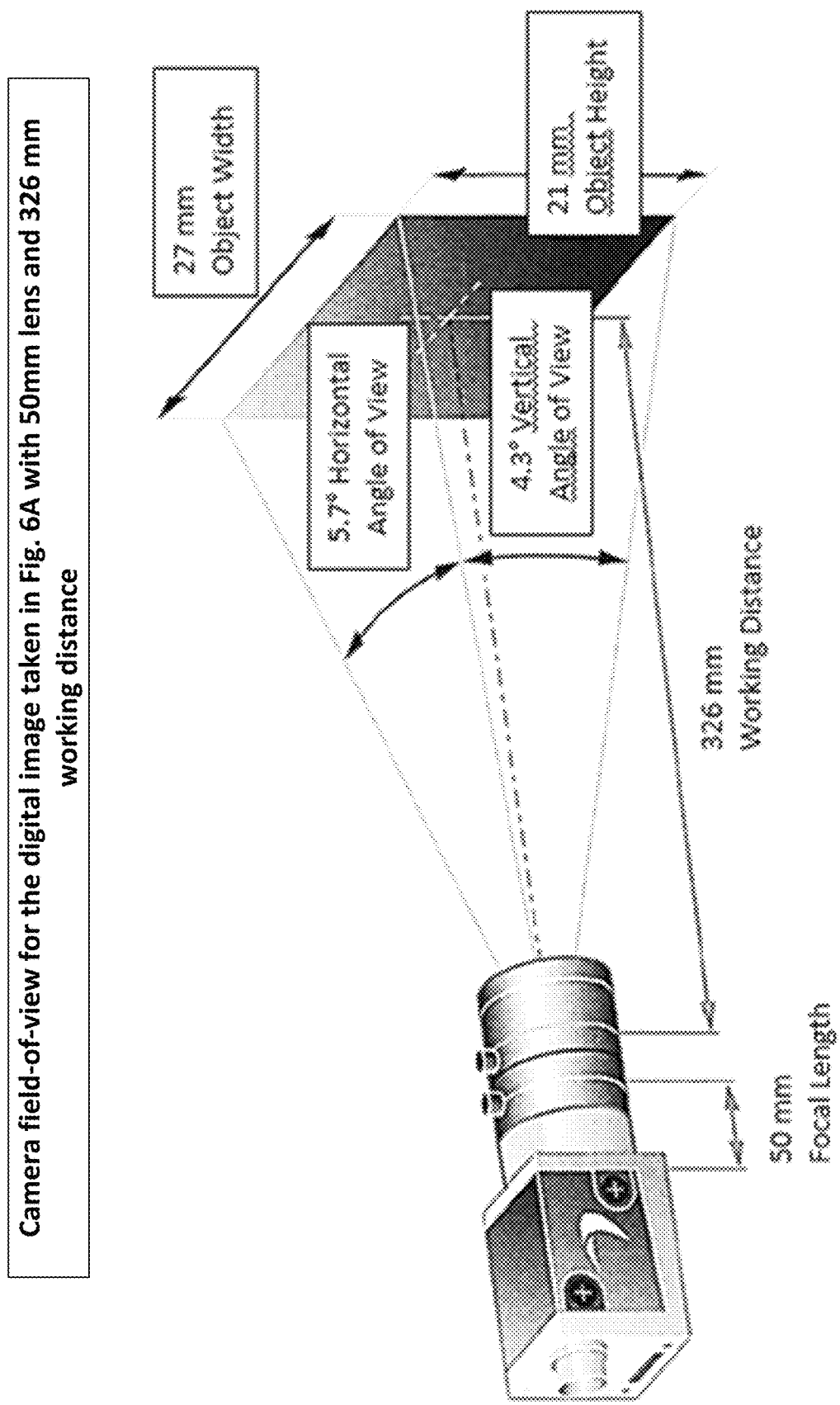
FIG. 7 is a projection of the camera field-of-view for the digital image in FIG. 6A, taken at a working distance of 326 mm in accordance with embodiments.

FIG. 7 is a projection of the camera field-of-view for the digital image in FIG. 6A, taken at a working distance of 326 mm in accordance with embodiments. The camera was a Basler acA720-520 um with a 50 mm FL, f/1.4 lens. As shown in FIG. 6A, images were photographed through a chamber window of the 3.0 MeV proton beam irradiating the 191 μm thick BoPEN scintillator film in real-time, with the camera outside the vacuum chamber at an estimated working distance from the front of the camera lens to the scintillator film of ~326 mm (as shown in FIG. 7).

As disclosed above, the very "first" digital image (1 ms shutter speed) taken within the 1st second of irradiation (i.e., at 2 fps and prior to significant ablation) at a beam current of 10 nA appears in FIG. 6A, which from the measured ablation area of 0.020 cm$^2$ at the top surface of the hole yielded a current density of 500 nA/cm$^2$ corresponding to a dose rate of 92 kGy/sec. The fitted beam profile for the image in FIG. 6A appears in FIG. 6B with a calculated σ of 0.61 mm, and a FWHM of ~1.22 mm, corresponding to a 97% full-bandwidth radius of 1.34 mm (i.e., 2.2σ) with an area of 5.6 mm$^2$. From the previous experimental data of the rapid drop in average fluorescent signal (i.e., 18% decrease within the 1st second of irradiation), it's clear that at this dose rate ablation starts immediately upon beam exposure. However, from the progression of real-time camera fluorescence images over the 66 seconds of beam irradiation, it would appear that the ablation rate was relatively slow compared to that at the 50 nA beam current.

As disclosed above, an incident 5.4 MeV proton beam has adequate energy to pass through the 191 μm thick BoPEN film and exit with a residual energy of 3.26 MeV. However, at 3.0 MeV the proton beam only penetrates approximately 119 μm into the 191 μm thick BoPEN film. If the proton beam current density is sufficient to cause ablation and start "burning a hole" in the BoPEN film, then as the ablation proceeds the beam will penetrate further and further into the film, eventually exiting first at reduced energy and then almost at full energy once the hole has burrowed or punched through. Examination under a microscope confirmed that even at the 50 nA beam current, the ablated hole did not go all the way through the 191 μm thick film during the 33 seconds of beam irradiation, which followed the prior 66 seconds of much slower ablation at 10 nA.

The total estimated beam penetration depth was about 150-160 μm, and encompassed a maximum surface ablation area of ~0.020 cm$^2$, although the hole ellipsoid minor and major axes in the area of deepest penetration at the hole bottom was measured to be much smaller at about 0.4×0.6 mm (0.002 cm$^2$). Based on the ablated hole area surface dimensions, the associated beam current density was 2500 nA/cm$^2$ at 50 nA, corresponding to an accumulated dose of 15 MGy at a dose rate of 460 kGy/sec (see Table 1). At this dose rate, it is clear from the "average pixel signal" in FIG. 5, derived from each 1 ms photo/image at 2 fps, that ablation started immediately upon beam exposure (i.e., within a half-second). This result can be compared to the previous results for the 5.4 MeV proton beam at a current density of 2.4 nA/cm$^2$, in which rad-damage occurred almost three orders-of-magnitude slower as it took 300 seconds for the bulk fluorescence intensity to decrease by 26%.

The ablated area/hole created by the 50 nA beam was elliptically shaped with measured minor and major axes of ~1.4 mm×1.8 mm, corresponding to an equivalent circle with a radius of 0.80 mm and an area of 2.0 mm$^2$. However the Gaussian fit distribution for FIG. 6A, as shown in FIG. 6B, corresponding to the 97% intensity full bandwidth has a beam radius of 2.2σ. This larger fluorescent emission area of 5.6 mm$^2$ associated with the 2.2σ radius encompasses about 97% of the fluorescent signal area shown in FIG. 6A, and extends beyond the ablated hole. The fluorescent ellipsoid minor and major axis dimensions corresponding to the 2.2σ radius of 1.34 mm is 2.34 mm×3.02 mm, and corresponds to the estimated dimensions in FIG. 6A, with the camera image of the ellipsoid area containing ~3,800 pixels. It follows from FIG. 7 that each pixel corresponds to a field-of-view image area of ~38.2 μm×38.2 μm. The Basler acA720-520 um camera used for the FIG. 6A image has a 720×540 pixel CMOS sensor. It also follows that with the 50 mm focal length lens employed, the working distance ("WD") from the front of the lens to the scintillator was about 326 mm, with the sensor field-of-view being 27 mm×21 mm as shown in FIG. 7.

The maximum beam current and minimum beam radius in the vacuum beamline pipe of a 250 MeV proton accelerator is typically ~800 nA for a superconducting cyclotron with approximately a 1 mm beam radius. The associated beam current density is ~25,000 nA/cm$^2$. Under such conditions with a 25-50 μm thick BoPEN film scintillator, the dose rate could be 100-200 kGy/s, causing significant ablation of the BoPEN film and resulting in hole-burning within a minute or so. Good practice would dictate that the film radiation exposure in any one spot be limited to ten seconds or less.

For the above case of a 100-200 kGy/s dose rate, embodiments include a 5-way or 6-way-cross vacuum chamber that is designed to allow the BoPEN scintillator to be moved out of the beam within seconds after being moved into the beam to capture the required beam images. The proton beam image in FIG. 6A at a dose rate of 92 kGy/s provides an example of what such an image might look like. Although the BoPEN thickness in FIG. 6A is 191 μm, as compared to only 25-50 μm in the 5-way or 6-way-cross, the camera lens can be much closer to the scintillator in the cross than the 326 mm distance in FIGS. 6A, 6B and 7, so the solid collection angle is much greater to collect a larger fraction of the emitted photons from the thinner BoPEN film, and in addition a better light-sensitive camera could be employed than used in FIGS. 6A, 6B.

The low-energy proton beam tests at 3.0 MeV and 5.4 MeV for the 191 μm thick BoPEN film scintillator as summarized in Table 1 above covered a matrix spanning roughly three (3) orders-of-magnitude for the critical parameters of beam current density, absorbed dose and dose rate. The results of the described accelerated test program demonstrate the exceptional performance to be realized from the broad family of disclosed embodiments that have led to a wide variety of UFT (ultra-fast transmissive) high-resolution detection system embodiments for real-time monitoring of ionizing particle and photon beams. The targeted applications for the described embodiments below, include not only proton therapy, but all other types of particle and photon external beam radiation therapy ("EBRT"), as well as beam monitors for industrial and research accelerators including those used in nuclear and high energy physics, etc.

With regard to proton therapy, embodiments demonstrate an unexpected result that 5 minutes of testing at a beam particle energy of 5.4 MeV, a beam current density of 2.4 nA/cm$^2$, and an irradiation dose rate of 200 Gy/s will not cause visual damage to the BoPEN scintillator, but would be roughly equivalent to the dose incurred in treating ~30,000 patients assuming a conventional dose of 2 Gy per patient, or 3,000 patients at a FLASH dose of 20 Gy per patient. Thus radiation damage to a BoPEN film scintillator is not a significant issue and can be readily handled as disclosed below.

Given the previous estimate of 0.04% to 0.07% maximum accumulated scintillator radiation damage per week in a "typical" treatment room facility seeing 30 patients per day, embodiments have a need to advance a fresh area of scintillator film to the scintillator isocenter on a bi-weekly, monthly or possibly even quarterly basis; the latter period corresponding to a maximum estimated fluorescence loss of ~0.9%. Therefore, as a practical matter it appears that having to measure the daily or weekly rad-damage contribution to scintillator non-uniformity can likely be ignored due to it being inconsequential, which has important implications. Specifically, calibration efforts in embodiments can be shifted to measuring and quantifying the other parameters that have to be monitored for achieving and maintaining an integrated system accuracy of 1% or better on a per patient daily basis. It follows that given the very small amount of rad-damage incurring on a weekly basis, a strategy of advancing the scintillator film, either by unwinding it from a spool (e.g., similar to advancing 35 mm film frame-by-frame in a camera) or by pushing a frame with the film mounted to it by a few centimeters on a periodic basis (e.g. weekly, biweekly, monthly, etc.) could be implemented via a variety of embodiments as disclosed below.

Figure 8A:
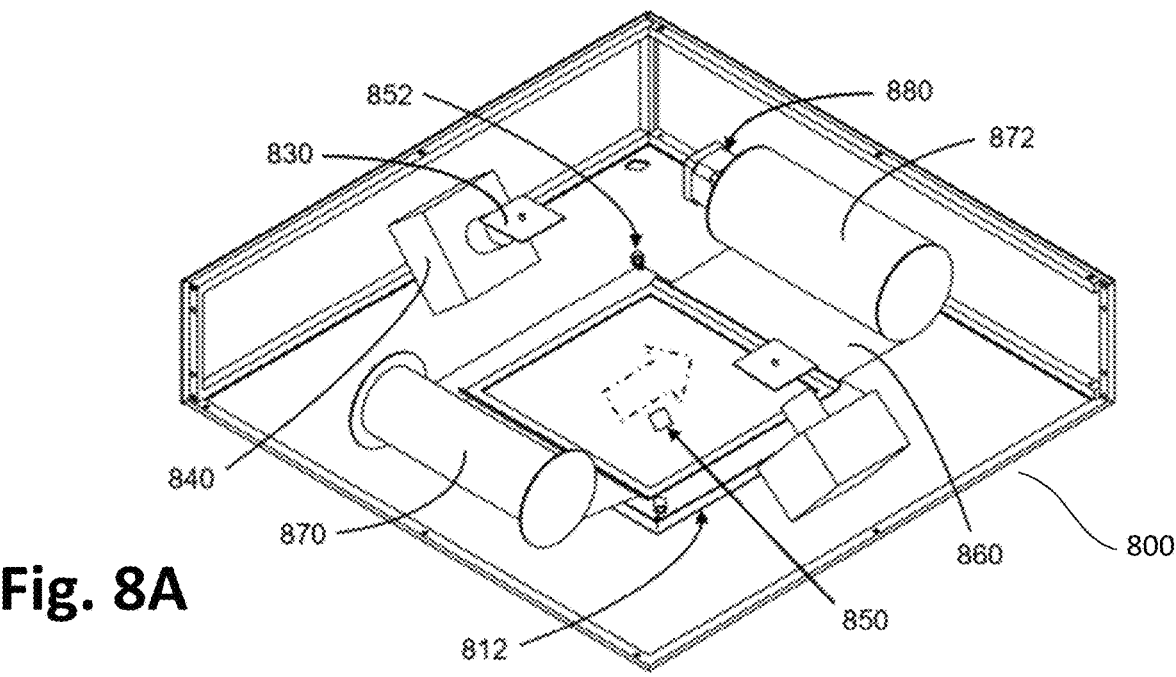
FIGS. 8A-C illustrate a system that includes a two camera, single scintillator beam monitor in a light-tight enclosure employing a rolled scintillator spool configuration in accordance to embodiments.
Figure 8B:
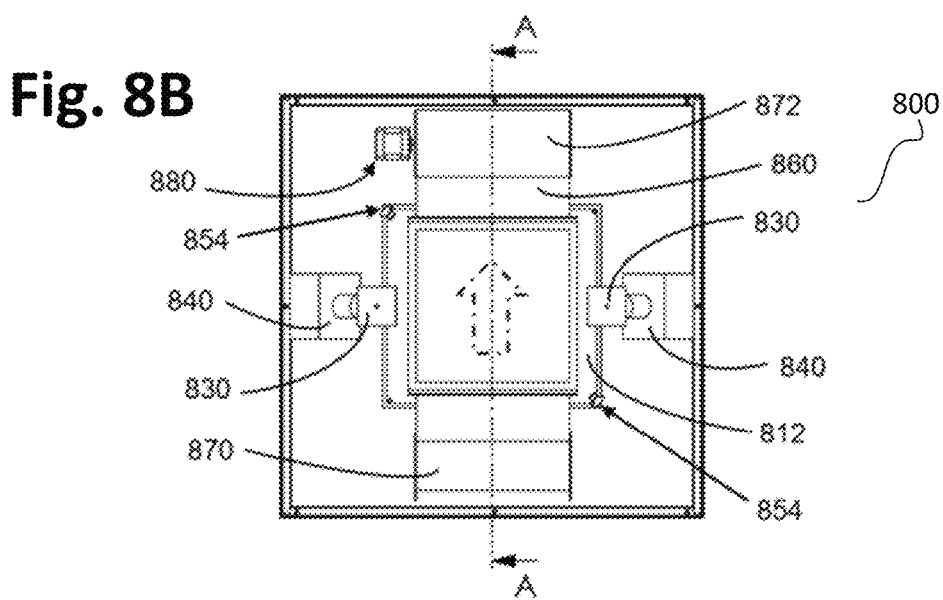
Figure 8C:
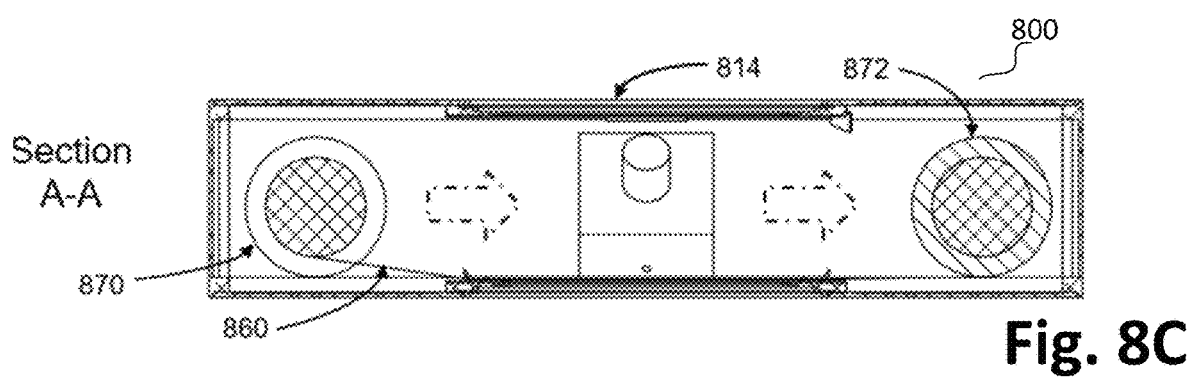

FIGS. 8A-C illustrate a system 800 that includes a two camera 840, single scintillator beam monitor in a light-tight enclosure employing a rolled scintillator spool configuration in accordance with embodiments. FIG. 8A is a perspective view with the top cover plate removed, FIG. 8B is a top view, and FIG. 8C is a section A-A view. The dotted arrows in all three figures show the direction of film movement from the feed roll to the take-up roll.

System 800 includes a two mirror 830, folded optical configuration which minimizes the light-tight enclosure depth/thickness while incorporating a mechanism for advancing the scintillator film 860 to minimize or eliminate having to correct for scintillator radiation damage. A relatively thick scintillator film such as 125-250 μm thick BoPEN film (i.e., 5-10 mils) is wound onto a small diameter (e.g., 2.5") feeder spool 870 to an outer diameter ("OD") that fits within the light-tight enclosure (e.g., ~4"). This film could be of any width (e.g., 25-45 cm), and could contain a total length of about 20-25 meters of 191 μm BoPEN scintillator. In this embodiment, film 860 would be pulled across an active window area 812 onto a suitable take-up spool 872, and advanced by a stepper motor 880 that rotates the take-up spool spindle as required. An ultra-thin dark colored exit window 814, such as 15 to 25 μm thick black aluminum foil, is shown in FIG. 8C, while one of the UV-LED sources 850 and UV-photodiodes 852 are shown in FIG. 8A, with the two UV-LED/UV-photocell combinations 854 shown in FIG. 8B.

Figure 9A:
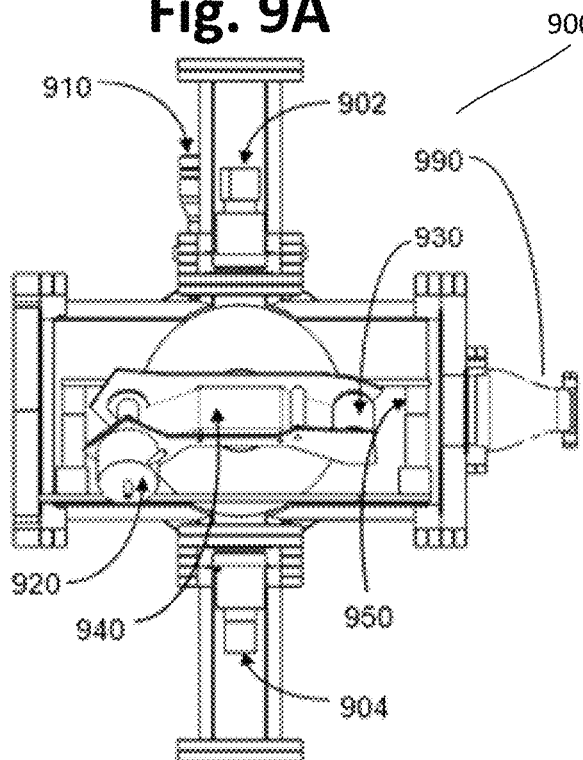
FIGS. 9A-D illustrate a system that includes a two camera, single scintillator roll film beam monitor with linear translation of the scintillator spool system in a 6-way-cross vacuum chamber in accordance with embodiments.
Figure 9B:
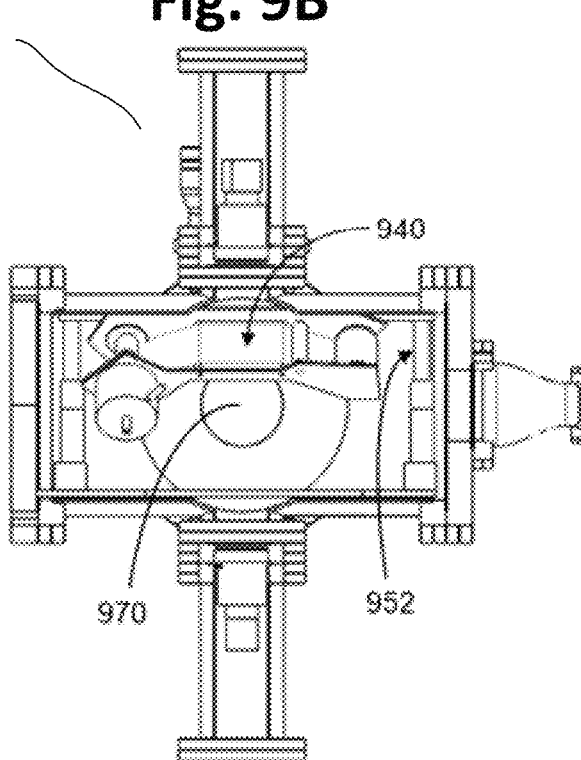
Figure 9C:
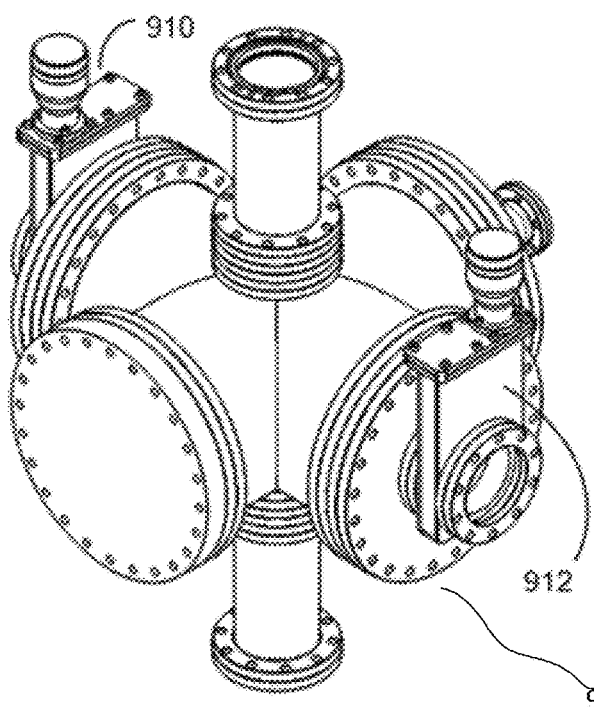
Figure 9D:
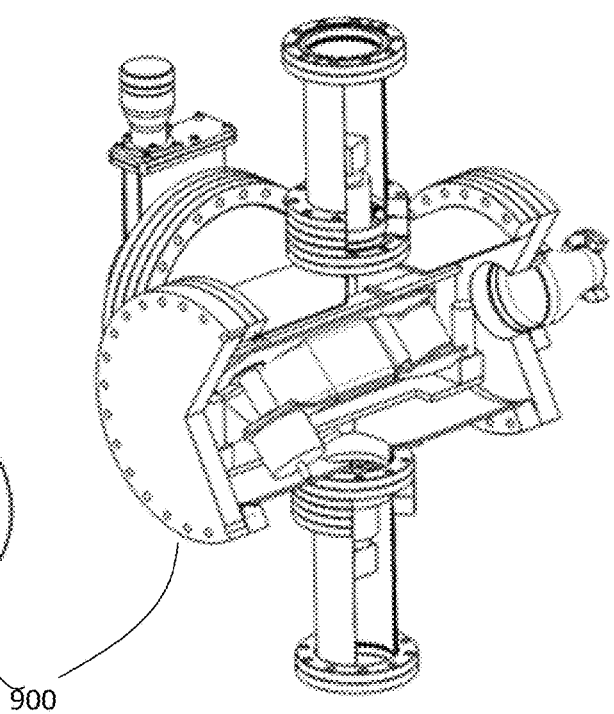

FIGS. 9A-D illustrate a system 900 that includes a two camera, single scintillator roll film beam monitor with linear translation of the scintillator spool system in a 6-way-cross vacuum chamber in accordance with embodiments. FIG. 9A is a cross-sectional view looking from the front with the scintillator film 940 positioned in the center of the beam path by linear position translators 950 and with cameras 902 and 904 in the top and bottom arms to achieve enhanced beam image resolution. The scintillator film is wound onto and stored on a small diameter feeder spool 930 and pulled across the beam axis transit area 970 (in FIG. 9B) onto a suitable take-up spool advanced by an internal (i.e. vacuum compatible) stepper motor 920 that rotates the take-up spool spindle as required. Also shown is a reducer nipple 990 that can connect to an external pressure bleed and/or vacuum line (not shown) to be used to break and then re-establish the beam monitor vacuum during system isolation for scintillator replacement (see FIG. 9C description below). FIG. 9B is the same cross-sectional view but with the scintillator film 940 translated vertically up and out of the beamline path region 970, by the linear position translators in their extended position 952. FIG. 9C is a perspective view of the closed system showing all 6 arms including the beam entrance and exit gate valves 912 and 910 that can be shut to isolate the beam monitor system and allow scintillator roll access and replacement without breaking beamline vacuum. FIG. 9D is a cross-sectional perspective view of FIG. 9C showing the ~45° scintillator film angle with respect to both the beam angle of incidence and the viewing angle for both camera systems (also visible in FIG. 9A). It is noted that the 6-way-cross in FIGS. 9A-D is shown like all of the other 6-way-crosses with each arm at a 90° angle with respect to its nearest adjacent arm. However, to improve the photon collection angle/efficiency, one or both camera arms can be constructed at approximately a 45° angle with respect to the main body of the 6-way-cross housing the scintillator film so that the camera lens optical axis is at approximately a 90° angle with respect to the scintillator film plane.

Figure 10A:
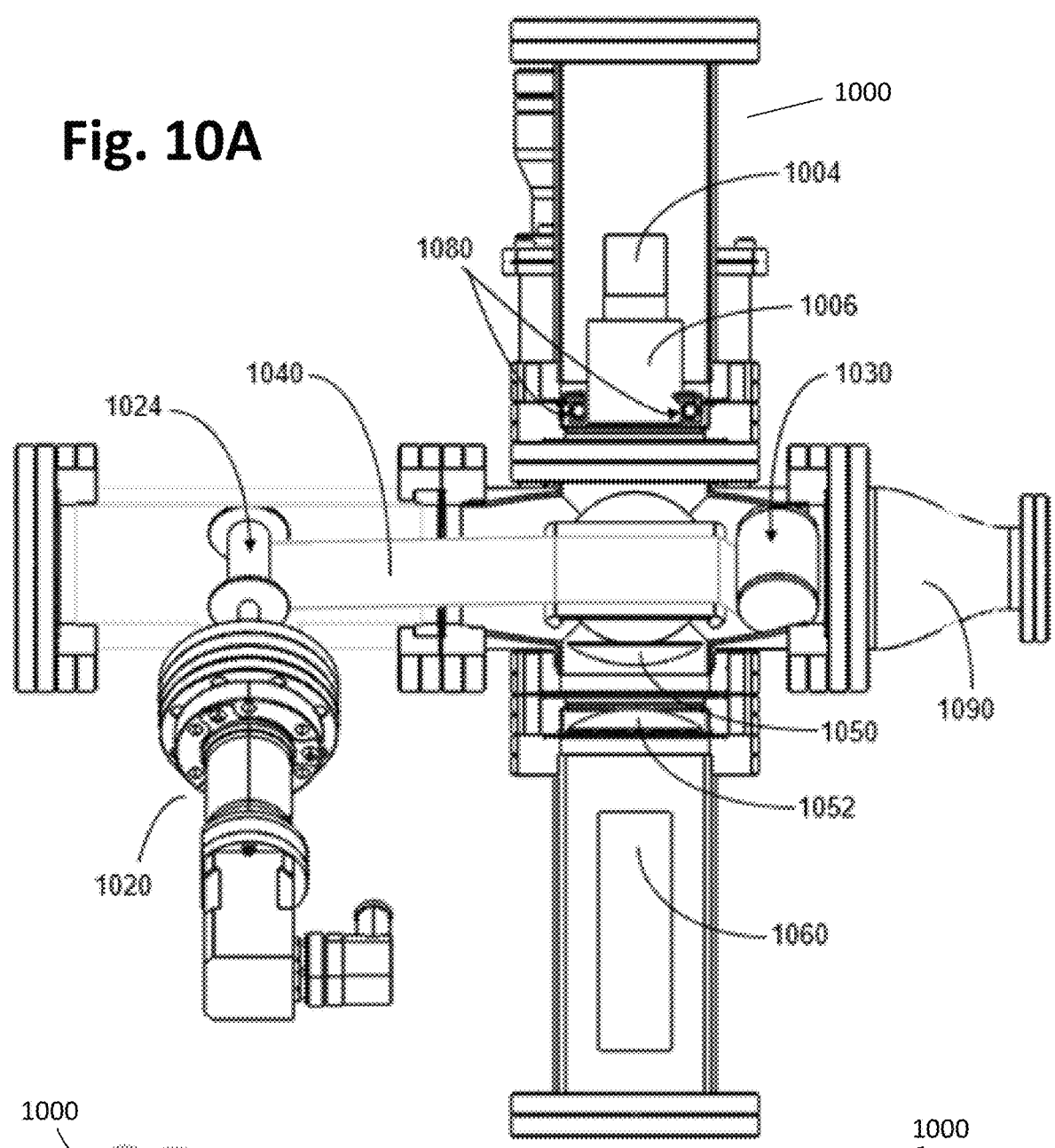
FIGS. 10A-C illustrate a system that includes a roll film scintillator beam monitor in a smaller 6-way-cross vacuum chamber without linear translation capability in accordance with embodiments.
Figure 10B:
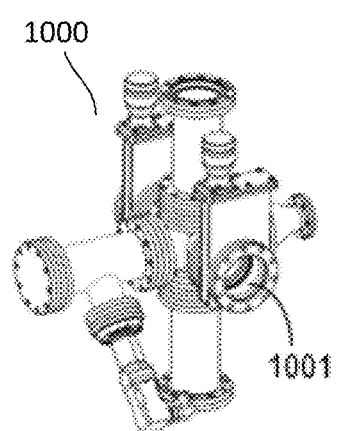
Figure 10C:
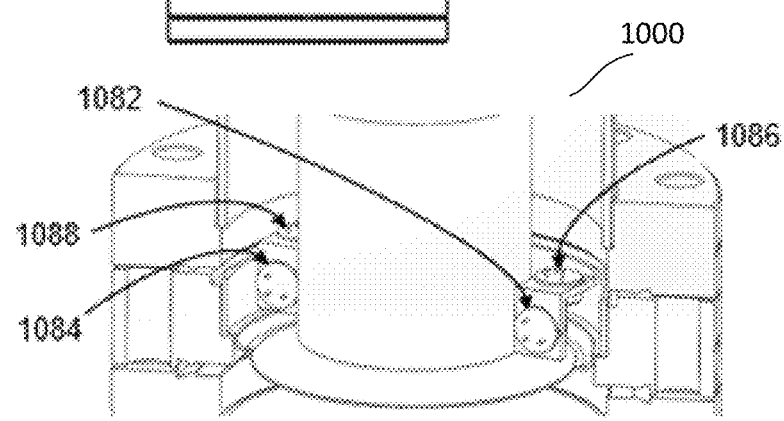

FIGS. 10A-C illustrate a system 1000 that includes a roll film scintillator beam monitor in a smaller 6-way-cross vacuum chamber without linear translation capability in accordance with embodiments. FIG. 10A is a cross-sectional view from the front showing a camera 1004 and camera lens 1006 in the top arm and a PMT 1060 in the bottom arm; the latter for fast timing applications with enhanced light collection capability via a set of condensing lenses with the top lens 1050 located in the vacuum chamber just below the scintillator film 1040 and the bottom lens 1052 located just above the PMT 1060 in an ambient air environment. As in FIG. 9A, the scintillator film 1040 in FIG. 10A is at approximately a 45° angle with respect to the beam, camera and PMT. FIG. 10A shows the two UV-LED/UV-photodiode combination assemblies 1080 on opposite sides of the camera lens 1006. The scintillator film is wound onto and stored on a small diameter feeder spool 1030 and pulled across the beam axis transit region onto a suitable take-up spool 1024 advanced by an external stepper motor assembly 1020 that rotates the take-up spool spindle as required. FIG. 10B is a perspective view showing all 6 arms including the beam entrance 1001 and exit gate valves that allow system vacuum isolation and subsequent pressurization through the reducer nipple 1090 (in FIG. 10A) for scintillator roll replacement without breaking beamline vacuum. FIG. 10C is a close-up cross-sectional view showing the two UV-LEDs 1086 and 1088, and two UV-photodiodes 1082 and 1084 on opposite sides of the camera lens.

Figure 11A:
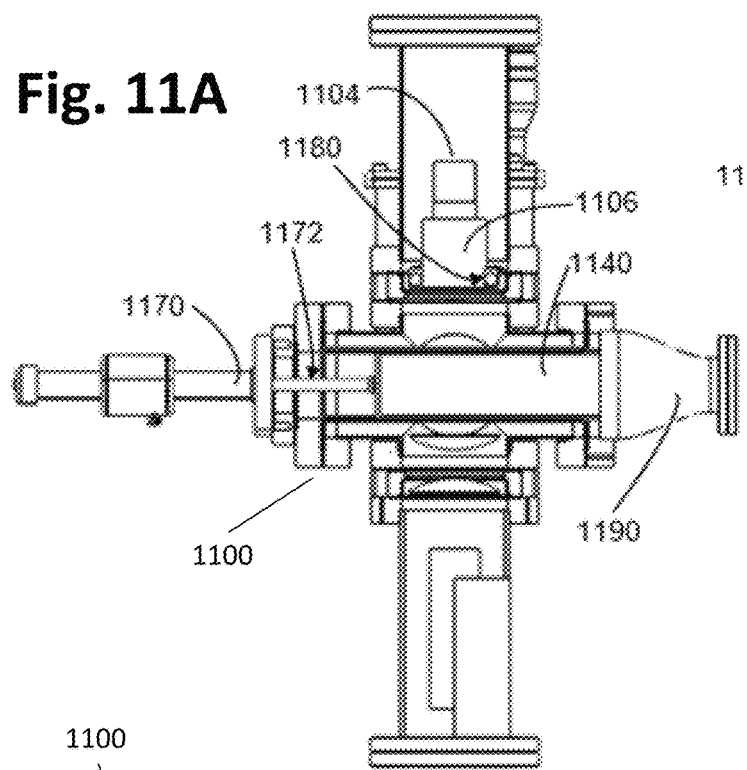
FIGS. 11A-D illustrate a system that includes a single scintillator-frame beam monitor in 6-way-cross vacuum chamber in accordance with embodiments.
Figure 11B:
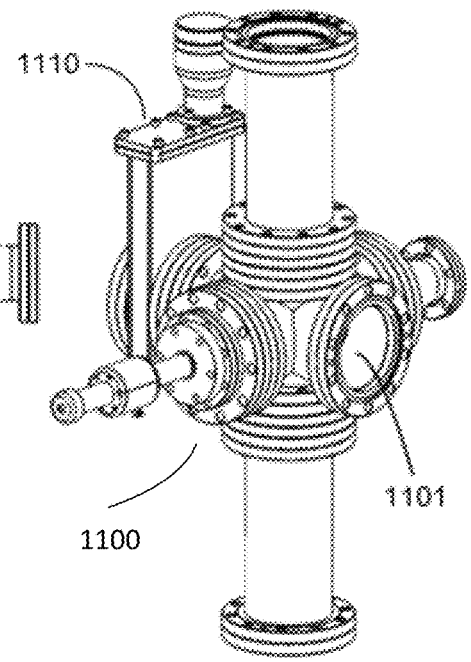
Figure 11C:
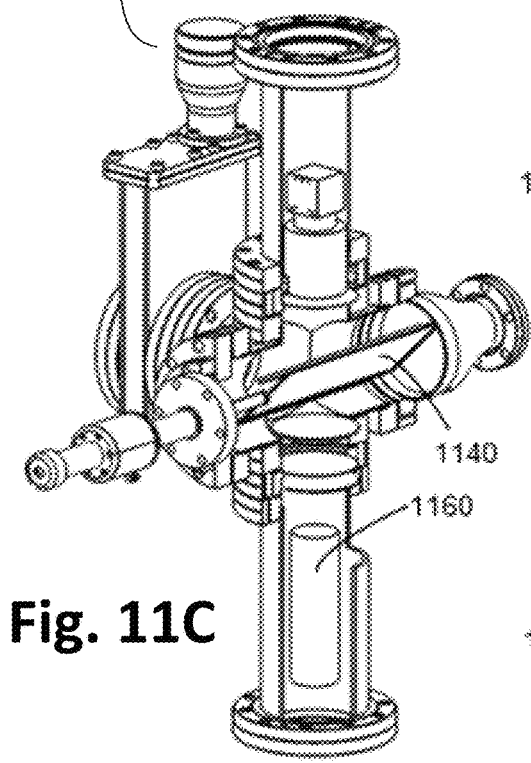
Figure 11D:
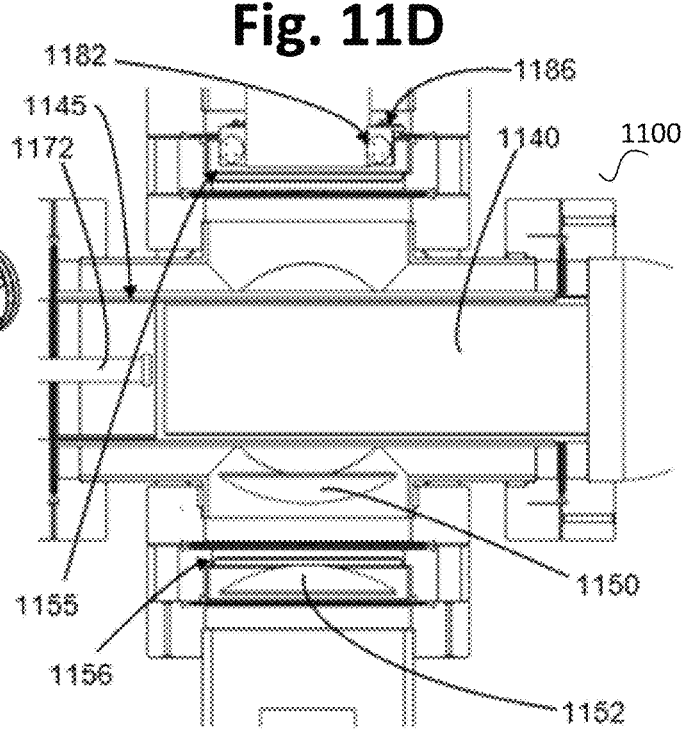

FIGS. 11A-D illustrate a system 1100 that includes a single scintillator-frame beam monitor in 6-way-cross vacuum chamber in accordance with embodiments. FIG. 11A is a cross-sectional view showing 4 of the 6 arms as seen from the front with a push-pull linear positioner on the left and a vacuum reducer nipple on the right. FIG. 11B is a perspective view showing all 6 arms of the closed system including a gate valve attached to the beam exit flange. FIG. 11C is a cross-sectional perspective view showing the tilted scintillator frame at approximately a 45° angle to the beam, camera and PMT. FIG. 11D is a close-up sectional view of the beam cross center showing a first condensing lens in the chamber vacuum region with the second condensing lens just below the viewport window in front of the PMT in an ambient air environment. Also just above the viewport UV window for the camera, on either side of the lens barrel are a pair of UV-LEDs and associated UV-photodiodes.

Figure 12A:
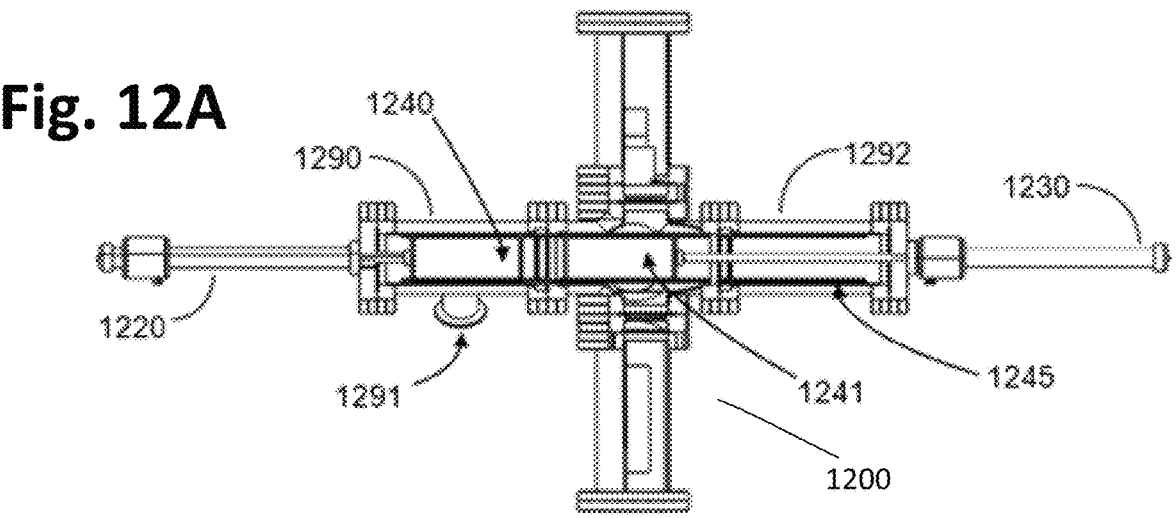
FIGS. 12A-C illustrate a system that includes a double scintillator-frame beam monitor in a 6-way-cross vacuum chamber in accordance with embodiments.
Figure 12B:
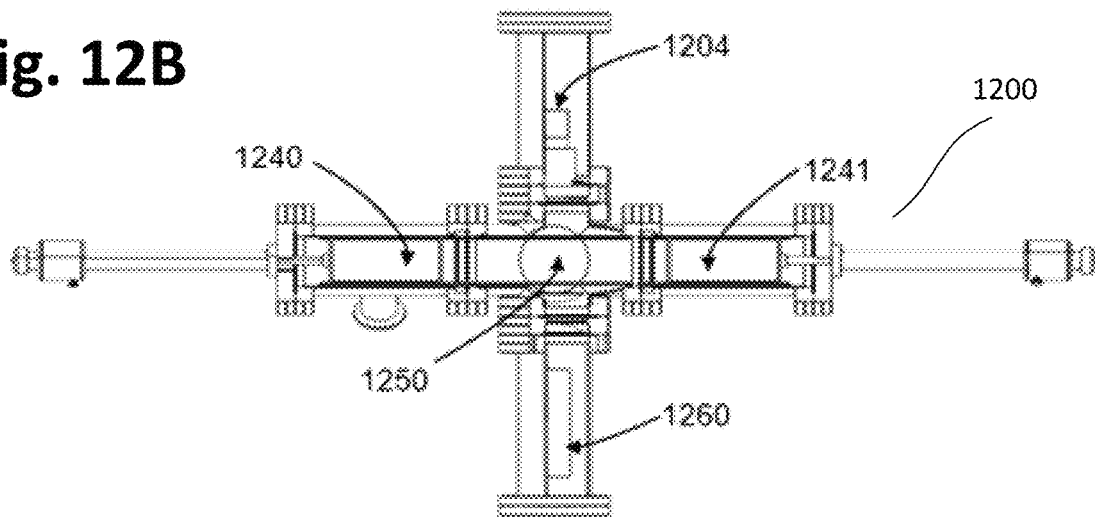
Figure 12C:
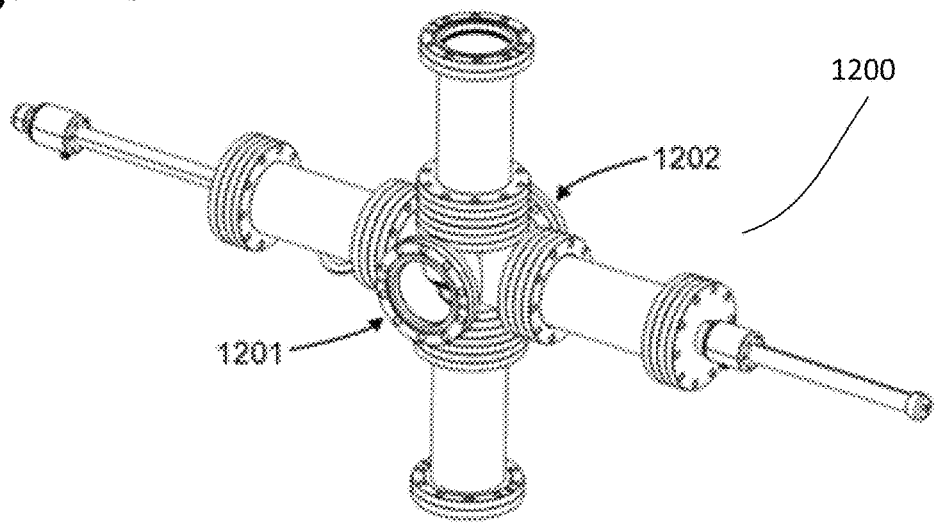

FIGS. 12A-C illustrate a system 1200 that includes a double scintillator-frame beam monitor in a 6-way-cross vacuum chamber in accordance with embodiments. FIG. 12A is a cross-sectional view showing 4 of the 6 arms as seen from the front, with a full-nipple and push-pull linear positioner added to each side as compared to only one side in FIGS. 11A-D. FIG. 12A shows one scintillator-frame on the left side with a second scintillator-frame mostly on the left side but covering the beam center. FIG. 12B is a cross-sectional view showing one scintillator-frame in each nipple with no scintillator in the beam center region. FIG. 12C is a perspective view of the closed 6-way-cross vacuum chamber. In system 1200, the scintillator-frame is at about a 45° angle with respect to the beam, camera and PMT.

Figure 13A:
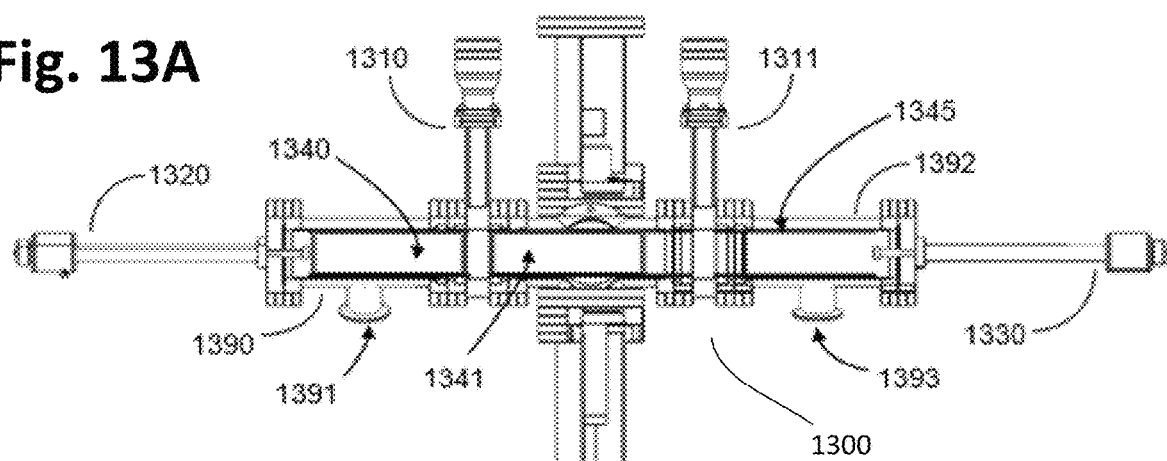
FIGS. 13A-C illustrate a system that includes a double scintillator-frame beam monitor in a 6-way-cross load-lock vacuum chamber in accordance with embodiments.
Figure 13B:
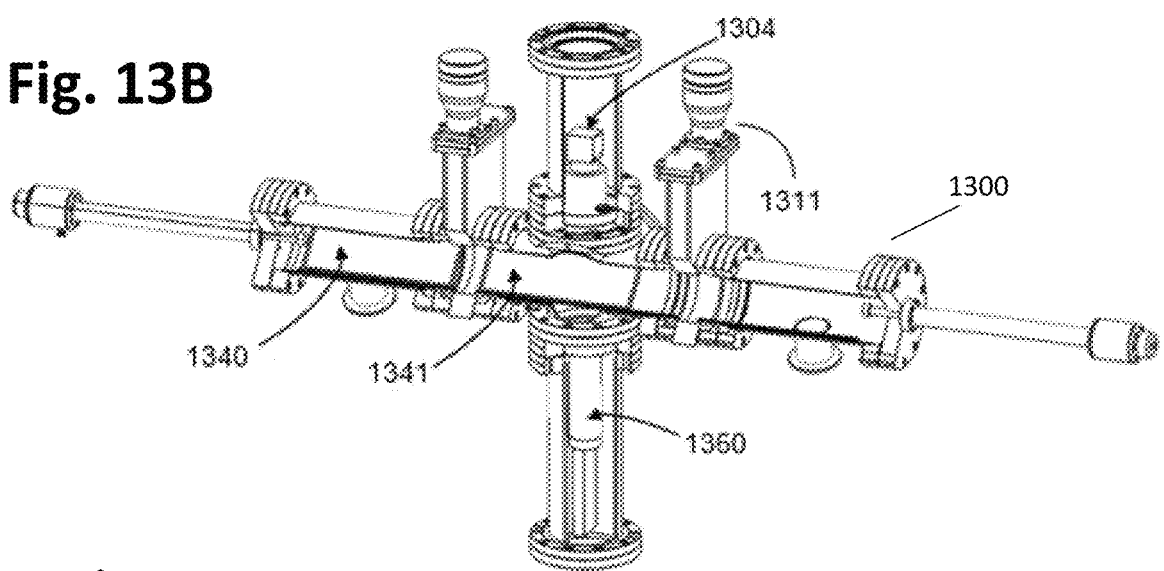
Figure 13C:
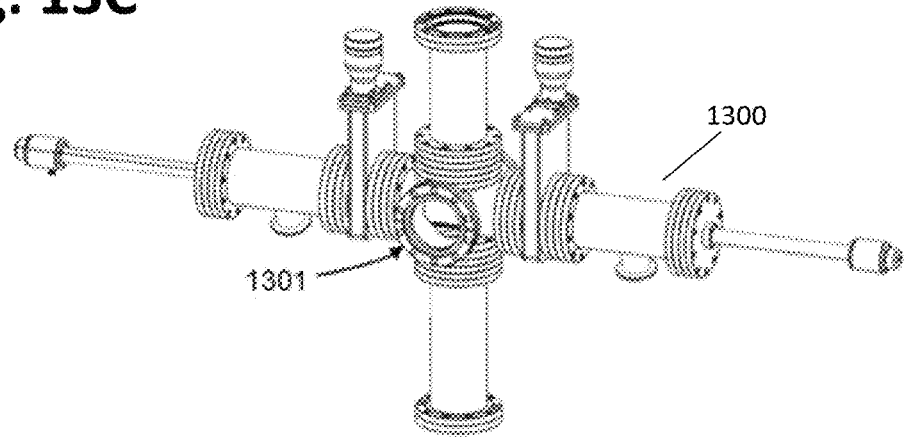

FIGS. 13A-C illustrate a system 1300 that includes a double scintillator-frame beam monitor in a 6-way-cross load-lock vacuum chamber similar to FIGS. 12A-C, but with the addition of two gate valves, each positioned between the 6-way-cross body and the added reducer tees which have replaced the full-nipples in FIG. 12 in accordance with embodiments. The added gate valves convert this structure into a load-lock vacuum chamber, which allows scintillator replacement without breaking the system vacuum. FIG. 13A is a cross-sectional view (similar to FIG. 12A) showing 4 of the 6 arms as seen from the front. FIG. 13B is a cross-sectional perspective view that shows the approximately 45° scintillator-frame angle with respect to the beam, camera and PMT. FIG. 13C is a perspective view of the closed 6-way-cross load-lock vacuum chamber.

Figure 27A:
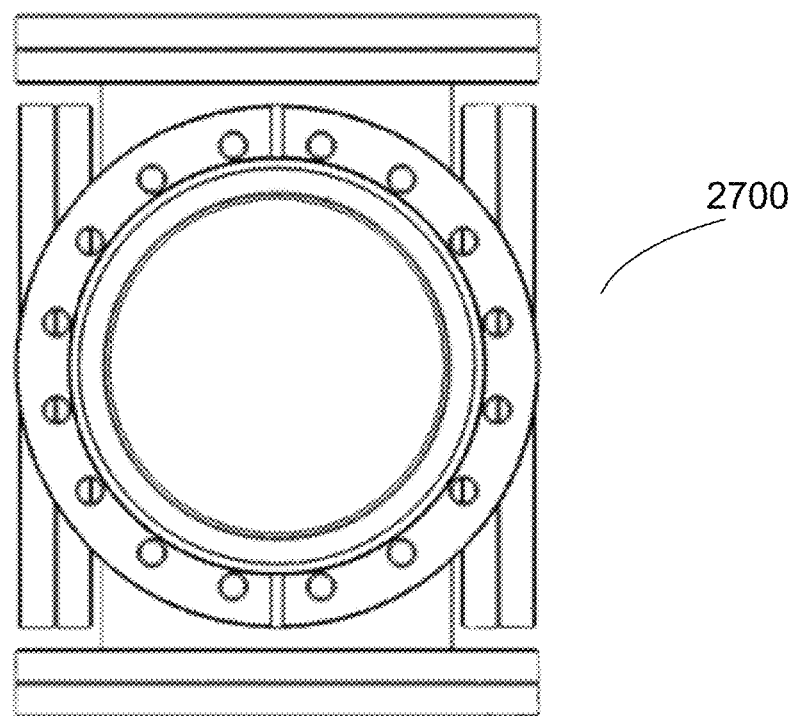
FIGS. 27A-B illustrate the open central structure of a reduced/shortened 4" O.D. tube, 6-way-cross with 6" diameter CF-flanges modified such that the total beam entrance-to-exit length is 5.9" in accordance to vacuum chamber embodiments.
Figure 27B:
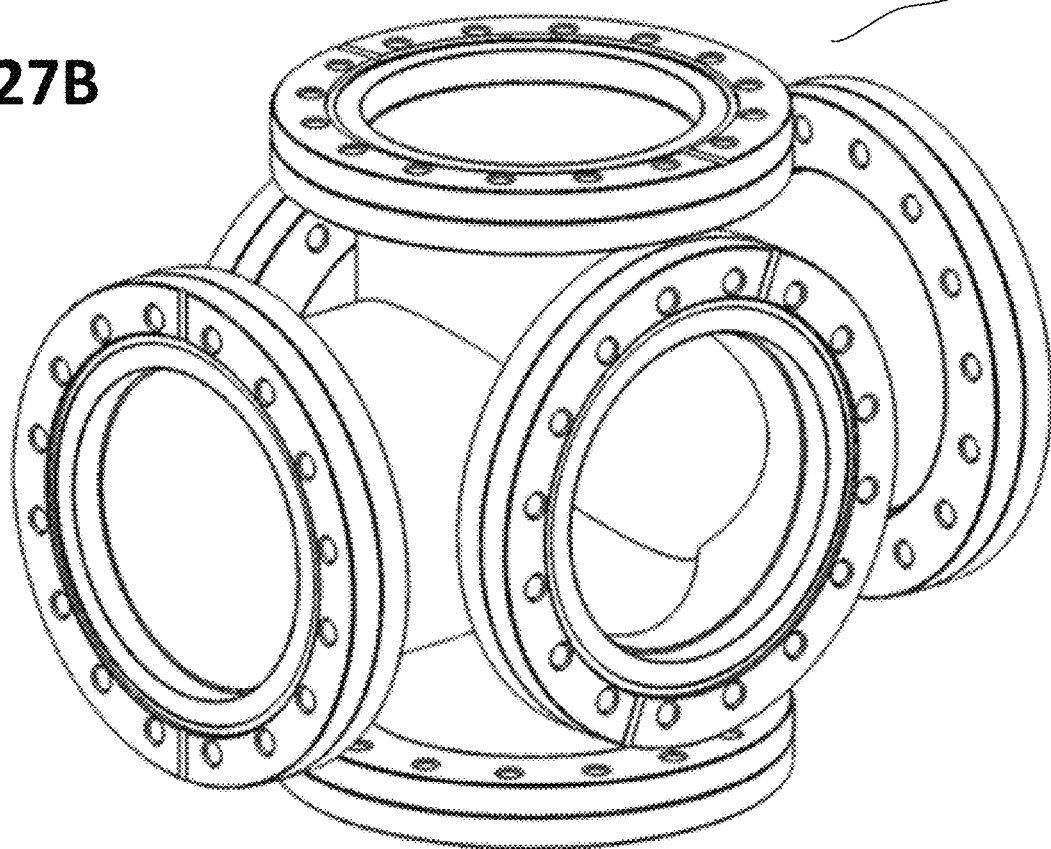

FIGS. 9-13 are based on "off-the-shelf" 6-way-cross configurations that have been modified such that the inner flanges associated with the two vertical tubes/arms as seen in FIGS. 9-13 are reduced or shortened to the minimum length required to weld each vertical flange to the cross body. The purpose of this modification is to position the cameras and/or PMTs as close as possible to the beamline axis/cross-center to improve the photon collection efficiency. However for some applications it is more important that the total length of the cross from the entrance-to-exit flange be minimized, and for such cases the two horizontal tubes/arms along the beam axis are shortened to the minimum stub size required to weld each flange to the cross body. For example, in the case of a beam monitor based on a 4" O.D. tube system with 6" diameter CF-flanges, the total length of the beam monitor including flanges from end-to-end can be reduced to under 6". FIGS. 27A-B illustrate a system 2700 that includes both a side view (FIG. 27A) and perspective view (FIG. 27B) of the open central structure of the above reduced/shortened 4" O.D. tube, 6-way-cross with 6" diameter CF-flanges modified such that the total beam entrance-to-exit length is ≤5.9" in accordance to vacuum chamber embodiments. The 4" tubes that connect to the top and bottom 6" CF-flanges that connect to the viewport windows, and subsequently to the full nipples that accommodate the camera and PMT, are also shortened such that the total end-to-end length for these two flanges is ≤7.9" in accordance to embodiments. Depending upon the application requirements, the described priority can always be changed such that if the 4" O.D. tube, 6-way-cross embodiment shown in FIGS. 27A-B is rotated by 90 degrees, then the end-to-end length for the two 6" CF-flanges to the camera and PMT viewport windows would be ≤5.9" while the minimum total beam entrance-to-exit length would be ≤7.9" in accordance to embodiments.

FIGS. 14A-D illustrate a system 1400 that includes a two camera, two mirror, full-size single scintillator/window module beam monitor in a slim light-tight enclosure in accordance with embodiments. In one embodiment a "slim" light-tight enclosure is 5" thick or less; however, depending upon the patient size requirements, scintillator dimensions, and image spatial and positional resolution specifications, the thickness can typically vary over a range from about 3" to 7". FIG. 14A is a perspective view of the components of a "drop-in" window/scintillator frame module. FIG. 14B shows how the window/scintillator frame module drops into one of the cover plate pockets. FIG. 14C is a perspective drawing of the two camera, single scintillator beam monitor enclosure with the top cover plate removed and positioned above the main structure. FIG. 14D is a cross-sectional view of the light-tight enclosure with drop-in ultra-thin window 1422 and window/scintillator 1460 modules, showing the folded optical design of camera, mirror and scintillator, and minimum scintillator field-of-view by camera-lens system on right side (i.e., within dotted line cone). Also shown in FIGS. 14C and 14D are a UV-LED source and UV-photodiode for internal calibration.

FIGS. 15A-C illustrate a system 1500 that includes a one camera, one mirror, half-size rectangular single scintillator beam monitor in a slim light-tight enclosure version of the embodiments shown in FIGS. 14C-D in accordance with embodiments. FIG. 15A is a perspective view assembly drawing showing the camera 1540, mirror 1530, ultra-thin window 1522, window/scintillator module 1560, UV-LED source 1550, UV-photodiode 1552, and the box construction with window cover plate 1520 and window/scintillator cover plate 1570 based on an internal frame structure. The actual enclosure shape and construction can vary and does not have to be rectangular (e.g. can be cylindrical). FIG. 15B is a cross-sectional view of the light-tight enclosure showing all of the basic described components. FIG. 15C is a perspective view of the enclosed system.

FIGS. 16A-C illustrate a system 1600 that includes a three camera version of the embodiments shown in FIGS. 15A-C in accordance with embodiments. The additional two side cameras do not have to be identical to the single top camera and can be selected for improved light-sensitivity, faster frame rates, and/or higher pixel resolution. FIG. 16A is a perspective view assembly drawing showing the three cameras 1640, 1644 and 1646, associated mirrors 1630, 1634 and 1636, ultra-thin window 1622, and window/scintillator module 1660, based on an internal frame structure. The actual enclosure shape and construction can vary and does not have to be rectangular (e.g. can be cylindrical). FIG. 16B is a cross-sectional view of the light-tight enclosure showing all of the basic described components. FIG. 16C is a perspective view of the enclosed system.

Figure 17A:
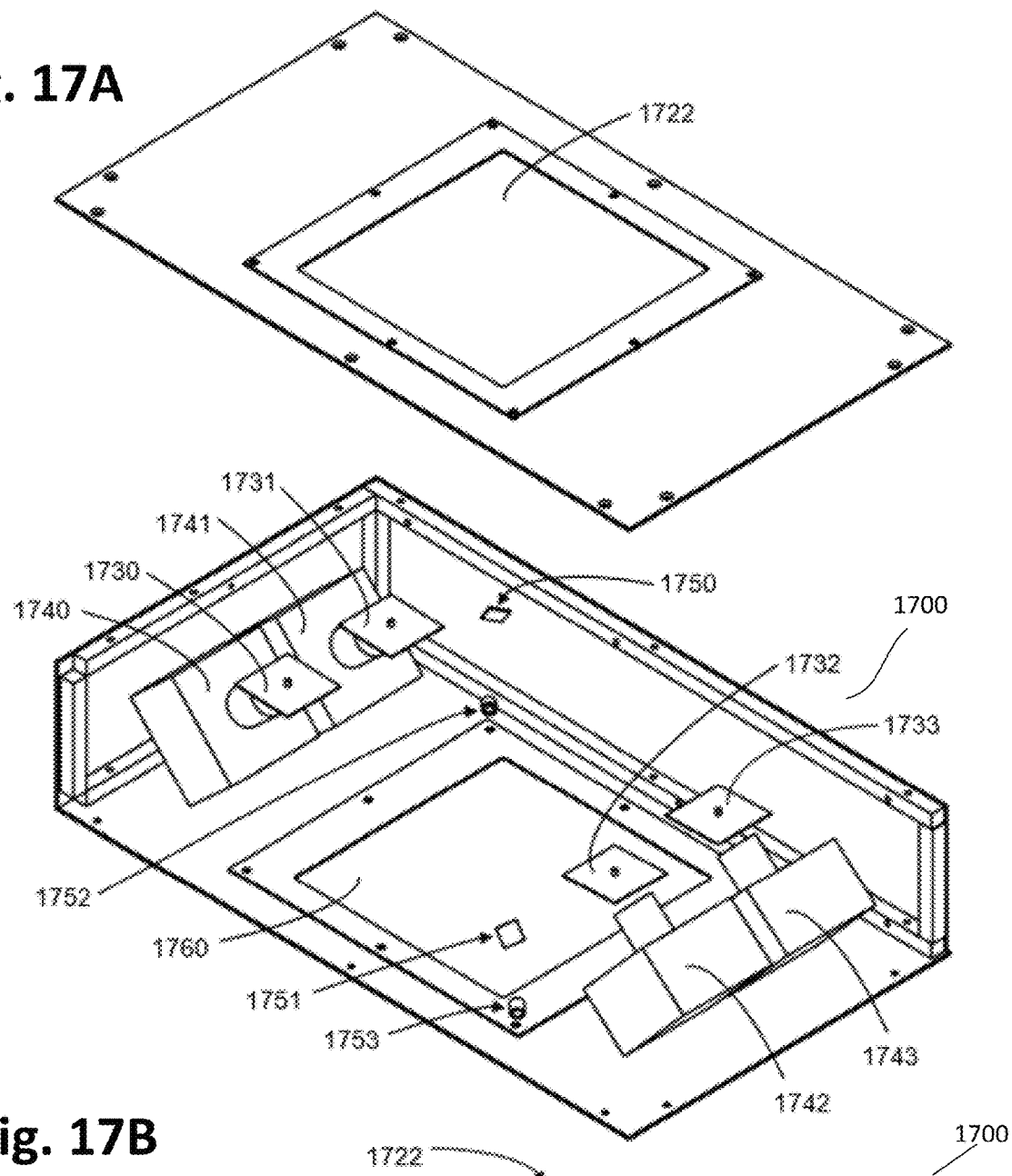
FIGS. 17A-B illustrate a system that includes a four camera version of the embodiments shown in FIGS. 14A-D for the full-size single scintillator-frame beam monitor in accordance with embodiments.
Figure 17B:
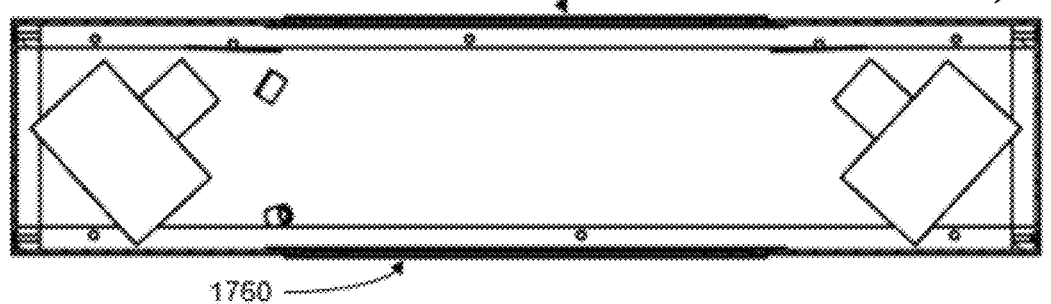

FIGS. 17A-B illustrate a system 1700 that includes a four camera version of the embodiments shown in FIGS. 14A-D for the full-size single scintillator-frame beam monitor with folded-optics in accordance with embodiments. The two additional cameras allow the field-of-view of each camera to be appropriately reduced to a scintillator quadrant, resulting most likely in selection of a different camera or different lens than in FIG. 14 for improved light-sensitivity, faster frame rates, and/or higher pixel resolution. FIG. 17A is a perspective view assembly drawing showing the four cameras 1740, 1741, 1742 and 1743, associated mirrors 1730, 1731, 1732 and 1733, ultra-thin window 1722, UV-LED sources 1750 and 1751, associated UV-photodiodes 1752 and 1753, and window/scintillator module 1760, based on an internal frame structure. The actual enclosure shape and construction can vary and does not have to be rectangular (e.g. can be cylindrical). FIG. 17B is a cross-sectional view of the light-tight enclosure showing all of the basic described components.

Figure 18A:
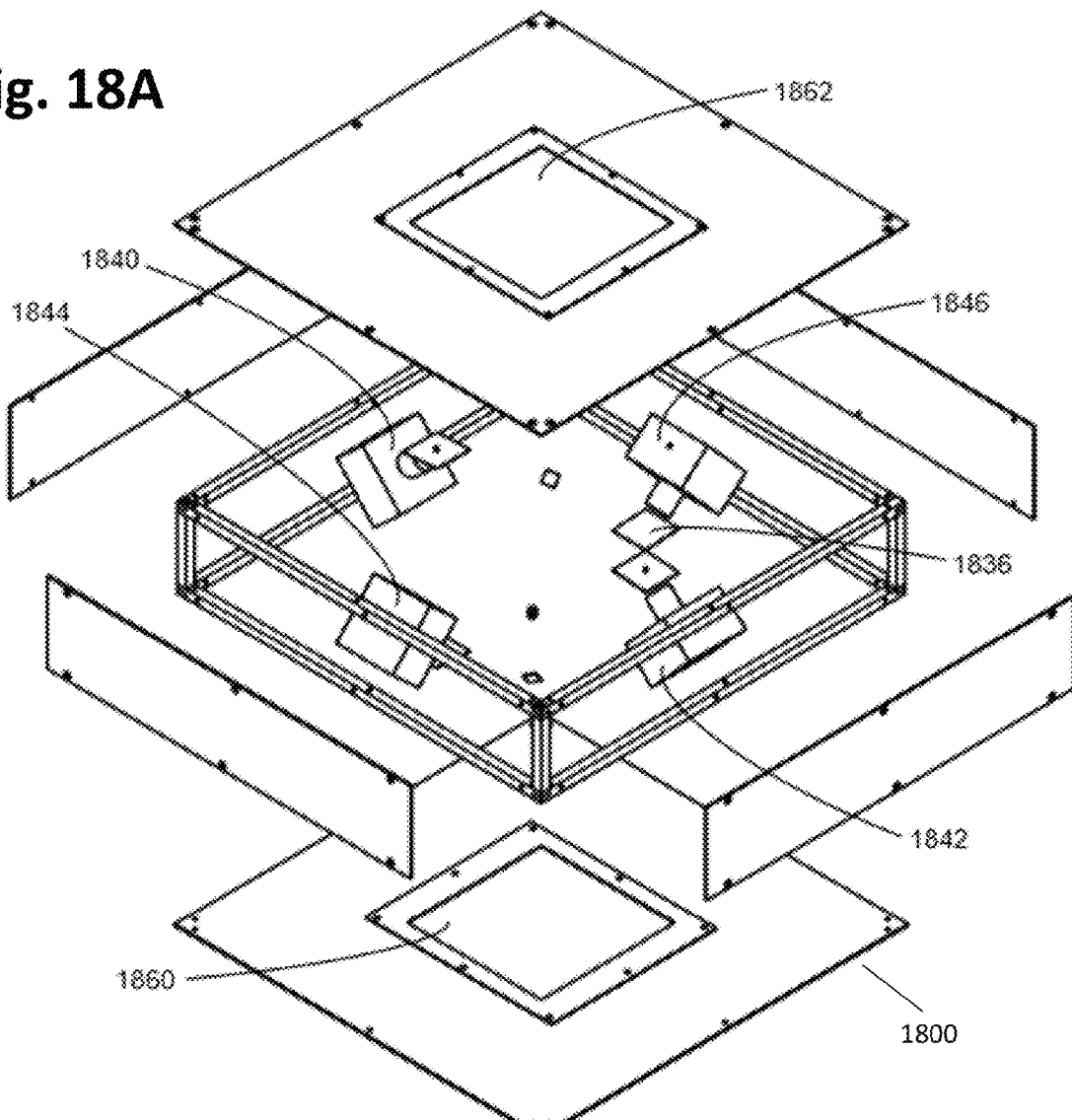
FIGS. 18A-B illustrate a system that includes a four camera, full-size double window/scintillator module beam monitor in a light-tight slim enclosure in accordance with embodiments.
Figure 18B:
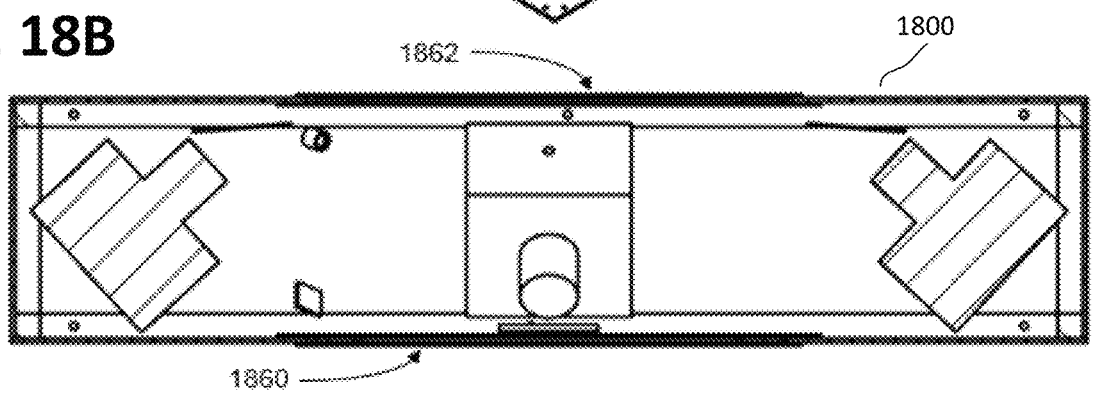

FIGS. 18A-B illustrate a system 1800 that includes a four camera, full-size double window/scintillator module beam monitor in a light-tight slim enclosure in accordance with embodiments. This embodiment is a double scintillator version of that shown in FIGS. 14A-D and incorporates both a front and back cover plate pocket design for the two "drop-in" window/scintillator frame modules. FIG. 18A is a perspective view assembly drawing showing the four cameras 1840, 1842, 1844 and 1846, with their associated mirrors including mirror 1836 coupled to camera 1846, aimed at the two window/scintillator modules 1860 and 1862. Cameras 1840 and 1842 through their respective mirrors are aimed at the bottom scintillator/window module 1860, whereas cameras 1844 and 1846 through their respective mirrors are aimed at the top scintillator/window module 1862. FIG. 18B is a cross-sectional view of the light-tight enclosure and like FIG. 18A shows two cameras with their respective folded-optics mirrors aimed at each scintillator.

Figure 19A:
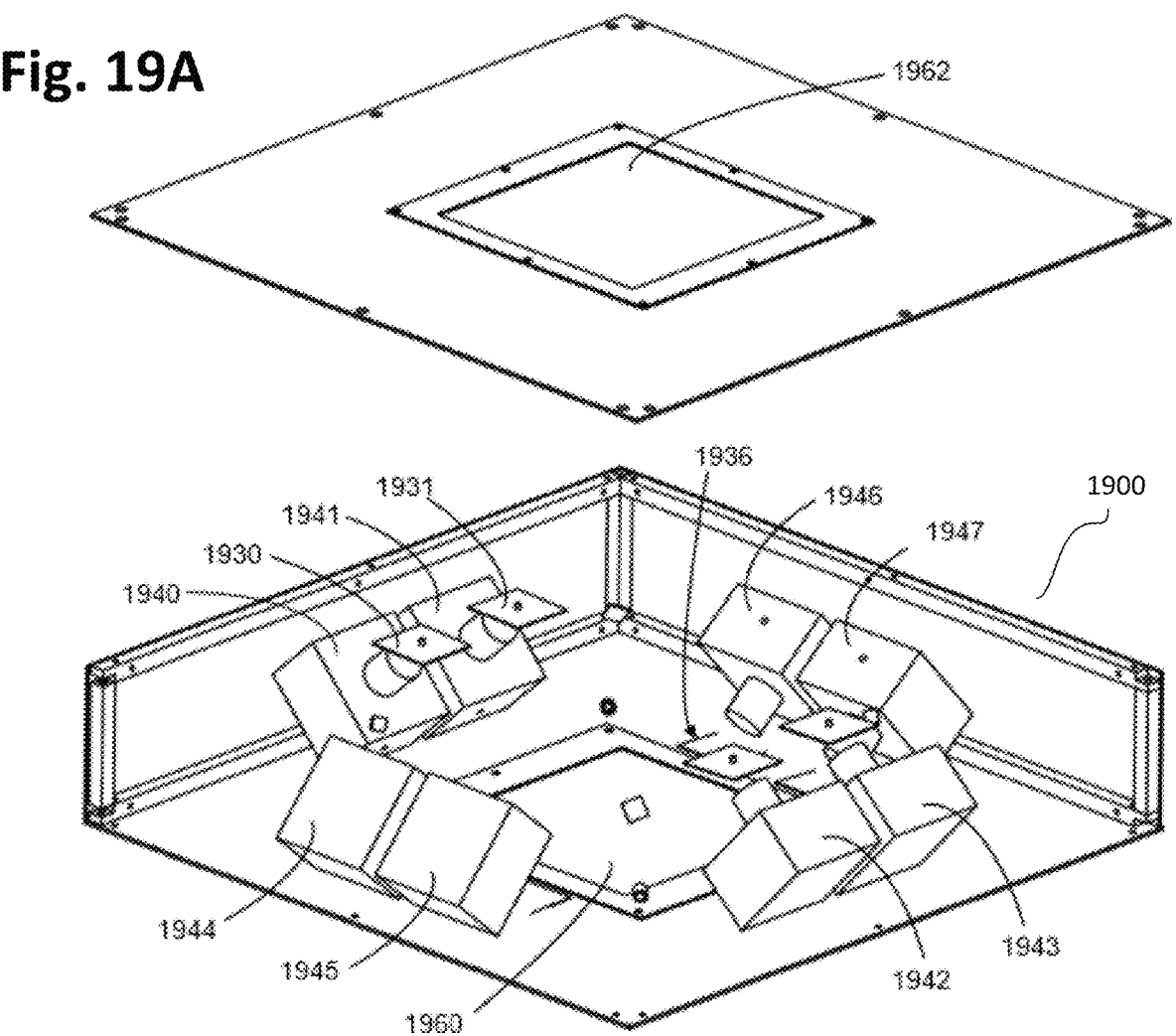
FIGS. 19A-B illustrate a system that includes an eight camera, full-size double window/scintillator module beam monitor in a light-tight slim enclosure in accordance with embodiments.
Figure 19B:
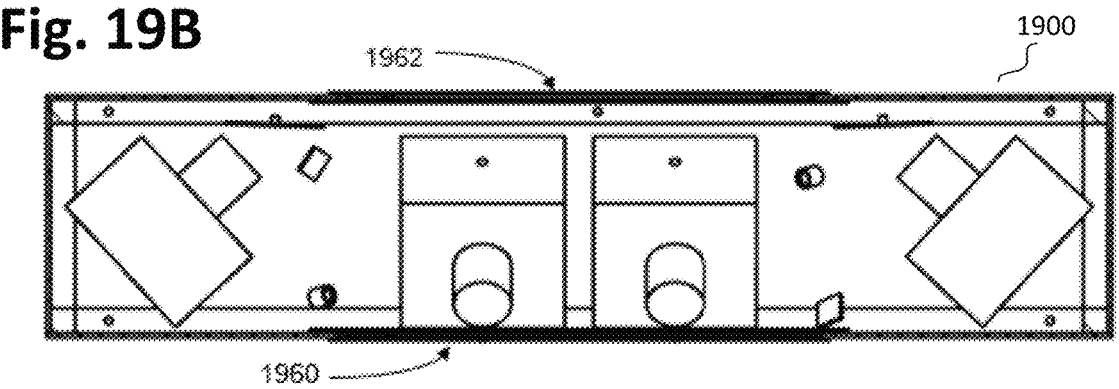

FIGS. 19A-B illustrate a system 1900 that includes an eight camera, full-size double window/scintillator module beam monitor in a light-tight slim enclosure in accordance with embodiments. FIG. 19A is similar to FIG. 18A, but the number of cameras has been doubled, similar to FIGS. 17A-D compared to FIGS. 14A-D. Cameras 1940, 1941, 1942 and 1943, though their respective fold-optic mirrors, are each aimed at one quadrant of scintillator/window module 1960. Similarly, cameras 1944, 1945, 1946 and 1947, though their respective fold-optic mirrors, are each aimed at one quadrant of scintillator/window module 1962. Mirrors 1930 and 1931 for example are coupled to cameras 1940 and 1941. FIG. 19B is a cross-sectional view of the light-tight enclosure and like FIG. 19A shows four cameras with their respective folded-optics mirrors aimed at each scintillator.

Figure 20A:
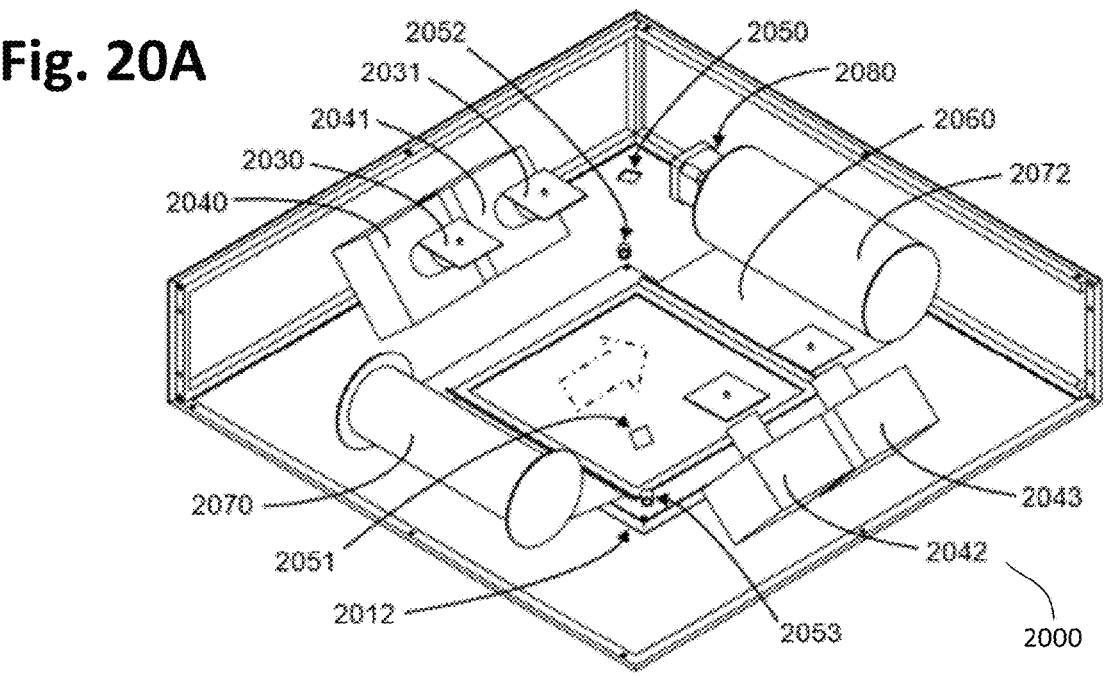
FIGS. 20A-C illustrate a system that includes a four camera, single scintillator beam monitor employing a rolled scintillator spool configuration in accordance with embodiments.
Figure 20B:
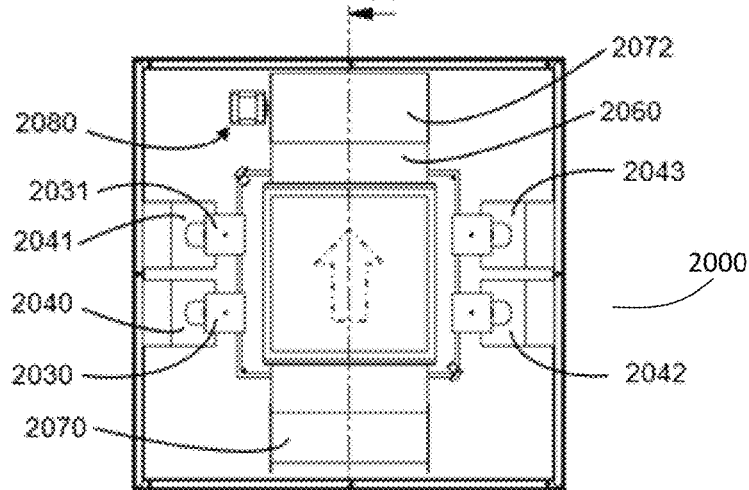
Figure 20C:
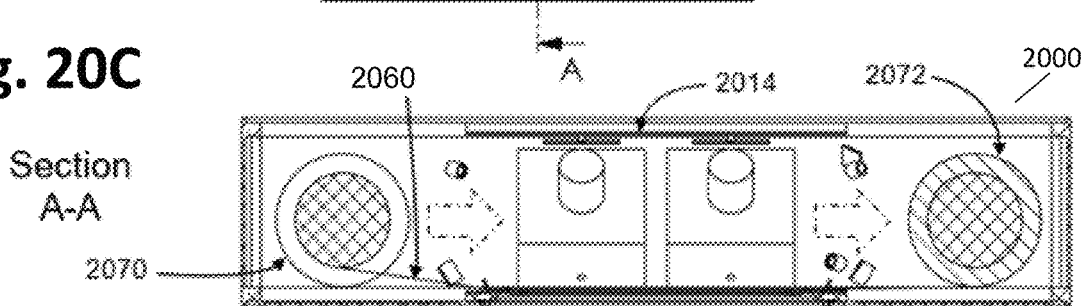

FIGS. 20A-C illustrate a system 2000 that includes a four camera, single scintillator beam monitor employing a rolled scintillator spool configuration in accordance with embodiments, and is similar to the two camera version shown in FIGS. 8A-C. FIG. 20A is a perspective view, FIG. 20B is a top view, and FIG. 20C is a Section A-A view. FIGS. 20A and 20B show cameras 2040, 2014, 2042 and 2043, and their associated folded-mirrors such as 2030 and 2031. The dotted arrows in FIGS. 20A-C show the direction of film movement from the feed roll 2070 to the take-up roll 2072. In this embodiment, film 2060 would be pulled across an active window area 2012 onto a suitable take-up spool 2072, and advanced by a stepper motor 2080 that rotates the take-up spool spindle as required. An ultra-thin dark colored or black exit window 2014, such as 15 µm to 25 µm thick black aluminum foil, is shown FIG. 20C, while two UV-LED sources 2050 and 2051, and UV-photodiodes 2052 and 2053 are shown in FIG. 20A.

Figure 21A:
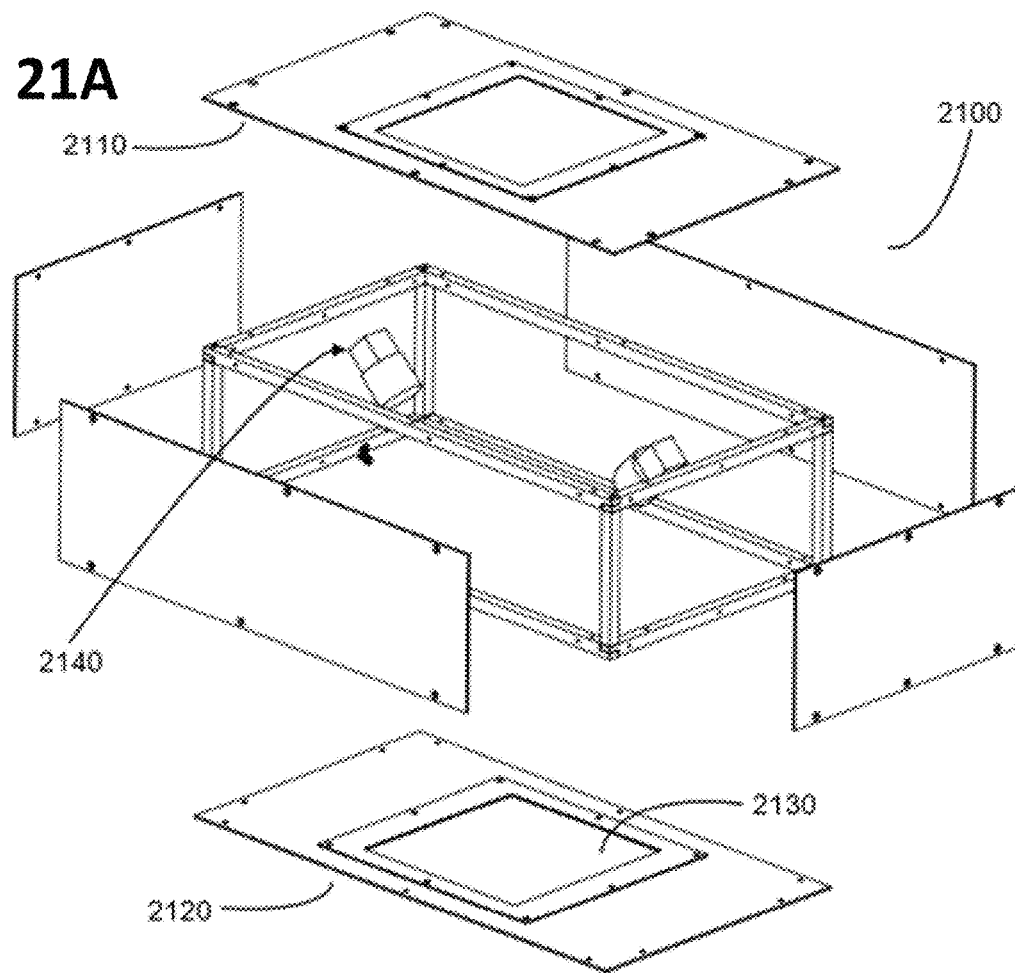
FIGS. 21A-B illustrate a two camera, full-size single scintillator-frame beam monitor without mirrors in a light-tight box enclosure in accordance with embodiments.
Figure 21B:
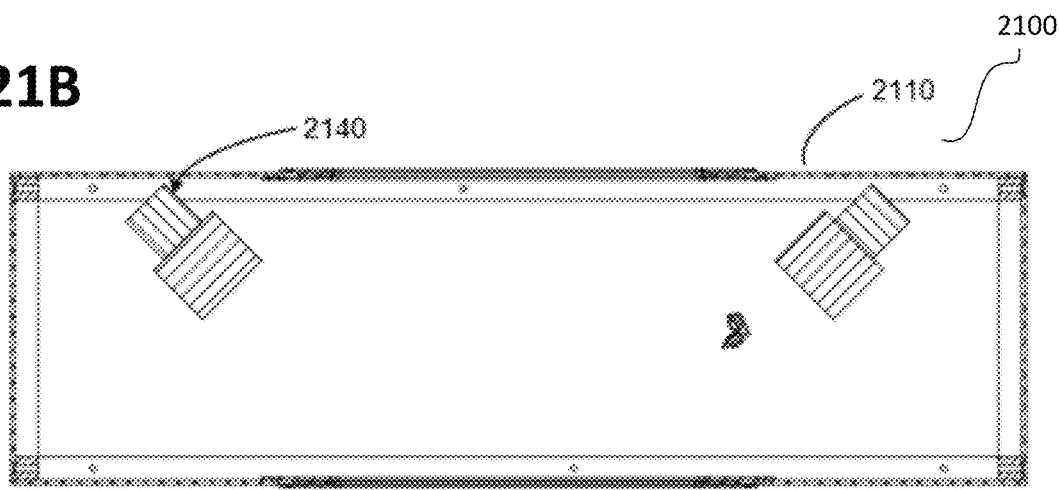

FIGS. 21A-B illustrate a system 2100 as perspective (FIG. 21A) and cross-sectional (FIG. 21B) views of a two camera 2140, full-size single scintillator-frame beam monitor in a light-tight box enclosure somewhat similar to that shown in FIGS. 14C-D, but using smaller size cameras (e.g., ~1"×1"×1") and not employing a folded optical system configuration with a mirror for each camera in accordance with embodiments. Each camera is thus aimed directly at the bottom scintillator plate 2130 resulting in the entire box enclosure being about 5 cm thicker than shown in FIGS. 14C-D. By removing the top cover plate and window 2110, and possibly even the side panels, the two cameras can be inserted just behind the exit nozzle or collimator (i.e., upstream) or alternately described as straddling behind the nozzle or collimator, and therefore integrated directly into the nozzle or collimator enclosure with the scintillator/window 2130 module inserted in the pocket of the exit cover plate 2120 located in front (i.e. downstream) of where the beam exits the nozzle or collimator. FIGS. 21A-B still incorporate one or two or more UV-LEDs and UV-photodiodes as found in all of the other beam monitors embodiments.

Figure 22A:
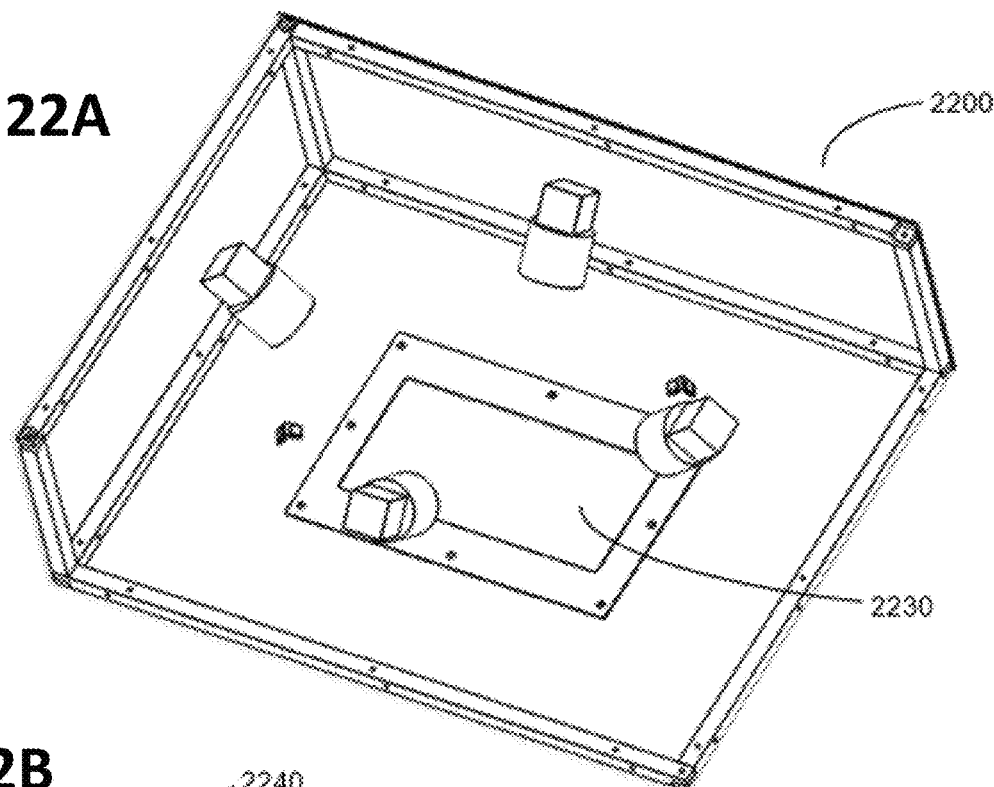
FIGS. 22A-C illustrate a system that is a four camera version of FIGS. 21A-B in accordance with embodiments.
Figure 22B:
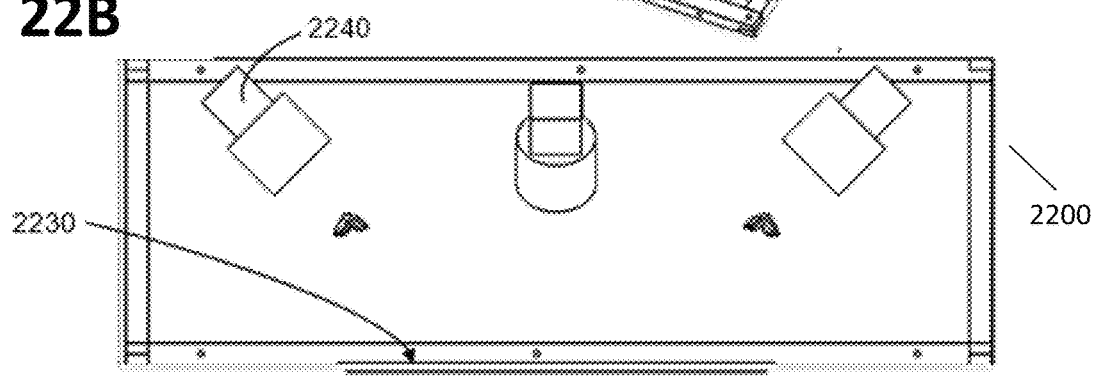
Figure 22C:
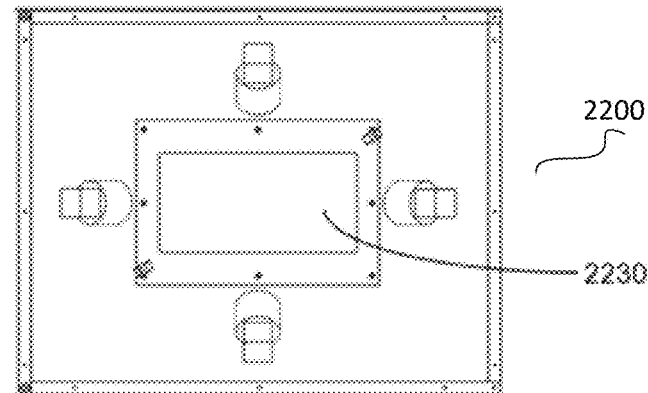

FIGS. 22A-C illustrate a system 2200 that is a four camera version of FIGS. 21A-B in accordance with embodiments. By removing the top cover plate and window as shown in FIGS. 22A-B, and possibly even the side panels, the four cameras 2240 can be inserted just behind the exit nozzle or collimator (i.e., upstream) or alternately described as straddling behind the nozzle or collimator, and therefore integrated directly into the nozzle or collimator enclosure with the scintillator/window 2230 module inserted in the pocket of the exit cover plate located in front (i.e. downstream) of where the beam exits the nozzle or collimator. FIGS. 22A-C still incorporate one or two or more UV-LEDs and UV-photodiodes as found in all of the other beam monitors embodiments.

In connection with the film rolls used in some embodiments, much longer rolls of the thickness and width disclosed above have been used for decades in aerial photography and advanced by motor drives at high speed—e.g., Kodak Aerial Ektacolor Print Film (SO-149) which with its color emulsion and gel backing has a total thickness of 213 µm. It is noted that standard 35 mm and 70 mm wide, motion picture film is typically advanced at 24 fps for "normal" motion but faster for slow motion, and some IMAX films have been run at 48 fps (i.e., 200 meters/minute). If, for example, the BoPEN film were advanced 5 cm on a biweekly basis to shift the most likely rad-damaged scintillator center area (i.e., isocenter region) midway to the side, then the previously described 20-25 meter film length could last approximately 16 years. If the same BoPEN film were advanced 10 or 20 cm biweekly, then a single roll would last either 8 or 4 years respectively before requiring replacement.

Aerial films were previously made in four standard widths, 35 mm, 70 mm, 126 mm and 240 mm. These widths are the edge-to-edge dimensions and include sprockets on both sides, so for example the maximum image width on the 70 mm film is ~58 mm, and on the 240 mm is 228 mm. The thinnest Kodak aerial film Estar "Ultra-Thin-Base made was 30 µm (i.e., 0.0012") but was still strong enough to hold sprocket holes without tearing. However the standard Kodak Estar Ultra-Thin Base was 38 µm (i.e., while the standard Kodak Estar Thick Base was 178 µm (i.e., 0.0070"). Film roll lengths for the Thick Estar Bases went from 100 to 800 feet, whereas film roll lengths of up to 2000 feet were standard for the other thinner Estar base films. A detailed thickness study by Kodak for their standard 240 mm wide Estar Base in a standard 30 meter length film roll yielded that "the thickness variation across essentially the entire roll length had a standard deviation of less than 1.85 µm". However, within the 23 cm×23 cm aerial format picture area (i.e., 9"×9") the standard thickness deviation was 1.0 µm. For Kodak 70 mm wide films, the spool core diameter was 31/32" for film roll lengths up to 200 feet for the Estar Thin Base (64 µm), 150 feet for the standard Estar Base (102 µm), and 100 feet for the Estar Thick Base (i.e. 178 µm without emulsion and 184 µm thickness for B/W emulsions and 213 µm for their thickest color film). For longer rolls of 70 mm wide film, and for all lengths of 126 mm and 240 mm width film rolls, a spool core diameter of 2.125" was used for all Estar film base thicknesses. Thus the suggested spool core diameter of 2.5" disclosed above, and film length of 20-25 meters, are conservative given the standard specifications used for aerial films, as is the film thickness uniformity across the active area.

For the multi-arm cross, roll film embodiments, the 25 µm thick BoPEN should be ideal, especially considering that the BoPEN film is stronger than the Estar Base film (i.e., BoPET) used by Kodak, and the sprocket film holes that can tear in rapid advance photographic film systems are not required for the much slower advancing roll-to-roll embodiments described herein. In addition, the 12 µm thick BoPEN is also a potentially viable thickness for the roll-to-roll scintillator film designs such as the highly transmissive beamline vacuum cross monitors shown in FIGS. 9 and 10. In terms of the mechanical viability of such ultra-thin film rolls, it is noted that 12 µm thick linear low-density polyethylene ("LLDPE") is available on a 3" core in 18" wide rolls of 1500 ft length (i.e., sold as a 47-gauge thick, polyethylene hybrid film), and even thinner 7 µm LLDPE film is available as 28-gauge film also on a 3" core in 1500 ft length rolls. With regard to film strength, BoPEN is much stronger than LLDPE, having at least three times the tensile strength. As such, BoPEN rolls/coils are available in ultra-thin films down to 1.3 µm thickness in 12" and wider size rolls, whereas 12 µm thick BoPEN film is available in 40" wide rolls of 9800 ft length.

For embodiments that do not require roll-to-roll film advance systems, a variety of simpler yet more versatile transmissive beam monitor embodiments have been designed for fast exchange of different scintillator materials optimized for a wide variety of ionizing particles and energies including photons and neutrons in a wide range of film and sheet thicknesses (e.g., from ~1 µm to ≥0.1 mm). For those monitors designed for beamline applications, both single-frame and double-frame, multi-arm cross structures are disclosed in which the scintillator is mounted to a stiff frame hi contact with a push-pull mechanism as shown for three different 6-way-cross embodiments in FIGS. 11A-D, and 12A-C, and 13A-C below. It only one camera is required and no PMT, then a less expensive 5-way-cross can be employed, and depending upon the frame and arm (or nipple) length, the scintillator can be pulled out of the beam path entirely and pushed into the beam path only when beam monitoring is required (e.g., as shown in FIG. 12B). Another advantage of mounting the scintillator film to a rigid frame, as compared to a roll-to-roll system, is that thick scintillators (e.g., ≥0.5 mm) cannot be rolled onto a small diameter spool, while the thinnest scintillator films of only a few microns cannot be reliably advanced across the beam axis transit area without risk of damage when pulling it from the feed spool

1030 onto the take-up spool 1024 as in FIG. 10A. As disclosed, 3, 6, 12 and 191 μm thick BoPEN films have unexpected characteristics of radiation hardness and fast recovery (see FIG. 3). Other embodiments can use 1.3 μm BoPEN films or 250 μm thick BoPEN films for several different applications.

All of the embodiments disclosed herein with associated figures/drawings incorporate the previously described system/hardware required for internal calibration and beam image analysis. The calibration system and its operation can be initiated either manually or automatically (e.g., on a pre-programmed schedule) and is based on activating an internal UV-LED source or sources to illuminate the scintillator film for a short time (e.g., seconds) and capturing images of the fluorescence intensity pattern and comparing them to previous images by means of an appropriate computer system to detect any changes in the system response, including changes in the scintillator fluorescence or camera sensor such as might be caused by radiation damage, etc. In order to monitor the stability of the UV-source, each UV-LED is itself monitored by a dedicated proximity UV-photosensor such as a photodiode to correct for any source intensity change or drift over time. The computer system in one embodiment is a dedicated, low-latency, fast-PC (personal computer) or workstation, etc., having a processor that executes instructions. In other embodiments, the computer system is a customized FPGA based PCB (printed circuit board) or frame grabber, although more likely a frame grabber connected to a computer. For some systems the FPGA could be partially or fully embedded in the camera(s). The computer system besides performing internal calibration checks, is also programmed to perform image analysis in real-time of the beam as it irradiates the scintillator so as to monitor and analyze in two-dimensions ("2D") the beam position and beam shape, beam movement, the beam intensity profile including tail, beam fluence and external dosimetry, and beam angular divergence in the case of the beam monitor configuration incorporating two or more scintillators in the beam path and separated by an appropriate distance. In addition, because all of the embodiments incorporate one or more machine vision cameras oriented at an angle to the scintillator plane, all of the camera images will incur perspective/tilt distortion (i.e., keystoning), while the camera lenses, especially due to their close working distance, will exhibit some amount of optical distortion as well as vignetting, and the camera sensors themselves can never be perfectly uniform in terms of each pixel having exactly the same response. AD of these system hardware related non-uniformities can be corrected by calibration of the integrated system and frequently checking this calibration by taking repeated images of the system response to the UV-source illuminated scintillator and automatically adjusting the calibration as needed by the computer system.

In order to minimize maintenance and down time, and to further optimize the design, fast scintillator replacement is required in embodiments. This is achieved in all of the embodiments shown in FIGS. 14-19 and 21-22 by the design of a thin (e.g., 2 mm to 3 mm thick), replaceable large window/scintillator frame module assembly such as 1460 in FIG. 14A that can be easily accessed and dropped from the outside into a small pocket (~2-3 mm deep) in the front and/or back enclosure cover plate(s) 1414, and secured from the outside with a thin 1-2 mm thick retaining frame 1410 as shown in FIG. 14B. The window/scintillator module assembly 1460 consists of ultra-thin window 1402, such as 15 μm to 25 μm thick black aluminum foil, and a scintillator film or sheet 1406, with both components attached or glued to opposite sides of a thin frame 1404, Replacement of the ultra-thin window/scintillator module using the design in FIGS. 14A-D should take only a few minutes. If only one scintillator/window module 1460 is employed, then an ultra-thin window by itself such as 1402 is glued to the frame 1404 without adding the bottom scintillator plate. The window module itself, without a scintillator component, is shown as 1422 in FIGS. 14C-D and fits into the pocket of cover plate 1420 and held in place by a retaining frame (e.g., 1410 in FIG. 14B) as shown in FIG. 14C. FIGS. 14C-D show one such embodiment based on a 2 camera, 1 scintillator arrangement, with both cameras 1440 and 1442 indirectly aimed at the back scintillator 1406 in the back window/scintillator module 1460 through their respective folded-optics mirrors 1430 and 1432. Also shown are UV-LEDs 1450 and UV-photodiodes 1452 in FIGS. 14C-D.

Embodiments include a number of different light-tight enclosure beam monitors incorporating one or two scintillators and from one (1) to twelve (12) or more cameras, depending upon the desired beam spatial/positional resolution and the required scintillator active area size which for EBRT applications can typically extend up to about 40 cm×40 cm. In general, for a 20 cm×20 cm scintillator, the intrinsic 2D position resolution should be on the order of ~0.03 to 0.2 mm, depending upon the required UFT beam monitor specifications. However, no matter how many cameras are employed, such as 1, 2, 3, 4, 6, 8, 10, 12 or more (see FIGS. 8 and 14-22), the software required for stitching multiple camera images together is commercially available for scientific, industrial, medical, consumer applications, etc. For example, a number of smartphones now employ multi-camera systems, such as the Samsung Galaxy S10 and S10+, which use 3 cameras to stitch together high quality images with minimal distortion that can cover the full range from ultra-wide angle to telephoto. The above disclosed platform can perform the equivalent of stitching together multiple images as they stream in from multiple machine vision cameras in order to track and analyze the moving particle beam or photon beam as it travels both horizontally and vertically across the scintillator surface. For such streaming images the software in embodiments is mostly FPGA based, on a multi-camera frame grabber based system that can provide calibration and corrections for optical distortions and equipment/system non-uniformity.

Depending upon the application requirements in terms of: image/pixel resolution, low-light sensitivity, pixel bit depth (i.e., gray scale), exposure time (i.e., shutter speed), frame rate, and image processing speed including system latency, camera images can be streamed live, processed and analyzed in real-time at rates potentially as fast as 25-100 is per image (i.e., 10,000-40,000 fps) depending upon the system hardware, firmware and software, including the choice of camera interface. For example, machine vision cameras operating at over 30,000 fps, corresponding to a timing resolution of ~33 μs, can still provide sub-mm image resolution for embodiments such as the above multi-camera, 20 cm×20 cm, or even 40 cm×40 cm, scintillator EBRT beam monitors at a cost of about $5K to $8K per camera is single unit quantities. The larger size 40 cm×40 cm scintillator beam monitoring systems in accordance to embodiments employ 4 or more cameras, and are configured if desired with two different types of cameras—for example in a single-scintillator 6-camera configuration there could be four relatively inexpensive high picture resolution, low frame rate (fps) cameras, plus two of the more expensive high fps cameras; other combinations are also possible such as 4 slow and 4 fast cameras, or 4 low sensitivity and 4 high sensitivity cameras in a 8-camera system. In fact, low cost, high spatial resolution, low sensitivity, low fps cameras could even be paired side-by-side with ultra-fast, high sensitivity, ultra-compact PMTs (e.g., Hamamatsu H11934 series with dimensions of 30 mm×30 mm×32 mm) with camera lenses coupled to each PMT thereby viewing the same scintillator area as the camera. The PMTs would provide the low-light sensitivity and dose rate information with ultra-fast ns and sub-ns response capability (e.g., 10 ns is equivalent to 100,000,000 fps). For applications requiring frame rates of 1,000-2,000 fps or slower, smaller size machine vision cameras can be procured for ≤$1 K (see below).

Figure 23A:
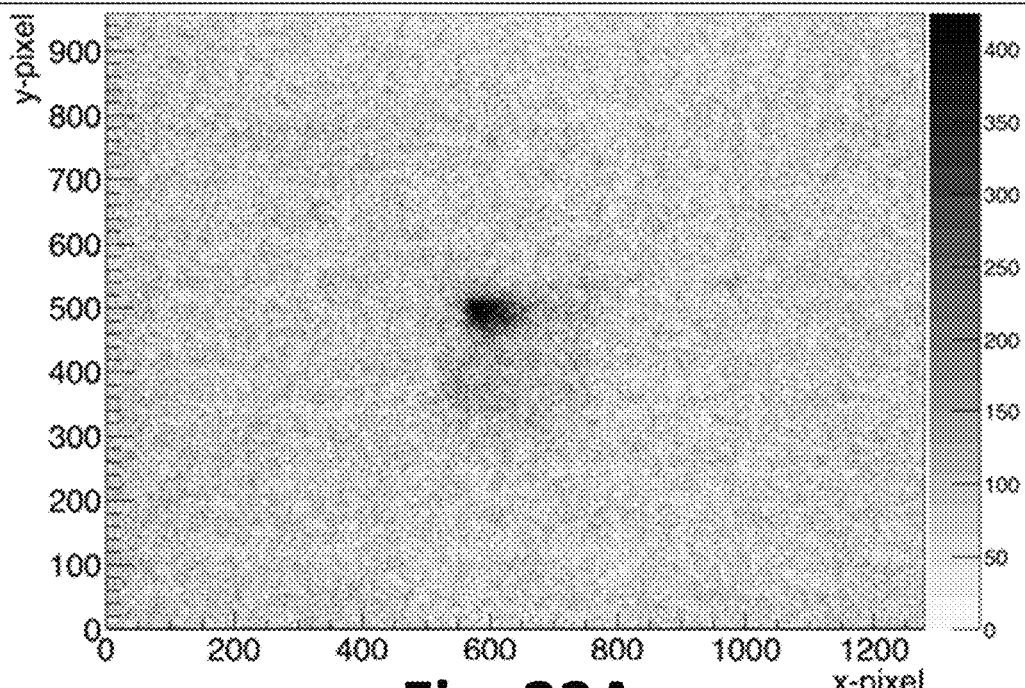
FIGS. 23A-B illustrate 10 is exposure camera images through a vacuum chamber window in accordance to embodiments.
Figure 23B:
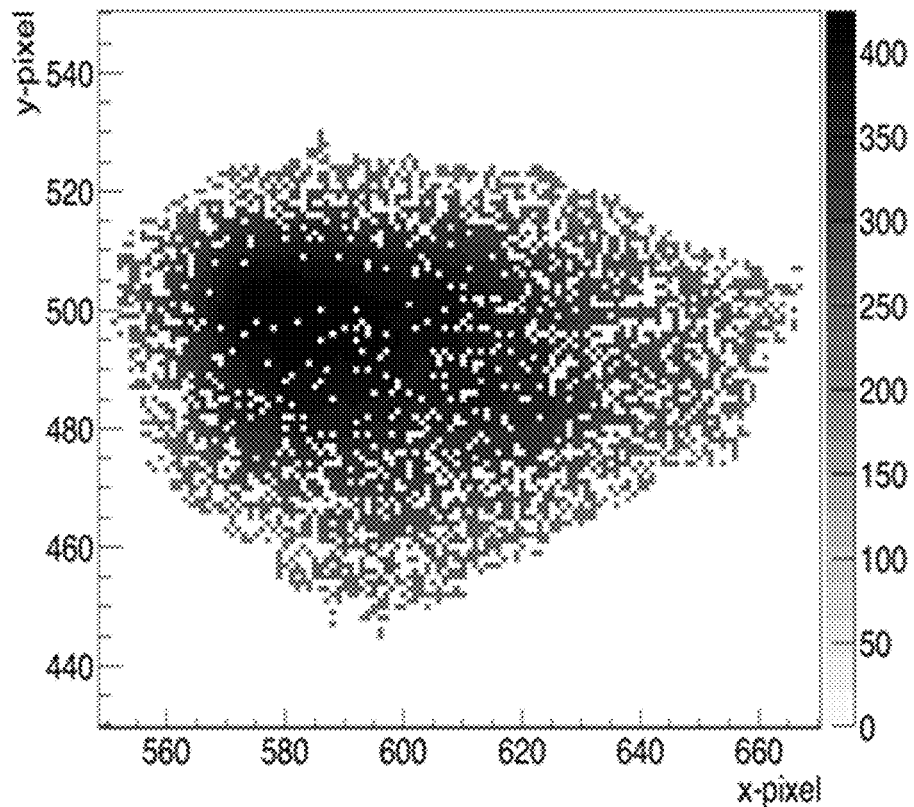

FIGS. 23A-B illustrate camera images through a vacuum chamber window of a ~3.6 mm diameter proton beam, moving at 80 mm/ms, irradiating a 191 µm thick BoPEN scintillator, with a 10 µs exposure in accordance to embodiments. The camera used is a Basler daA1280-54 um with a 25 mm FL, f/1.4 lens, at a working distance of ~350 mm, with a pixel field-of-view of 48 µm×48 µm. FIG. 23A constitutes an image of the camera's full field-of-view.

In FIGS. 23A-B, the proton beam energy was 5.4 MeV at a 10 nA beam current. FIG. 23B is an enlarged and cropped image with the background digitally removed of the beam spot area in FIG. 23A, showing the pixel resolution detail including the intensity distribution and beam shape and dimensions which covers an irregularly shaped elliptical area of ~60×100 pixels. The beam horizontal "smear" during the 10 µs exposure due to the 80 mm/ms movement is only ~0.8 mm, or about a 22% elongation.

Figure 24:
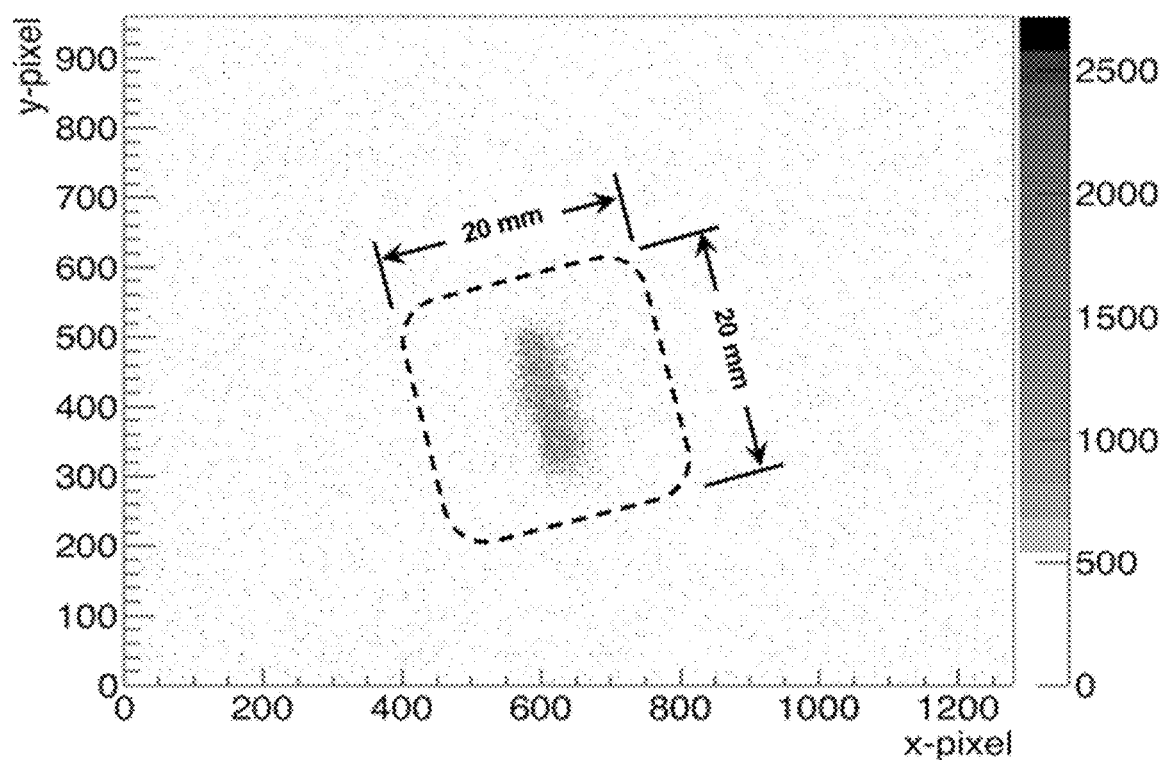
FIG. 24 illustrates a 1 ms exposure of a captured image of a ~2 mm diameter proton beam irradiating an ultra-thin 12.2 µm BoPEN film while moving back and forth in a rastered zig zag pattern at 40 mm/ms in accordance to embodiments.

FIG. 24 illustrates a 1 ms exposure of a captured image using the same camera/lens as in FIG. 23, but of a ~2 mm diameter proton beam irradiating an ultra-thin 12.2 µm BoPEN film while moving back and forth in a rastered zig zag pattern at 40 mm/ms in accordance to embodiments. As with FIGS. 23A-B, the proton beam energy is MeV at a 10 nA beam current, but at a lens working distance of ~390 mm, corresponding to a somewhat larger 55 µm×55 µm field-of-view pixel resolution. Similar images have been captured on BoPEN films as thin as 3.0 µm, with plans to irradiate a 1.3 µm thick BoPEN film in the near future.

One embodiment uses Universal Serial Bus ("USB") as the system interface, hardware and processing software, which is capable of processing and analyzing images at rates up to about 1,000-2,000 fps (i.e., 1.0 ms to 0.5 ms). For higher performance, embodiments use a number of faster camera interfaces for interfacing with high-speed FPGA based frame grabber hardware, firmware and software, to process and analyze the streaming images at much higher speeds, including CoaXPress 2.0 (CPX-12), GigE (10 Gigabit Ethernet), Camera Link HS, etc.

Referring again to FIGS. 11A-D, both cross-sectional and perspective views of a single scintillator-frame beam monitor are shown. FIG. 11A shows 4 of the 6 arms of a modified CF-flange 6-way-cross vacuum chamber configuration, although any type of flange system can be used (e.g., ConFlat, KF/QF, ISO-K, ISO-F, ASA, Wire-Seal, etc.). The two arms not shown in FIG. 11A are perpendicular to the plane of the drawing where the beam enters 1101 the cross center as seen in FIG. 11B. Either or both of these two arms can incorporate an optional gate valve attached to one or both flanges for vacuum isolation. FIG. 11B shows one such gate valve 1110 attached to the exit arm flange. As the integrated exposure of the scintillator to the ionizing beam accumulates over time, so does the radiation dose which would typically be concentrated in or near the beam pipe center. Therefore, at such time that the scintillator radiation damage becomes significant, the scintillator-frame unit 1140 is nudged or pushed by shaft 1172 an appropriate distance (e.g., ~1 cm, or more) on its track 1145 in FIG. 11D towards the opposite side (i.e., the right side in FIGS. 11A-D) to bring unexposed or minimally exposed scintillator film into the central beam path region. This linear shift/movement can be accomplished either manually, or controlled pneumatically, or by a stepper motor as indicated by the linear positioner 1170 shown on the left side in FIG. 11A.

FIG. 11A shows the camera 1104 and camera lens 1106 in the top nipple, along with the UV-LED/UV-photodiode assembly combination 1180, and a conical reducer nipple 1190 to the vacuum-exhaust/air-bleed line (not shown). FIG. 11D shows a close-up of the two small UV-LEDs 1186 and UV-photodiodes 1182 positioned on opposite sides of the camera lens. The PMT 1160 in the bottom nipple is shown most clearly in FIG. 11C, while the two condensing lenses 1150 and 1152 on either side of the viewport window 1156 in the bottom nipple are best seen in FIG. 11D. FIG. 11D provides a close-up magnified view of the 6-way-cross center area in which the two viewport windows 1155 and 1156, UV-LEDs, UV-photodiodes, two scintillator-frame tracks, and the two condensing lenses are most easily seen.

Most of the embodiments disclosed herein include at least one UV illumination source, with at least one UV photosensor to monitor the stability of each UV source. The UV source employed in some embodiments for the BoPEN scintillator is a UV-LED with peak emission at ~280 nm, where the BoPEN scintillator film essentially absorbs at least 99% of the source photons at the film surface within a ~0.1 µm thick layer. The UV photosensor used to monitor the UV-LED in embodiments is a UV-photodiode. If needed, the UV source and/or UV photosensor can be coupled to a suitable UV bandpass or UV shortpass filter. When the rad-damage in any particular area starts to become significant, the scintillator-frame is pushed slightly towards the far side until such time as the frame has been pushed completely to the far side as shown in FIGS. 11A and 11D. Once the scintillator has been fully radiation damaged along its useable length, the scintillator-frame is then pulled back to its initial position and the scintillator-frame replaced. Replacement requires breaking vacuum in the 6-way-cross chamber, but because of the excellent BoPEN rad-hardness (see Table 1 above) it might be possible to schedule such replacement during preplanned downtime periods allocated for general maintenance.

If the scintillator 6-way-cross chamber includes both entrance and exit gate valves, then breaking vacuum is limited to the small chamber volume with no impact on the rest of the beamline and so scintillator-frame replacement can be done whenever convenient and should only take about an hour or so including ambient pressurization and re-evacuation. Other features of consequence are the machine vision camera in the top arm, the PMT in the bottom arm, the push-pull linear positioner on the left side, and the reducer nipple on the right side which is connected to a small vacuum pump system (not shown) with a bleed valve for chamber pressurization followed by re-evacuation. Also not shown are the described beam entrance gate valve, although the exit gate valve is easily seen in FIGS. 11B and 11C and so an entrance gate would look the same when attached to the entrance flange in FIG. 11B. Both the camera and PMT in their respective nipples are kept in an air atmosphere at ambient pressure. This is achieved on the camera side by having a UV transparent viewport window 1155 inserted between the cross flange and the camera nipple. The reason for a UV window is because the UV-LED in this embodiment is located on the side of the camera lens.

If the camera power consumption is large enough to cause significant heating, then the nipple back flange can be left open or vented to facilitate air cooling by either natural or forced convection as long as the front of the camera or lens barrel is appropriately light shielded behind the UV-LED and UV-photodiode. The same viewport window arrangement is used on the PMT side, but for the BoPEN scintillator or other scintillators with shorter decay times (e.g., EJ-200, EJ-204, EJ-212, EJ-228, EJ-262, etc. from Eljen Technology) with emission peaks in the violet-blue-cyan region, the viewport window 1156 can be glass.

To maximize the PMT light collection efficiency a set of highly efficient, high transmission glass (e.g., Schott B270) aspheric condensing lenses are employed with an f/number that can be less than 1.0 (e.g., between f/0.6 to f/0.9). For maximum efficiency, the first condensing lens 1150 is located inside the cross vacuum chamber just below the scintillator/frame, while the second lens 1152 is located just below the glass viewport window 1156 and in front of the PMT at ambient pressure as shown in FIG. 11D. Both lenses can be anti-reflection coated for maximum light transmission and the second lens located in front of the PMT can further reduce reflection loss by optically coupling it to a matching refractive index plastic or glass light guide (e.g., cylinder) thereby eliminating the air gap completely. The PMTs should be selected for minimum jitter (e.g., ≤0.3 ns), maximum quantum efficiency (e.g., ≥22%), and most importantly for maximum gain (e.g. >1×10$^6$). Besides having a short decay time, the scintillator should have a high light yield and if capable of total internal reflection (TIR) could have a reflective coating deposited on the non-collecting surface, or surface roughened to eliminate TIR on the light collect surface, or for optimum TOF performance could employ two matching PMTs with two sets of condensing lenses in the 6-way-cross (i.e., replacing the camera with a second PMT).

The embodiment shown in FIGS. 12A-C is similar to that in FIGS. 11A-D, but with the addition of two horizontal full-nipples 1290 and 1292 to accommodate a dual scintillator-frame configuration. Similarly the embodiment in FIGS. 13A-C is quite similar to that in FIGS. 12A-C, but with the important addition of two vertical gate valves 1310 and 1311 that effectively transform the embodiment in FIG. 12 into the load-lock vacuum chamber of FIG. 13. FIGS. 12A-B show 4 of the 6 arms of the customized 6-way-cross vacuum chamber; the two arms not shown are perpendicular to the plane of the drawing where the beam enters and exits the cross center. FIG. 12C is a perspective view showing all 6 sides/arms, including the two perpendicular arms where the beam enters 1201 and exits 1202 and which can incorporate one or two optional gate valves such as 1310 and 1311 as shown in FIGS. 13A-C and previously discussed for FIG. 11. The dual scintillator-frame embodiments employ either a straight track 1245 or a segmented track 1345, as shown respectively in FIGS. 12A and 13A that goes through all three chamber sections on which the scintillator-frames can be pushed or pulled. If two identical scintillators are employed, the maximum time before scintillator replacement can be essentially doubled. The dual scintillators 1240 and 1241 in their frames as illustrated in FIGS. 12A-B also allow two different scintillator materials to be employed, each selected for a different purpose. For example, one scintillator might be selected for minimum film thickness and maximum beam transmission (e.g., BoPEN), with the other selected for minimum decay time and rise time to provide the fastest possible timing when coupled to an efficient light-collection system such as the condenser lens system shown in FIGS. 12A-B, which can be seen more clearly in FIG. 11D as lens elements 1150 and 1152, and a fast PMT 1060, 1160 & 1260 in FIGS. 10A, 11C and 12B respectively for sub-ns TOF (time-of-flight) measurements. With embodiments, timing resolutions of ≤0.1 ns are achievable for highly ionized, high-Z (i.e., atomic number) beams using the 6-way-cross beam monitors shown in FIGS. 10A, 11A-D and 12A-B.

As discussed above, for the embodiment shown in FIGS. 12A-C, the two scintillators mounted in their respective frames can either be identical or the first scintillator-frame combination 1240 might be selected for fast timing (e.g., BC-400 from Saint-Gobain) and the second being a thinner scintillator 1241 of different composition, such as BoPEN, selected for maximum beam transmissivity with minimal beam scattering and energy loss (i.e., from an incident photon or particle beam such as protons, ions, electrons, neutrons, etc.). The scintillator-frame 1241 in its initial start position is shown in FIG. 12A before being nudged or pulled in small steps towards the opposite (i.e. right) side as in FIG. 12B to bring unexposed or minimally exposed scintillator film into the central beam path region. Such linear movement can be accomplished either manually with linear push-pull positioners 1220 and 1230 in FIG. 12A, and 1320 and 1330 in FIG. 13A, or controlled pneumatically or by a stepper motor.

As the integrated exposure of the scintillator to the ionizing beam accumulates over time, so does the radiation dose which would typically be concentrated in or near the beamline cross center 1250 shown in FIG. 12B. The two horizontal length nipples 1290 and 1292 hold the two scintillator-frames 1240 and 1241 in FIG. 12B with scintillator-frame push-pull linear positioners 1220 and 1230 attached to their respective nipple and scintillator-frame that push or pull the two scintillator frames on their tracks from the left side across the beam center area 1250. When fully "used up" (i.e. radiation damaged) the center scintillator-frame is pulled from the right into the right side nipple chamber 1292 in FIG. 12A (or 1392 in FIG. 13A) for removal, while the left scintillator-frame 1340 in the left side nipple 1390 in FIG. 13A can be pushed into the center of the 6-way-cross where the beam enters through flange 1301 in FIG. 13C. The top vertical nipple contains the camera 1004, 1104, 1204, 1304 in FIGS. 10-13 respectively, and camera lens 1006 or 1106, while the bottom vertical nipple contains the PMT 1060, 1160, 1260 or 1360 (or SSPM). The two vertical nipples containing the camera and PMT are at ambient pressure and isolated from the vacuum by their hermetically-sealed windows—e.g. 1155 and 1156 shown in FIG. 11D. The scintillators are pushed-pulled along a three section channel/rail or track 1345 in FIGS. 13A and 13B with two breaks or open-segments of ~2 cm each through which the two gate valves 1310 and 1311 can close. The scintillator-frames 1340 and 1341 can each be removed without breaking vacuum by closing a gate valve. With the gate valves closed, each scintillator nipple section can be individually pressurized for scintillator replacement and then re-evacuated using a small pump through the two nipple tee sections 1391 and 1393.

The embodiment shown in FIG. 12 does not have any gate valves to isolate each nipple during scintillator replacement, so "nipple" 1290 is actually a reducer tee with reducer flange 1291 for connection to an external pressurization line and optional vacuum line to minimize downtime during scintillator replacement. This arrangement is similar in function to the conical reducer nipples 1090 and 1190 shown in FIGS. 10A and 11A for attachment to an external pressurization/ vacuum-exhaust line. Although not easily seen in FIG. 12 or 13, for internal calibration purposes the described embodiments include UV-photodiodes 1082 and 1084, as shown on each side of the camera lens 1006 in FIGS. 10A and 10C, to monitor the output of each UV-LED 1086 and 1088 in order to correct for changes in the UV-LED output luminosity. This internal UV-LED/UV-photodiode calibration system 1080 in FIG. 10A, also shown as 1180 in FIG. 11A, and 1182 and 1186 in FIG. 11D, can also be used to monitor and correct for any changes with time or temperature of the camera sensor output.

Depending upon the specific application and beamline monitoring requirements, a number of variations of the 6-way-cross structures described above and in FIGS. 9-13 are available. For example, if a PMT is not required, then a 5-way-cross can be used, but if spatial resolution, sensitivity and accuracy are paramount, then the 6-way-cross could be used with two cameras—i.e. the second camera replacing the PMT as shown in FIG. 9A. Alternatively, if the beamline monitor is to be optimized for time-of-flight ("TOF") measurements with the highest timing resolution and accuracy required, then two closely-matched PMTs with two sets of condensing lenses can be employed, and the camera eliminated as discussed previously. For other applications only a 3-way-tee or 3-way-wye might be required, or a 4-way-cross could be utilized.

Not all beamline monitoring systems need to be integrated into a vacuum beam pipe environment, including segments of electron and neutron beam delivery systems. Such systems, however, can still utilize the various multi-arm-cross embodiments disclosed herein. For monitoring the beam in air, the crosses do not have to be evacuated but can simply be made light-tight by adding a thin foil or dark/black polymer film window, or some polymer-foil combination thereof, to the entrance and exit flanges. For enhanced scintillator recovery, the air atmosphere can be replaced by any gaseous atmosphere including oxygen or oxygen enhanced mixtures, or pure nitrogen or argon or any other type of specified atmosphere.

All of the embodiments with cameras include the camera or cameras viewing the scintillator at various angles of incidence or reflection, the latter indirectly via a folded-optics mirror system. Parameter optimization determines the most appropriate camera lens angle of incidence with respect to the normal to the scintillator plane (i.e. surface) or mirror for each application. For most of the embodiments disclosed here, the camera lens viewing angle with respect to the scintillator will typically fall within the range of 25-65°, with an average value of ~45°. For the camera images captured in FIGS. 6, 23 and 24, the camera angle of incidence with respect to the scintillator normal typically fell within 10-20°. For the embodiments in FIGS. 8-22, the mean camera angle with respect in the scintillator normal, or mirror normal in the case of FIGS. 8 and 14-20 was typically 40-50° but can be increased to minimize the enclosure depth or thickness. However, any camera angle greater than a few degrees will create some angular distortion of the image, and depending upon the amount of distortion, a circle, for example, can look like or appear as a distorted ellipse. In fact, for a camera to scintillator angle of just 5°, the distortion will start to be noticeable, and at a 10° angle the distortion will definitely be noticeable. Therefore at the 10-20° angles for the images in FIGS. 6, 23 and 24, the discussed ellipsoids might actually be circles but only appear to be ellipsoidal due to this distortion. In the case of images of a moving or rastering beam, the beam motion will further distort the shape of the image in the propagation direction (see FIGS. 23 and 24). These image distortions can be corrected by software.

Figure 25:
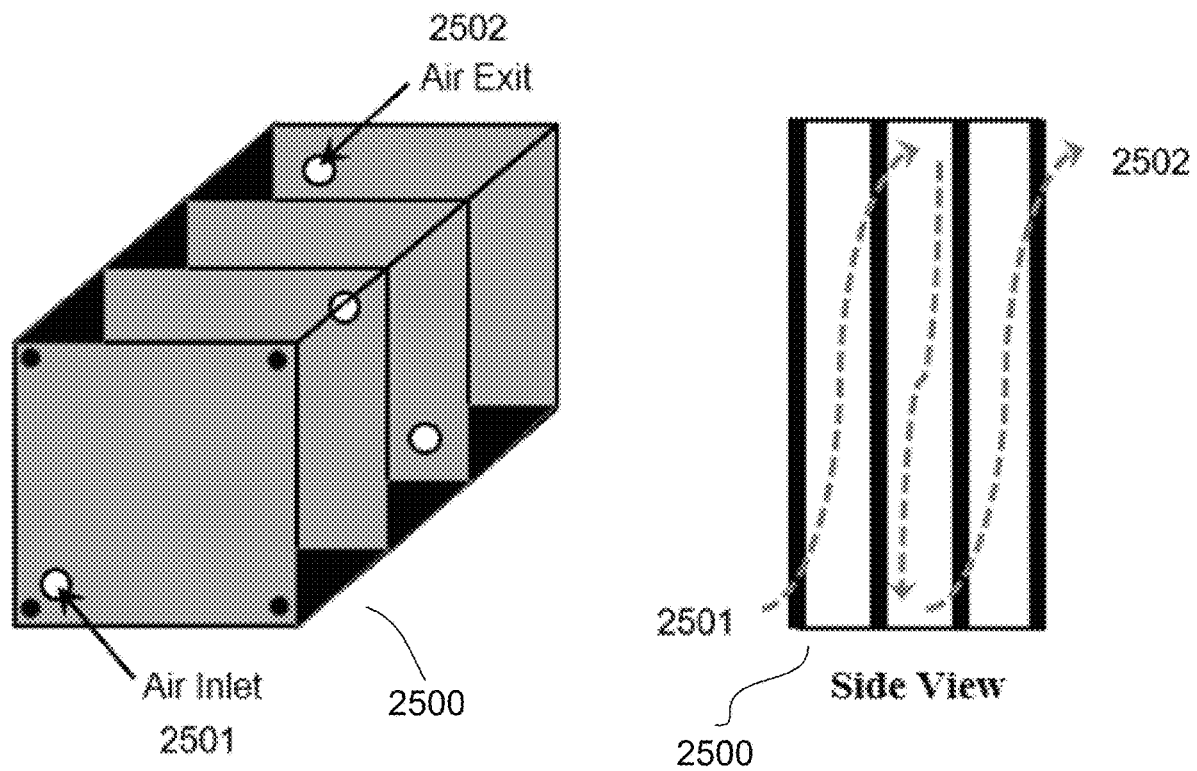
FIG. 25 illustrates a four plate light baffle for air circulation in accordance to embodiments.

FIG. 25 illustrates a four plate light baffle 2500 for air circulation within a light-tight enclosure by natural convection in accordance to embodiments. A more efficient light-tight air circulation arrangement by means of forced convection can be realized by the addition of one or more miniature fans.

Figure 26:
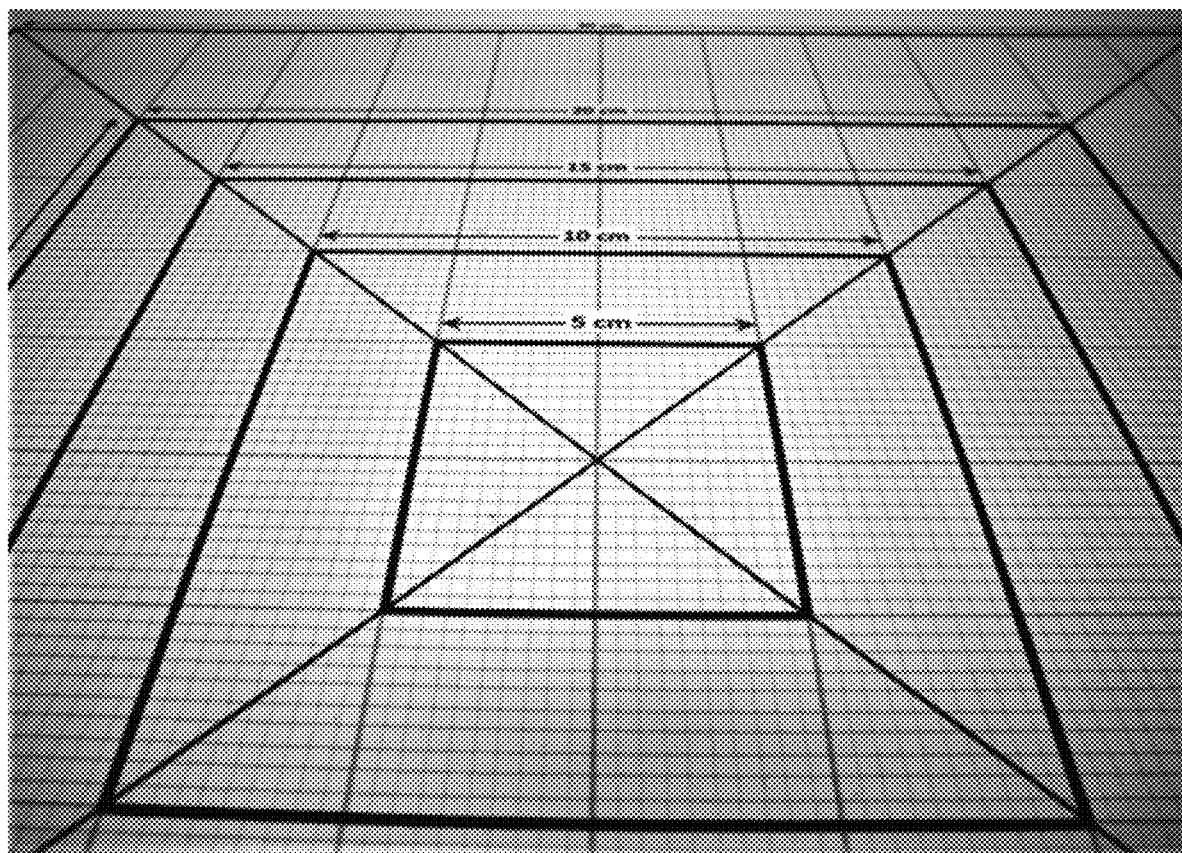
FIG. 26 is a photograph of a 25×25 cm rectilinear image taken at a 45° tilt angle in accordance to embodiments.

FIG. 26 is a photograph of a 25×25 cm rectilinear image taken at 45° tilt angle in accordance to embodiments. FIG. 26 shows perspective distortion, also known as the keystone effect (e.g., image foreshortening caused by the angle-of-tilt with respect to the lens orientation).

The angular distortion disclosed above caused by the angle of tilt, as shown in FIG. 26, is known as a perspective distortion, but also called tilt distortion, the keystone effect, keystone distortion, or simply keystoning. A familiar example occurs when taking a picture of a tall building from the ground, with the building looking more and more trapezoidal the taller it is and the greater the camera angle of tilt. None of the images presented herein have been corrected for this distortion, but it is easily corrected in real-time with modern image editing software. Obviously the greater the angle of camera lens tilt, the greater the distortion, and the greater the difference in image resolution at the image top edge as compared to the bottom edge. For example, in FIG. 8 and FIGS. 14-22, at an average camera lens viewing angle with respect to the scintillator of ~60° instead of the 45° angle in FIG. 26, there will be approximately a factor of two (i.e., 2×) difference in image resolution at the image top edge compared to the bottom edge for a camera focused on the center of a 10 cm×10 cm scintillator quadrant (e.g., FIG. 17 and FIGS. 19-20), with a 10 cm working distance from the camera lens to the closest point of the image field (i.e., top of quadrant). Angles of 60° or even greater are necessary for achieving the thinnest beam monitor configurations possible, such as those required by BNCT, disclosed below.

Although the above embodiments have mostly been described and tested in terms of their applicability to proton beams and proton beam therapy, these embodiments are applicable to all types of particle beams including those for particle beam therapy (e.g., protons, helium-ions, carbon-ions, electrons, etc.), as well as neutron particle beams. Fast neutrons can still benefit from the described advantages associated with BoPEN scintillator films, but slow to thermal neutrons require boron or lithium or gadolinium doped scintillators, such as boron doped EJ-254, which is of interest for boron neutron capture therapy ("BNCT") and gadolinium neutron capture therapy ("GdNCT"). Although most of the disclosed embodiments have referenced the BoPEN scintillator, none of the embodiments are scintillator specific, so any scintillator material can be employed. The described embodiments are also of interest to particle research accelerators. The particle beams used for such research include everything from electron and muon beams, to rare isotope and exotic heavy-ion and radioactive ion beams such as highly charged uranium ions beams (e.g., U-238 with a net charge of +92). In addition there are tens of thousands of particle beams used by industry and various versions of these embodiments could find application there.

Embodiments can also be used for external beam radiation therapy ("EBRT") based on high energy photon beams (e.g., MeV gammas and/or X-rays). Embodiments disclosed herein, such as those in FIGS. 8 and 14-22, have advantages over the known ionization chamber beam monitors that find wide application in photon EBRT, with even more advantages for FLASH therapy. These advantages over ionization chambers include up to two orders-of-magnitude faster beam profile imaging time (e.g., ~10 µs vs. 1000 µs), at least one order-of-magnitude better intrinsic 2D position resolution (e.g., ~0.03 mm vs. 1 mm), and more than one order-of-magnitude higher dose rate capability (e.g., ~5,000 Gy/s vs. 120 Gy/s). Although all of the light-tight ambient pressure beam monitor enclosures shown in FIGS. 8 and 14-22 are rectangular in shape, this is not a requirement or a limitation, and thus other shaped enclosures can be employed such as cylindrical shaped beam monitor enclosures. In addition, the thickness of the above referenced ionization chambers and the scintillator based UFT beam monitor can be almost the same, depending upon specifications.

The highest performance cameras with the largest sensor size, best low-light sensitivity, highest bit depth (i.e., pixel gray scale range), highest frame rates, most sophisticated embedded FPGA circuitry, and thus the highest data transmission output in terms of MB/s, consume the most power. The maximum power consumption for such cameras could be on the order of ≥10 watts per camera, although the standby power when the camera isn't running would likely be much less depending upon the camera. And for smaller cameras, such as those used for the images in FIGS. 23 and 24, the average power consumption was only ~2 watts. Nevertheless, for the case of higher power consumption cameras operating in a sealed enclosure, heat generation followed by heat build-up could potentially be a problem if not adequately addressed.

Several solutions exist to the potential problem of heat build-up, including the use of a series of internal baffled air-vents with staggered holes to block light leaks, as for example in FIG. 25, that would allow cooling by natural air convection. The total thickness of such vents need not be more than 2-3 cm. If necessary this concept can be augmented by forced convection if coupled to one or more miniature fans (e.g., 2-inch to 4-inch blade diameter) for forced-air cooling. A minimum of two such vented light baffles would be required, preferably attached to opposite sides of the scintillator box enclosure—i.e., an entrance baffle for air/oxygen in-flow, and exit baffle for air/oxygen out-flow. The FIG. 25 (Side View) drawing uses dashed arrows to illustrate the air flow through the staggered holes of the light baffle vent from entrance 2501 to exit 2502. The purpose of the light baffle is to facilitate continuous circulation and exchange of cool ambient air flow through the scintillator box enclosure, or of cold gas such as cryogenically cooled nitrogen, or of oxygen enriched air, or even pure oxygen circulation through the scintillator box enclosure, while preventing or minimizing light leakage. The motivation for oxygen circulation in the scintillator box enclosure is that oxygen diffusion into the scintillator can potentially minimize scintillator radiation damage by facilitating partial recovery or repair of scintillator damage by oxygen scavenging of radiation damaging free-radicals created in the scintillator by the incident ionizing radiation beam.

Alternatively the light-tight enclosures can be sealed around the camera lenses, with the camera body protruding out of the light-tight enclosures and thereby venting the camera heat to the external ambient open-air environment. For the 6-way-cross systems, a custom short nipple can be made with a light-tight seal (e.g., double O-ring) to the camera lens, thus leaving the camera body protruding outside and beyond the nipple flange to the external atmosphere. There is also the option of using active cooling of the camera or silicon image sensor, or even cryogenic cooling, as some cameras are sold with thermoelectric cooled sensors. Finally, each camera and/or sensor could be calibrated for their signal response or drift as a function of temperature, and then the temperature of the camera or sensor in its enclosure monitored and its signal response automatically corrected by software.

For the detection of neutrons in EBRT applications, the two most obvious locations for a neutron beam monitoring system might be: (1) immediately after the Li target, but before the moderator, where mostly slow neutrons but perhaps some fast neutrons (e.g. ~0.8 to 1 MeV) are typically generated by a ~2.6 MeV proton beam, and (2) at a location after the moderator where the neutron energy is degraded for many boron neutron capture therapy (BNCT) treatment regimens to the epithermal energy range but more broadly across the range from thermal to slow or even fast neutrons. If only one neutron beam monitor is to be employed, the most important location would be right after the moderator and in front of the patient. Recent trials in Finland suggest that 1-30 keV "slow" neutrons constitute a practical energy range for BNCT treatment. Essentially all of the beam monitor embodiments disclosed herein should work well for the detection and monitoring of neutrons created immediately after the Li target in location (1) above, where the neutron intensity of the BNCT machine is estimated to be on the order of ~$10^{13}$ n/s, corresponding to about $5 \times 10^{13}$ scintillating photons per second from a 0.2 mm thick BoPEN film. Therefore a much thinner scintillator film can be used to minimize interaction with the beam, and still produce a huge amount of scintillating light. For example, a 12 µm thick BoPEN film scintillator should yield about $3 \times 10^{12}$ scintillating photons per second. However, for beam monitoring in location (2), the added moderator plus energy filtering greatly reduces the number of epithermal neutrons by at least several orders-of-magnitude, which are significantly more difficult to detect anyway due to their lower energy than the more energetic "slow" neutrons in location (1). This means that for neutron beam monitoring after the moderator, $B^{10}$ or another high neutron cross-section isotope (e.g., $Li^6$ or Gd) loaded scintillator is required to increase the deposited energy in the scintillating host. Such scintillators are available in plastic sheets and can be incorporated in the scintillator-frame embodiments disclosed above and shown in FIGS. 11-22.

For BNCT head and neck EBRT therapy, the patient's head is typically positioned very close to the neutron beam exit nozzle, and therefore the thinnest profile beam monitors are required corresponding to the largest camera-lens angles with respect to the scintillator normal (e.g., 60°-70°). Modified versions of FIGS. 14-19 with camera angles of ≥60° have been designed for such applications with total beam monitor thicknesses of ~6 cm to 8 cm (i.e., from entrance to exit window), which is almost the same thickness as an ionization chamber. These embodiments (not shown) look similar to FIGS. 14-19, just thinner due to the more severe average camera-lens angle of ~60°-70° as compared to the ~45° angle in FIGS. 14-19.

For the above disclosed neutron beam monitors, several high neutron cross-section isotope loaded scintillators are available, such as Eljen EJ-254 or Saint-Gobain BC-454 which are both $B^{10}$ loaded plastic PVT-based scintillators, or cerium activated $Li^6$ doped silicate glass scintillators from Saint-Gobain, although $Li^6$ doped plastics have also been fabricated. For the various neutron capture therapy ("NCT") applications, including both BNCT and GdNCT (gadolinium-NCT), the neutron beams employed span the energy range from thermal-NCT to fast-NCT (also called FNT), but most NCT programs appear to be based on epithermal-NCT. Unfortunately all of these neutrons are also more damaging to the scintillator material than protons and/or photons, and therefore scintillator replacement would need to occur much more frequently. For this reason the internal calibration scheme employed in the above embodiments is important for the successful implementation of neutron beam monitors, and the fact that scintillator replacement and internal calibration could be accomplished within minutes would be even more beneficial for NCT than for proton or photon EBRT due to more frequent replacement. One method to prolong the useful lifetime of the boron doped scintillator, and therefore not have to replace it as often, is to integrate a motorized X-Y translation stage into the beam monitor enclosure structure and thereby translate the entire system in the X-Y plane in relatively small steps as required, thus moving it around the isocenter and lengthening the period between scintillator replacement—this strategy is conceptually similar to moving the scintillator-frame in small steps in the 6-way-cross via the previously described push-pull linear positioners.

A general complication associated with scintillators for neutron detection is that most neutron sources also generate gammas, and scintillators that detect neutrons will therefore also detect gammas. Most applications, be they medical imaging or homeland security, require neutron detection systems that can effectively discriminate between gammas and neutrons. The disclosed beam monitor embodiments in FIGS. 18 and 19 can effectively provide such discrimination for NCT applications such as BNCT and GdNCT, as well as for other applications such as homeland security. The method by which this can be achieved is to use two different scintillators, as configured in FIGS. 18 and 19, where for example the scintillator on one side (e.g., entrance window) such as 1862 and 1962 respectively might consist of either a thin BoPEN film or a conventional polyvinyl toluene ("PVT") or polystyrene ("PS") based gamma/ion scintillator, with the scintillator on the opposite side (e.g., exit window) such as 1860 and 1960 respectively being a neutron sensitive scintillator such as the boron loaded EJ-254 based PVT (~5% natural boron) or BC-454 based PVT (~5% natural boron, although 10% natural boron is also available). The method to separate the neutron generated image/signal from that produced by gammas is to digitally subtract the image/signal generated by the 1862 or 1962 scintillator from that generated by the 1860 or 1960 scintillator. Such a design will mimic or behave as though it has a high level of gamma to neutron discrimination.

In looking into scintillator damage by neutrons, the issue of radiation damage to the beam monitor cameras was also investigated. Experiments indicate that the slow radiation damage over a period of years to the patient viewing cameras in proton therapy treatment rooms is primarily due to neutrons. The main source of these neutrons is not from the proton beam system, although some neutrons are generated in the collimator, but from the patient's interaction and absorption of the proton beam itself—i.e. primarily where the proton beam stops at the tumor site inside the patient. Radiation damage to digital cameras has been studied extensively for the imaging sensors used in space astronomy (mostly CCDs), as well as for other situations in which high neutron fluxes are created and monitored by cameras such as for fusion research. It has been found that although shielding of cameras can be helpful, it is also not so straightforward. One solution is the direct cooling of the camera sensor to about −20° C. or colder, which also eliminates the camera as a heat source and thereby reduces thermal heating causing calibration drift not only of the camera, but also of the UV-LEDs, UV-photodiodes, and possibly even the scintillator response itself.

Camera sensors/electronics are prone to neutron damage because silicon is typically doped with boron to achieve p-type silicon. However, p-type silicon can also be produced by doping with gallium ("Ga") instead of boron, and in this way fabricate radiation-hardened silicon devices. Both radiation-hardened and radiation-tolerant semiconductors, including CMOS image sensors and cameras are available from several sources, as such sensors and cameras are required for a number of applications including military, aerospace, scientific, and nuclear energy. With conventional boron doped silicon devices, the primary camera visual damage due to neutrons is the creation mostly of "bright" pixels in the silicon image sensor. The "bright" pixels caused by rad-damage are high dark-current pixels or "hot-pixels". Some embodiments replace the cameras in the beam delivery room every couple of years. The majority of neutrons created are scattered in the proton beam momentum direction, which is towards the opposite side from where the patient is being irradiated and thus towards the back of the room. However the entire room is effected by the scattered neutron field and some neutrons will backscatter towards the cameras located at the beam nozzle exit and in front of the patient. Frequent internal calibration of the beam monitoring system will identify the radiation damaged pixels, and so their contribution to the image analysis can be conveniently eliminated by software. Partial neutron shielding of the cameras can be achieved by several means, including the use of boron doped transparent plastics in front of the camera body and lens, similar to commercially available 5% boron doped PVT plastic scintillators but without the addition of a fluor dopant. Since the cameras themselves are located out of the direct beam path, the entire light-tight camera box enclosure, excluding the entrance and exit window areas, can be fabricated out of a neutron shielding metal sheet such as a boron-aluminum alloy like BorAluminum from Ceradyne (~4.5% to 8% by weight of B-10 isotope) or AluBor (10% by weight of natural boron) from S-DH, or a boron clad aluminum such as BORAL or BORTEC. Also boron composite plates made with boron fiber can be used. Alternatively, a number of small shielding plates can be strategically placed around each camera body. Another solution for shielding the front of the camera from neutrons is to use a thick, high boron content transparent borosilicate glass (e.g., 3-5% boron) in front of the camera lens, and maybe in front of the entire camera body. There are many borosilicate optical glasses, but Schott N-ZK7 (15% $B_2O_3$ by wt.), N-BK10 (13% $B_2O_3$ by wt.) and N-BK7 (10% $B_2O_3$ by wt., also referenced as Borkron) with 4.7%, 4.0% and 3.1% boron respectively (by weight), or Schott BOROFLOAT-33 with 4.0% boron (i.e., 13% $B_2O_3$) are all readily available as is Corning 7740 glass (Pyrex) which is 12.6% $B_2O_3$. However BOROFLOAT-33 being much more economical than other borated glasses is sold for neutron shielding in thicknesses up to ~25 mm. It is noted that extremely high $B_2O_3$ and $Gd_2O_3$ glasses have been described in the patent literature such as Application PCT/JP2013/069578 which potentially would be more effective. Also a source of heavily doped boron and lithium polyethylene sheets, bricks and rods/cylinders is Shieldwerx (a division of Bladewerx LLC), which sells a 30% natural boron doped polyethylene product called SWX-210 (i.e., contains $1.87 \times 10^{22}$ boron atoms per $cm^3$) as well as a 7.5% natural lithium doped polyethylene product SWX-215. The disadvantage of boron doped neutron shielding materials is that each neutron captured by boron generates a 0.42 MeV gamma ray; however, lithium doped shielding materials do not produce any neutron capture gammas. However the lower neutron capture cross-section of $Li^6$ compared to $B^{10}$, means that a greater thickness of lithium doped material is required than similarly doped borated material.

In terms of neutron damage, at what point the cameras, or possibly just the silicon image sensors, would have to be replaced needs to be experimentally determined, but most likely it will be in years for proton or photon therapy since the internal calibration system can adjust for bad pixels in real-time as they occur. It is also noted that the larger the image sensor pixel size, the less prone it is to radiation damage. For the beamline monitors such as the 6-way-crosses in FIGS. 9-13, the camera can be moved a significant distance away from the beamline and hence the radiation field, with the detrimental effect on photon collection and spatial resolution minimized, by extending the optical system length. This can be achieved via the introduction of a relay lens system including a relay train assembly. The specific design will depend on the distance desired for extending the optical tube length of the camera system. Relay lenses are made to extend the viewing distance for remote viewing and operate by producing intermediate planes of focus. Collecting and dispensing optical images is done with focusing lenses which transport the light pattern via a relay lens or train of relay lenses. Some examples include periscopes, endoscopes, remote inspection and surveillance. A wide selection of relay lenses are commercially available.

Embodiments are directed to external beam radiation therapy ("EBRT") related applications for both particle and photon radiation. For both types of EBRT, the embodiments are directed towards beam monitoring systems designed for use in either of two locations: (1) internal beam monitors located within the accelerator beam delivery system and therefore prior to the beam exiting the system nozzle or snout or collimator, or (2) external beam monitors located outside the accelerator beam delivery system after exiting the system nozzle or snout or collimator and thus positioned after the delivery system exit and in front of the patient.

Embodiments can further be used for a variety of industrial and scientific beam monitoring applications such as ion implantation accelerators (e.g., depending on ion, typically >0.3 MeV), and nuclear physics particle accelerators. Typically ion beam implantation will have the most stringent detector/monitor design requirements with regard to beam transparency, as the ion particle energies are frequently below 1 MeV and the particles themselves are typically highly ionized, heavy nuclei. Many accelerators used for nuclear physics also operate at relatively low to medium ion energies, so the same beam monitor concept in accordance to embodiments can be used for both applications. Some additional advantages of the described embodiments include the relative low cost of the beam monitor critical hardware, and the low cost lifetime operational/maintenance expense which includes the minimal overhead expense associated with the ultra-fast internal calibration system, as compared with the time consuming calibration cost for conventional systems. This benefit is also important for scientific applications (e.g., nuclear physics) that subject other detectors/monitors to costly maintenance and radiation damage replacement expenses.

The therapeutic benefits of embodiments of UFT beam monitors disclosed herein are particularly useful with "FLASH" irradiation therapy in which short pulses (≤0.5 second) of radiation are delivered at ultrahigh dose rates of ≥40 Gy/s (i.e., FLASH) compared to conventional dose rates of ≤0.03 Gy/s in single doses over a period of ≥60 seconds. FLASH radiotherapy may well result in a paradigm shift in the treatment of cancer as ultrahigh dose rates appear to increase the differential response between normal and tumor tissue, thus increasing the lethality to malignant cells while not significantly increasing damage to healthy cells. In order to monitor the FLASH beam in real-time, the much faster beam profile imaging time and readout capability, greatly improved intrinsic 2D position resolution, and the much higher dose rate capability of the described UFT beam monitors yields order-of-magnitude advantages when compared to conventional ionization chambers, and in this sense appears to be an unexpected enabling technology.

Figure 28A:
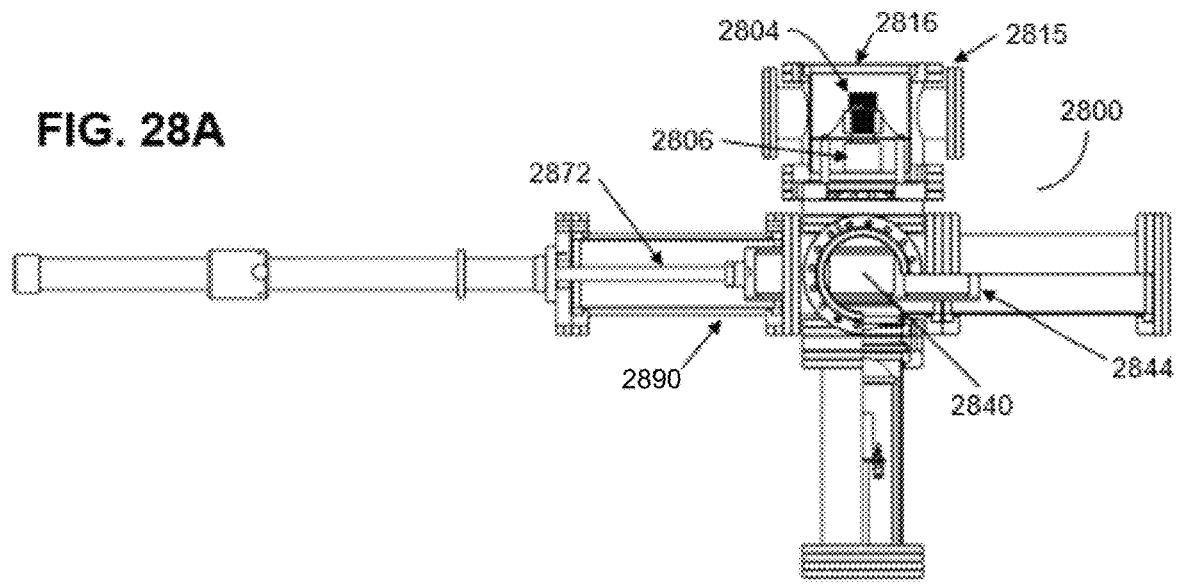
FIGS. 28A-C illustrate a system that includes a scintillator-frame beam monitor holding three separate scintillator films in a 6-way-cross vacuum chamber with a camera in an attached 4-way-cross open system capable of actively or passively cooling the camera in accordance with embodiments.
Figure 28B:
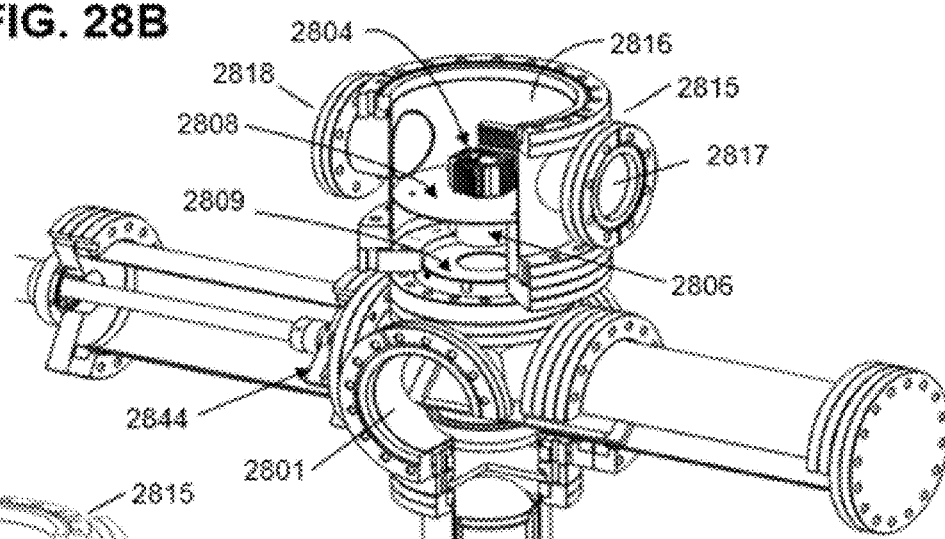
Figure 28C:
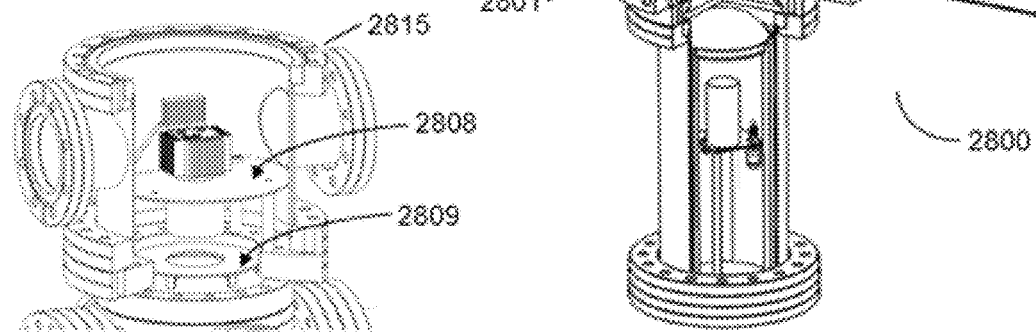

Additional embodiments for beamline monitors based on the 5-way and 6-way-cross configurations previously described in FIGS. 6-13 and FIG. 27 are now disclosed. Specifically, FIGS. 28A-C illustrate a system that includes a scintillator-frame beam monitor holding three separate scintillator films in a 6-way-cross vacuum chamber with a camera in an attached 4-way-cross open system capable of actively or passively cooling the camera in accordance with embodiments. FIGS. 28A-C illustrate a system 2800 that includes a segmented ladder type of scintillator film holder 2844 in FIG. 28A which can hold at least several different scintillator frames 2840 that can be pushed into the beamline center from left to right by the push-pull linear positioner 2872 which is enclosed in a nipple 2890. The segmented ladder scintillator film holder embodiment shown in FIGS. 28A-C holds three scintillator frames, but in other embodiments can hold more if each scintillator frame is either smaller as in FIG. 29A, or if the nipple length is longer and can accommodate a larger size segmented ladder. The embodiment shown in FIGS. 28A-C includes a larger tube diameter 4-way-cross 2815 attached to the vacuum viewport assembly at the top of the smaller tube diameter 6-way-cross. The larger tube diameter 4-way-cross assembly encloses the machine vision camera 2804 with attached lens 2806. FIG. 28B is a perspective view of system 2800, in which the camera body 2804 is attached to heat sinks on four sides for passive cooling of the camera body. FIG. 28B shows two of the flanges 2817 and 2818 left open of the 4-way-cross with top flange 2816 also left open for natural passive convective air cooling over the cooling fins of the camera heat sinks. However, for more efficient active cooling of camera 2804, the larger tube diameter 4-way-cross of FIGS. 28A-C is designed so that it has enough room to accommodate an active cooling system such as a Peltier TE (i.e., thermoelectric) cooling assembly. For active cooling, the 4-way-cross 2815 can accommodate two fans (not shown) attached to the side flanges 2817 and 2818, with a larger size, third fan (not shown) mounted to the top flange 2816. These fans can operate either in the blower or exhaust modes and most likely will be some combination of both with cool air being blown in and hot air being exhausted out. Using a relatively inexpensive 50-watt Peltier TE active cooling fan assembly in experimental testing, a test camera sensor board temperature was reduced by ~25° C. which is important to reducing sensor noise when taking long camera exposures. If more effective camera cooling is required, then instead of the larger tube diameter 4-way-cross as described above, a 6-way-cross could be used instead, which would provide two additional flange openings for either more efficient air circulation by convection or two additional ports for active fan cooling on all four sides of the camera body.

Also, by using even larger tube diameters, then multiple Peltier TE active cooling fan assemblies could be used.

For beam monitors that employ polymer based scintillators such as described herein, that are to be used or inserted in an ultra-high vacuum (UHV) beamline such as in the 6-way-cross CF-flanged systems described above, the polymer based material (depending on its composition and surface area) could have too high an outgassing rate to be UHV compatible. In order to reduce the outgassing rate from such scintillator polymer films to a manageable level, they could be effectively encapsulated or "sealed" and made UHV compatible by coating both the front and back film surfaces with an optically transparent, low outgassing, thin-film layer (e.g., ≤0.5 µm thickness) such as $Al_2O_3$. Alternatively, if one side of the polymer scintillator is thin-film metallized, for example to create a reflective back surface and thereby enhance photon emission out of the front surface, then only the photon emitting surface would need to be thin-film "sealed" as described above with a coating such as $Al_2O_3$.

The perspective drawing of FIG. 28B provides a good view of the 6-way-cross 2801 entrance flange through which the particle beam enters as it passes through the center scintillator frame. Also shown in FIGS. 28B and 28C is the camera light-blocking disk/plate 2808 located between the camera body 2804 and camera lens 2806, which blocks light that can enter the 4-way-cross through the open flanges 2816-2818 from finding its way into the camera though the lens 2806. The UV-light generated from a UV-source (not shown) such as a UV-LED attached to the support ring 2809 can be blocked from reaching the camera sensor by a UV-blocking and visible transmitting filter (not shown) attached to the camera lens 2806. Also attached to the support ring 2809 is a UV-photosensor (not shown) such as a UV-photodiode for each UV-source for monitoring and/or calibrating the UV-source intensity. FIG. 28C provides a frontal perspective view at a different angle of the 4-way-cross 2815 that encloses the camera assembly.

Figure 29A:
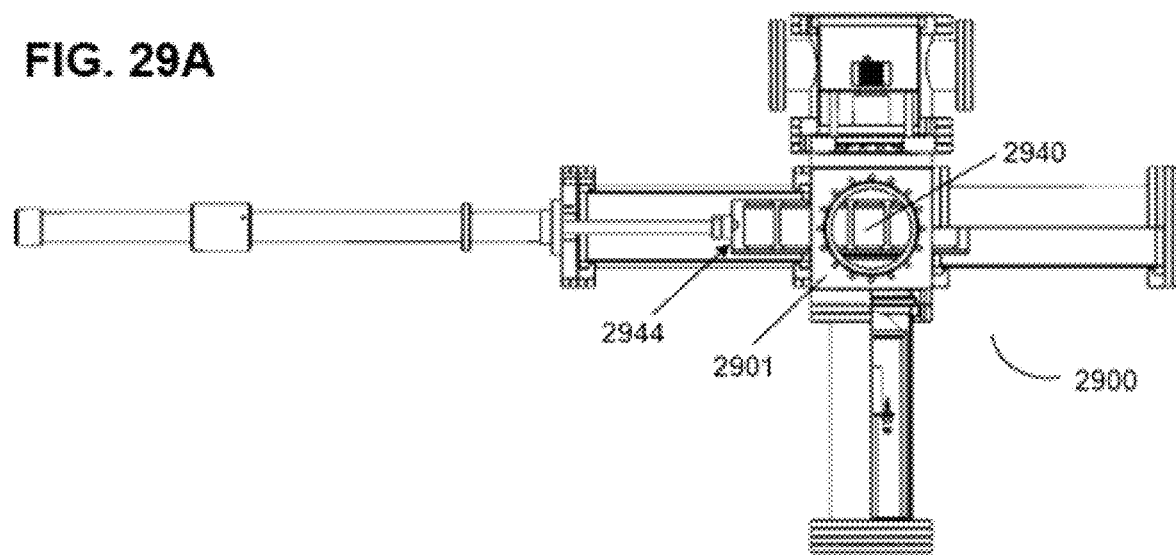
FIGS. 29A-B illustrate a system that includes a scintillator-frame beam monitor holding six separate scintillator films in a 6-way-cube vacuum chamber with a camera in an attached 4-way-cross open system capable of actively or passively cooling the camera in accordance with embodiments.
Figure 29B:
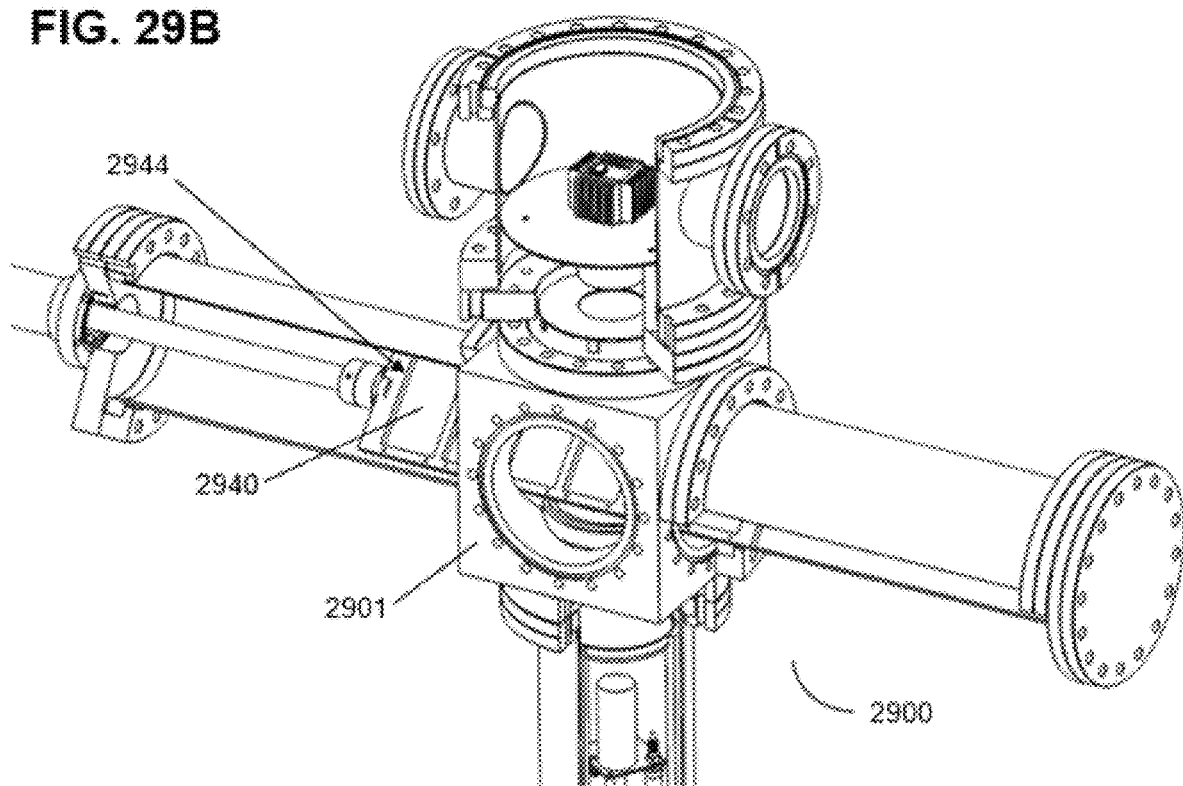

FIGS. 29A-B illustrate a system that includes a scintillator-frame beam monitor holding six separate scintillator films in a 6-way-cube vacuum chamber with a camera in an attached 4-way-cross open system capable of actively or passively cooling the camera in accordance with embodiments. The embodiment shown in FIGS. 29A-B illustrates a system 2900 that is similar to that described for FIGS. 28A-C, and shares most all of the same component/element features, but with the following differences. Instead of system 2900 being based on the 6-way-cross 2801 in FIG. 28, it is based on a 6-way-cube 2901. Further, the segmented ladder type of scintillator film holder 2944 in FIGS. 29A-B is shown to hold six different scintillator frames with each scintillator frame 2940 having a smaller scintillator area as can be seen in comparing the scintillator frame area in FIG. 29A to that in FIG. 28A. Otherwise the component descriptions for system 2800 apply to system 2900. The primary advantage of the 6-way-cube structure is that four of the six sides provide closer access to the center of the beamline than in the 6-way-cross and therefore results in a more compact structure that can potentially be an advantage in allowing closer placement of the camera and PMT to the scintillator. However, depending on the application, the cube based structure can also be a disadvantage in terms of a somewhat shorter length for the segmented ladder scintillator film holder and the fact that there can be no rotatable flanges built into the 6-way-cube, whereas the 6-way-cross can have one or two rotatable flanges on each axis.

The camera used for the photograph of FIG. 26 was a Basler Ace acA2040-120 um with 8.9 mm diagonal (i.e., 7.1 mm×5.3 mm) 3.1 MP resolution CMOS image sensor, corresponding to a 1/1.8" image circle. The lens used was relatively inexpensive $75 lens (i.e., not a macro lens) having a matching 1/1.8" image circle with an aperture of F/2 and a focal length of 4 mm. The lens front optical element was ~110 mm from the target center (i.e. working distance) on exactly a 45° line. However, the horizontal line of the 10 cm outlined square at the bottom of FIG. 26, which could represent the top of the scintillator film closest to the camera in FIGS. 28A and 29A, was only ~87 mm from the lens front optical element yet remains in focus even given the large perspective tilt distortion and close focus distance. In this regard, the maximum size scintillator film 2840 in FIG. 28A that can be viewed through the 8.9 cm diameter viewport window of the 6-way-cross 4" tube O.D. in FIGS. 28 and 29 is ~7.6 cm×8.2 cm. Given the excellent depth-of-field at this close working distance, which is compatible with the embodiments illustrated in FIGS. 28 and 29, an analysis of this figure/photograph indicates that a conservative estimate of the image position uncertainty or position accuracy is one-half the calculated camera sensor pixel field-of-view (FOV) and for this camera-lens combination at this 110 mm working distance the calculated pixel full FOV is 92 µm, so one-half would be 46 µm. However, much higher pixel resolution cameras are available with CMOS sensor resolutions in the range of 12-25 MP, which would yield a much smaller FOV with significantly better position accuracy.

Figure 32:
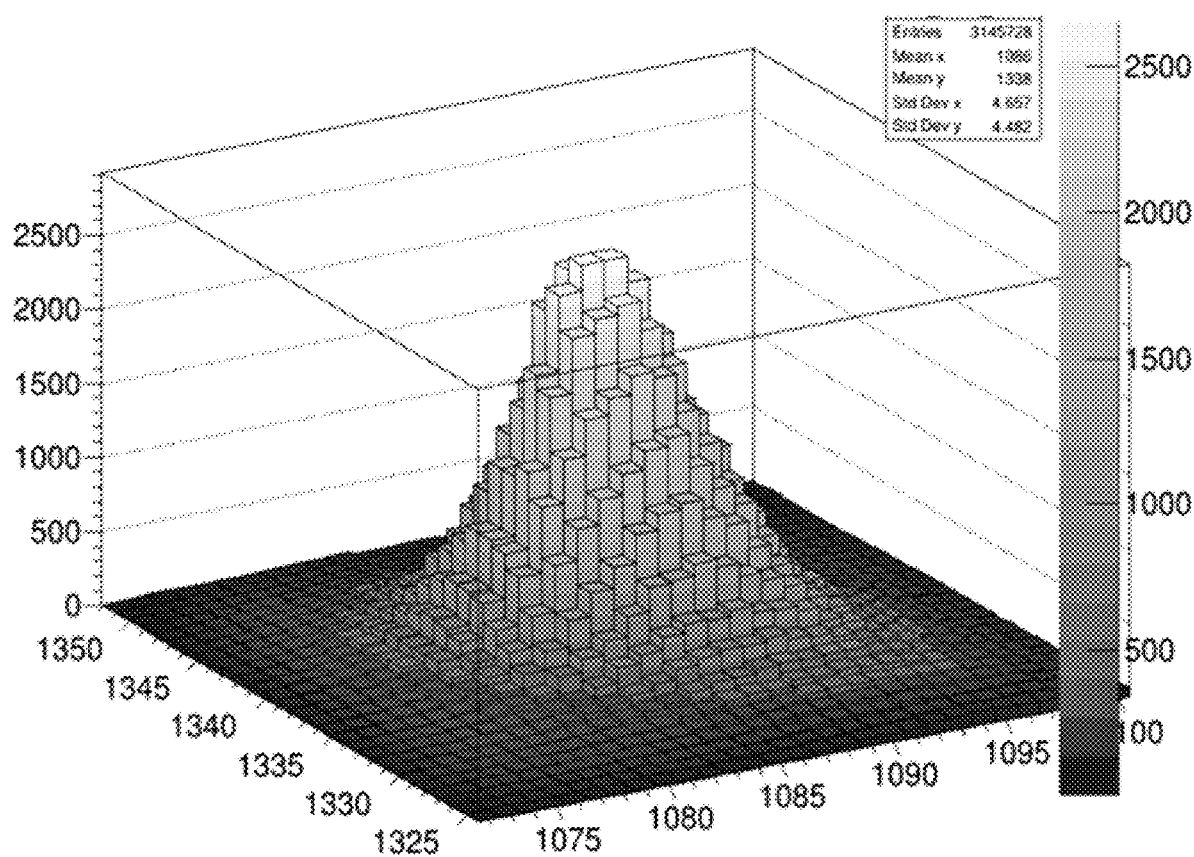
FIG. 32 is a beam position, shape and intensity profile image using the same 3.1 MP camera as used in FIG. 26, photographed off an oscilloscope scintillator screen of an orbiting electron beam captured in 21 µs to minimize movement blur in accordance to embodiments.

As can be seen in FIG. 26, a 7.6 cm×8.2 cm rectangular area would fit roughly midway between the 5 cm and 10 cm outlined squares and would therefore fall well within the field-of-view and the depth-of-field focus of the described camera-lens system. However, for a confined beam such as in the 4" tube in FIG. 28A with a 7.6 cm×8.2 cm object field, a higher resolution camera than used for FIG. 26 could be employed. An example of one such camera is the 12.2 MP Basler acA4024-29 um combined with an 8 mm focal length lens at a working distance of 100 mm, which could achieve a full pixel FOV of ~21 µm. If used with a tightly focused, stationary beam such as an electron beam confined to a 2" tube, then the same 12.2 MP camera combined with a longer 16 mm focal length, high resolution lens (e.g., ~150 line-pairs/mm), at the same 100 mm working distance should realize a full pixel FOV and resolution of ~10 µm, corresponding to an absolute position accuracy of ~5 µm. For example, FIG. 32 is a reconstructed image showing the beam position, shape and intensity profile of a circularly orbiting electron beam photographed off of an oscilloscope scintillator screen and captured in 21 µs to minimize the beam image blur caused by the circular beam movement in accordance to embodiments. The pixel field-of-view is ~30 µm with an estimated 2-3 µm spatial resolution. The 3D image in FIG. 32 employed the same 3.1 MP machine vision camera (i.e., 2048×1536 pixel CMOS sensor) as used in FIG. 26, but with a 6.1 mm focal length lens and demonstrates that such a camera-lens system as in many of the embodiments described herein is capable of capturing particle beam images in real-time off of a scintillator film providing not only the beam position and half-bandwidth (i.e., FWHM), but the full band shape and intensity profile over 3 orders-of-magnitude (i.e., 12 bits) and thereby also capturing the beam tail. An analysis of FIG. 32 indicates that the image position accuracy is ~15 µm corresponding to one-half the full pixel FOV. The FWHM for this figure is ~10 pixels corresponding to ~300 µm. The beam position is defined in FIG. 32 by its two-dimensional (2D) location in terms of its X and Y pixel coordinates in the figure legend which can be calibrated to its absolute location on the scintillator screen. The beam centroid center-of-gravity position, as well as the beam width from the calculated Gaussian fit, was determined to have about a 2-3 µm spatial resolution and with a higher pixel resolution camera the reconstructed image position and width uncertainty can likely be reduced to within ≤1 µm.

As discussed above, FIGS. 26 and 32 provide visual confirmation that the transmissive ionizing-radiation beam monitoring system embodiments described herein for EBRT applications, such as those illustrated in FIG. 14-22 and FIG. 30, are optically capable of generating high resolution beam images. Given the same size camera CMOS image circle of 1/1.8", but at the longer average working distance of ~170 mm for the folded optical path of each camera in FIG. 30 as compared to the 110 mm in FIG. 26 that was used to replicate the approximate working distance in the 6-way-crosses shown in FIGS. 28 and 29, the field-of-view will be proportionately larger and will more than cover the larger scintillator areas in the aforementioned EBRT figures and embodiments such as in FIG. 30. A reasonable full-size scintillator area for the EBRT applications could be on the order of about 26 cm×30 cm, but if covered by four cameras each focused on one quadrant as in FIGS. 17, 19, 20 and 30, the minimum field-of-view for each camera would be 13 cm×15 cm which can be seen as partially covered in FIG. 26 at a working distance of just 110 mm. Even without going to a larger CMOS sensor camera, the longer average working distance of 170 mm in the referenced figures will allow the same camera-lens setup to more than cover this larger scintillator area even when taking into account that the closest distance from the camera lens to the top scintillator horizontal edge will be ~130 mm. In fact, the optics work out that a somewhat longer focal length lens with a higher pixelated camera CMOS sensor could be used to realize better pixel resolution than for the previously referenced 4 mm focal length lens.

Figure 30A:
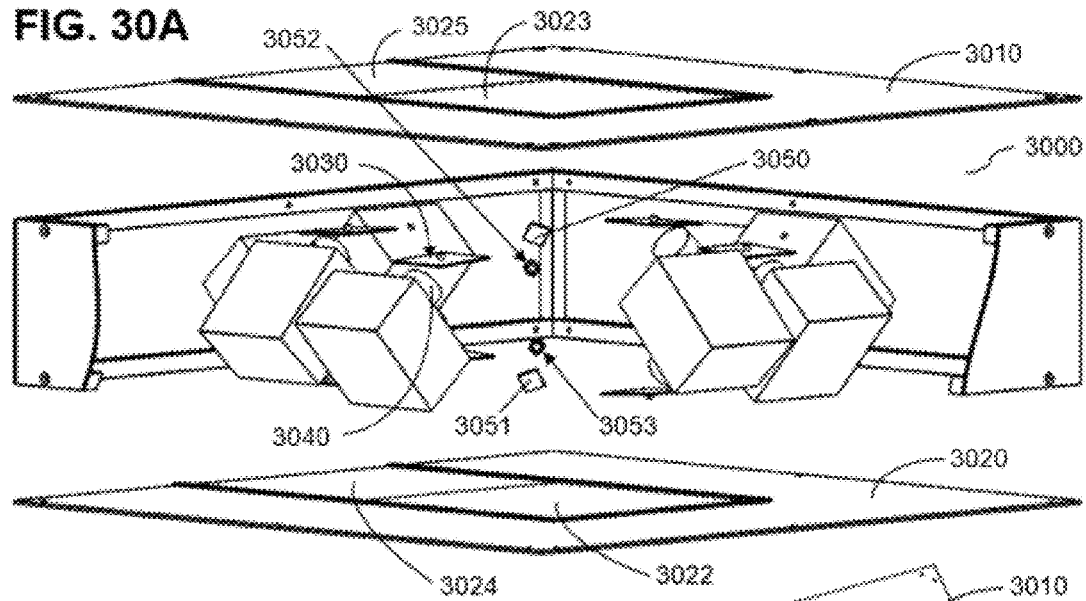
FIGS. 30A-C illustrate a system that includes an eight camera, full-size double window/scintillator sliding-frame module beam monitor in a light-tight slim enclosure in accordance with embodiments.
Figure 30B:
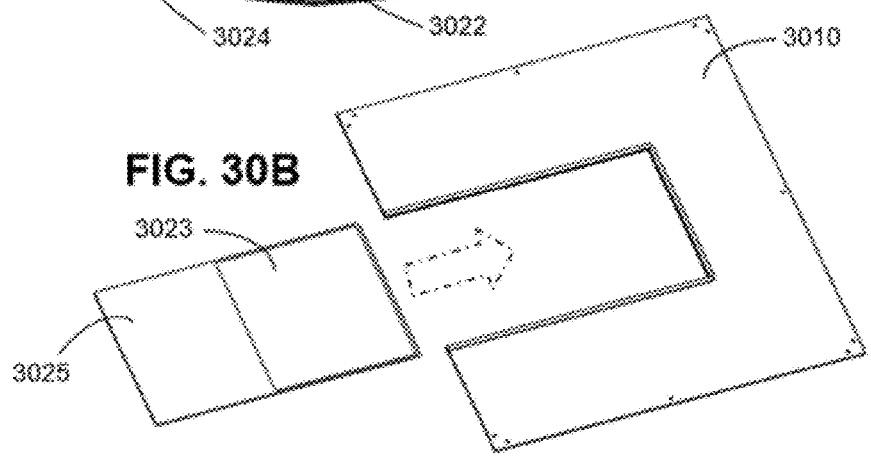
Figure 30C:
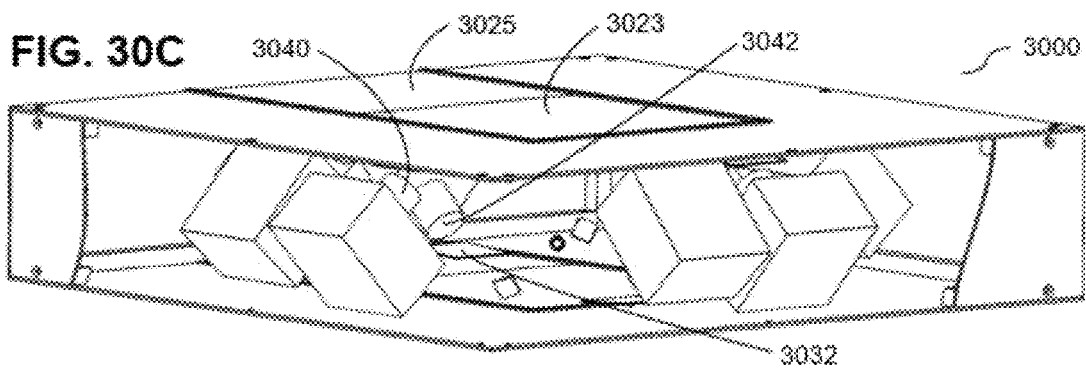

FIGS. 30A-C illustrate a system that includes an eight camera, full-size double window/scintillator sliding-frame module beam monitor in a light-tight slim enclosure in accordance with embodiments. The embodiment illustrated in FIGS. 30A-C, which illustrates system 3000, is similar to that for system 1900 as shown in FIGS. 19A-B and shares most all of the same features, but with a few important differences. Both systems 1900 and 3000 illustrate an eight camera, full-size double window/scintillator frame module beam monitor in a light-tight slim enclosure in accordance with embodiments. Although the eight camera-lens units are arranged somewhat differently in the two systems, both systems employ four cameras per scintillator, with one mirror 3030 and 3032 in close proximity to each camera lens 3040 and 3042 as shown respectively in FIGS. 30A and 30C, and with all eight mirrors located out of the incident ionizing radiation beam path and obliquely facing both the lens and the scintillator at an angle. Thus each machine vision camera-lens unit and its associated close proximity mirror comprises a folded optical system configuration with respect to its view of one section or quadrant of the scintillator surface to reduce a thickness or depth of the light-tight enclosure with a projection of its optical axis oriented at an angle of incidence of 45°±35° to a surface of the scintillator. Further, both systems are designed so that they can accommodate one or more UV-sources (e.g., UV-LEDs) 3050 and 3051 in FIG. 30A and one or more UV-photosensors (e.g., UV-photodiodes) 3052 and 3053 in FIG. 30A for internal system calibration which includes monitoring each scintillator for radiation damage. A major difference between systems 1900 and 3000, besides the different camera arrangement, is in the design of the entrance and exit window/scintillator frame module systems. In system 1900 the two window/scintillator modules 1962 and 1960 can be replaced from outside the light-tight enclosure as illustrated in detail in the embodiment shown in FIG. 14B. More specifically, the outer retaining frame 1410 is first removed and then the window/scintillator replacement module 1460 is dropped into the recessed frame of the cover plate 1414 with the outer retaining frame 1410 then replaced. However, for the embodiment in FIGS. 30A-C, the window/scintillator module 3023 is attached to the sliding plate frame 3025 and then the combined window/scintillator plate assembly is slid into a track or channel in the top cover plate 3010 as shown by the dotted arrow in FIG. 30B and viewed in FIGS. 30A and 30C. The same design for replacement of the window/scintillator in the bottom cover plate 3020 is also shown in FIG. 30A in which window/scintillator module 3022 is attached to the sliding plate frame 3024. The advantage of the sliding window/scintillator system in which access and replacement of the window/scintillator module occurs from the side of the light-tight slim enclosure, is that for many EBRT systems it might not be easy to gain access to the front or back cover plates for fast window/scintillator replacement.

The dual scintillator beam monitoring system 3000 illustrated in FIGS. 30A and 30C, as well as systems 1800 and 1900 illustrated in FIGS. 18A-B and 19A-B, with each scintillator optically coupled to its own set of cameras and integrated with its own computing platform, be it via camera embedded FPGAs, frame grabbers or computers, comprise two independent beam monitoring detection units within a single enclosure/structure, with each unit having its own real-time data processing and analysis capability. The described embodiments identified as systems 1800, 1900 and 3000 therefore each constitute an integrated system with built-in internal redundancy. However, if so desired the data from the two independent beam monitoring detection units could be combined (i.e., added together) by means of data synthesis and meta-analysis to yield a larger unified/pooled data set with enhanced statistics for improved precision, accuracy and resolution for tracking the beam movement and generating the beam position, beam intensity profile, beam fluence, and external dosimetry.

Figure 31:
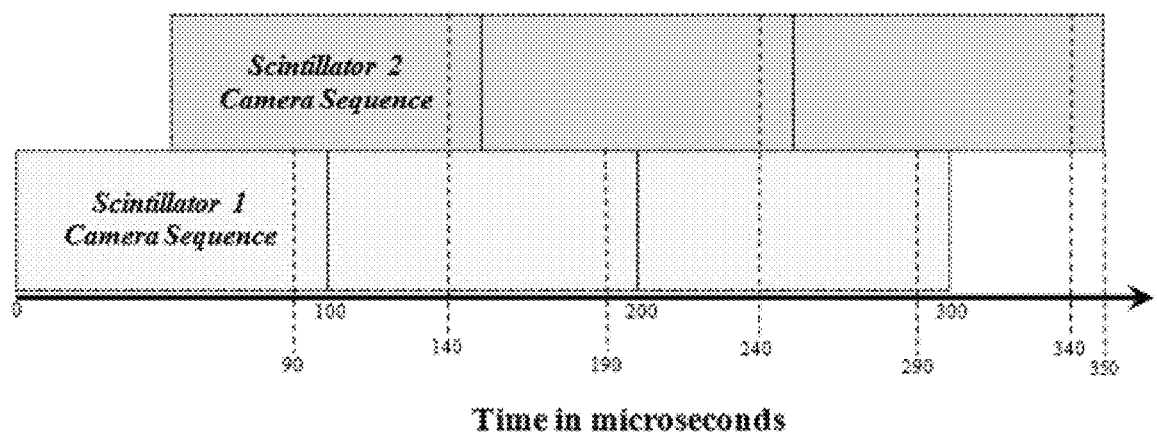
FIG. 31 illustrates a method to avoid loss of data during the readout dead-time in a dual-scintillator multiple machine vision camera system by introducing a time-delay in the camera sensor readout sequence between the two scintillator camera systems in accordance with one embodiment.

FIG. 31 illustrates a method to avoid loss of data during the readout dead-time in a dual-scintillator multiple machine vision camera system by introducing a time-delay in the camera sensor readout sequence between the two scintillator camera systems in which the two sets of cameras are time-shifted in their shutter exposures by approximately one-half of a time-frame so that one set of cameras is always collecting data during the dead-time readout period of the other set of cameras in accordance with one embodiment. The two independent beam monitoring detection units as described immediately above, with their two sets of cameras, can be configured such that their respective data sets are time-shifted in their frame sequences with respect to each other as illustrated in FIG. 31, resulting in the two sets of streaming data being out-of-phase or time-displaced one relative to the other by a fraction of a frame. FIG. 31 shows one such example with each scintillator-camera system operating at a frame rate of 10,000 fps (i.e., frames per second), corresponding to 100 µs per frame and consisting of a 90 is exposure window (i.e. shutter speed) and 10 µs of dead-time allocated to CMOS readout and digitization. In general, a more realistic dead-time would be ≤5 μs with a corresponding shutter speed or exposure time of ~95 μs. By configuring the above two independent beam monitoring detection units with their two sets of partially overlapping time-shifted streaming data by a fraction of a frame as shown in FIG. 31, one set of cameras will always have their shutters open and their image sensors recording emitted photon data from one scintillator during the dead-time sensor readout and digitization period of the other set of cameras associated with the other scintillator. Therefore, by staggering or off-setting the two sets of streaming data in this manner, the short period of total blindness to the incident ionizing-radiation due to the camera image sensor dead-time in one system can be covered and recorded in the second system.

In accordance to embodiments, the entrance and/or exit ultra-thin windows of the beam monitor enclosure can be dark colored or black to minimize internal photon reflections from the emitting scintillator materials and/or UV-LEDs, but can also be a dull or even shiny reflective ultra-thin, low density, low-Z metal such as an aluminum or titanium foil if the internal beam monitor reflectivity is properly calibrated and/or taken into account. Even for a black coated aluminum foil window, continuous exposure to a particle beam could ablate or sputter off some of the black coating which is typically ~2 μm thick and thus reduce photon absorbance and increase reflectivity as a function of integrated beam exposure time and so should necessitate regular monitoring and/or calibration with eventual replacement. This is one reason why the window and scintillator might best be assembled as a single window/scintillator frame module as previously described in which both components (i.e., window and scintillator) can be conveniently replaced at the same time.

In applications for which the particle beam is electrons, because of their low mass relative to a proton, the scattering of the incident electron beam in passing through the beam monitor material is more significant than for protons. Therefore to minimize scattering of an incident electron beam, such as in electron FLASH RT ("eFLASH"), the beam monitor material thickness and density should be as low as possible. In practical terms, for large-area windows (e.g., ~1 ft$^2$) ultra-thin aluminum foils are an excellent choice although titanium foils might be superior because they are stronger and in thicknesses of 0.0005" are essentially defect and wrinkle free which is not true for aluminum foil in this thickness. However a thin-film metal coating (e.g., ~0.1-0.2 μm) on a polymer film base could be even better, especially if also coated black or coupled to an ultra-thin black polymer film. Metallized polymer films with the polymer base being as thin as ~1-2 μm are available in large size continuous rolls with widths on the order of 1 meter, as are black polymer films as thin as ~5 μm, thus a layered composite window of ultra-thin black polymer coupled to a metallized polymer could have a total thickness of ~7 μm, while ultra-thin aluminum foils are commercially available in continuous lengths in roll widths of ~48" to 60" and in thicknesses as small as 6 μm. Black coated aluminum foils are available in thickness of ≥14 μm (i.e., with the foil being ~12.7 μm and the matt black coating being ~1-2 μm). With scintillator films such as BoPEN (biaxially-oriented polyethylene naphthalate) as thin as 3 μm, which have been tested and found to be both satisfactory and highly radiation damage resistant as seen in FIG. 3, the total material thickness of the described embodiments could be sufficiently small so that to first order it could be almost ignored with respect to the beam monitor material contribution to electron beam scattering, beam energy loss and intensity loss for electron based EBRT modalities such as eFLASH. More specifically, for the range of electron energies currently projected for eFLASH (e.g., approximately 4-20 MeV), and with a total minimum beam monitor material thickness equivalent to ~20-35 μm of aluminum, the beam energy loss and electron scattering will be practically negligible in comparison to the energy loss and scattering of the electron beam in passing through 1 meter of air. For example, the energy loss for a 20 MeV electron beam in passing through a 35 μm thickness of aluminum foil will be ~22 keV (i.e., 0.11% loss), as compared to an energy loss of ~305 keV for the same beam passing through 1 meter of air (density of 0.0012 g/cm$^3$ for dry air at 20° C. at sea level). In other words, the energy loss through two aluminum foil windows and a few microns of scintillator film will be just 7.2% of the energy loss for the same beam in passing through 1 meter of air. For a 4 MeV electron beam, the energy loss through the beam monitor will be ~15 keV (i.e., 0.38% loss), as compared to a 222 keV energy loss through 1 meter of air, which corresponds to the beam monitor energy loss being just 6.8% of the energy loss through 1 meter of air.

High energy electron beams generated by linear accelerators (linacs) have been used for almost 50 years to treat cancer by EBRT. As indicated above, the clinical linacs used for electron RT (radiation therapy) generally cover the energy range of 4-20 MeV. The distal depth of 90% maximal dose (d90) for electron-RT corresponding to the 4 MeV to 20 MeV energy range is 1.5 cm and 6.1 cm respectively. For treatment of tumors beyond ~6 cm, clinical electron linacs with energies ≥25 MeV are required but have not been developed for clinical use (e.g. energies of ≥100 MeV might be needed for deep-seated, large, dense tumors in the abdomen and pelvis). To treat such tumors by EBRT, photons/X-rays, protons and ions (e.g., He and C ions) are preferred and clinical machines for both photons and protons have been commercially available for decades. Thus for relatively shallow tumors eFLASH is being pursued and has been demonstrated with very favorable results in the first human test reported in 2019. However, for more deep-seated tumors proton-FLASH and photon-FLASH machines are more appropriate with proton therapy machines now being modified for proton-FLASH for clinical testing.

Novel EBRT modalities continue to be conceived, researched and evaluated for clinical translation and human trials. Therefore, besides the various EBRT modalities discussed above and listed in the "Background Information" section, several novel spatial-temporal modalities including some that can exploit the FLASH effect to some degree with spatial grid separation are being investigated and could benefit by the inventions and embodiments described herein, including GRID, LATTICE, minibeam and microbeam radiotherapy ("RT") in addition to FLASH-RT which has been previously described. For microbeam-RT ("MRT") the ionizing beam used in animal studies has typically had a half-bandwidth on the order of ~25-50 μm with about a 200-400 μm pitch or spacing between adjacent peak centers. The ionizing-radiation has been almost exclusively high energy X-ray photons from one of only a few such capable synchrotron sources in the world. Therefore, for a practical system in a clinical setting a compact, high flux, photon source is needed than can deliver dose rates on the order of 50-100 Gy/s or greater. Several companies and academic groups are pursuing this challenge, but it is still many years in the future and for this reason, protons and heavier ions such as helium and even carbon are being evaluated for MRT because such sources could be easier to develop and have the additional advantage over photons of maximum energy deposition at the Bragg peak with a sharp intensity fall-off thereafter. As a more practical alternative to MRT, proton minibeam-RT (pMBRT) has been demonstrated using typical beam widths in the range of 0.4 mm to 0.7 mm with very favorable results such that preparations for the first clinical trials are now being made in Europe and with heavier-ions also under consideration. One problem with the lightest particles such as electrons and protons for MRT is that they are the most prone to scattering and if having to traverse deep into the body they would scatter or smear so much as to significantly lose their microbeam spatial integrity. Nonetheless, many of the embodiments described herein are capable of meeting the temporal and/or spatial requirements needed for essentially all types of photon and particle EBRT modalities with precise beam position, shape and dose analysis in real-time. As previously discussed, some of the embodiments described using relatively low-cost cameras and lenses in both single and multi-camera beam monitoring systems should be able achieve spatial resolutions on the order of microns depending on the application and the size of the object field. In contrast, there are no existing commercial ionizing-radiation beam monitors with the real-time temporal and spatial resolution that can match that of the embodiments described herein, while also being highly transmissive with large-area capability (e.g., ~1 ft$^2$) and highly radiation damage resistant, all at relatively low cost.

Because of the relative proportionate increase in beam scattering associated with the higher spatial resolution narrow-beam modalities discussed in the previous paragraph, if the ionizing-radiation is electrons or even protons the spatial resolution of the beam can deteriorate rather quickly even in air, and especially for MRT. Since photons scatter much less than electrons or protons, photons have been the ionizing-radiation of choice for MRT with beam diameters on the order of 25-50 μm. For this reason heavier ions than protons, such as helium and carbon are being considered for MRT. Yet even for photons, the beam scattering in the patient can be significant if the tumor is deep-seated. Therefore to minimize the scattering in air for submillimeter spatial resolution multibeam modalities the beam source is generally positioned as close to the patient as possible. This means that for high spatial resolution multibeam modalities there is likely not enough space to place the previously described beam monitors between the radiation source/collimator and the patient. However, by employing a new system configuration and method, the light-tight enclosed beam monitors previously described can be configured for use in patient treatment planning, diagnostics, analysis, dosimetry and quality assurance (QA). The novel method and system embodiment illustrated in FIGS. 33A and 33B describe two versions of system 3300 that can be used with appropriate phantoms to measure beam shape, intensity profile, fluence and dosimetry, as well as loss in beam definition due to scattering and absorption as the beam of ionizing-radiation passes through a patient phantom. The described method and system for treatment planning and patient QA can be used with essentially all EBRT modalities, including the temporal and spatial modalities described above of FLASH RT, LATTICE-RT, GRID-RT, minibeam-RT and microbeam-RT, with photons, electrons, protons and ions, and for streaming images at rates of 10,000 fps (i.e. 100 μs per frame) and beam widths as narrow as 25-50 μm.

Figure 33A:
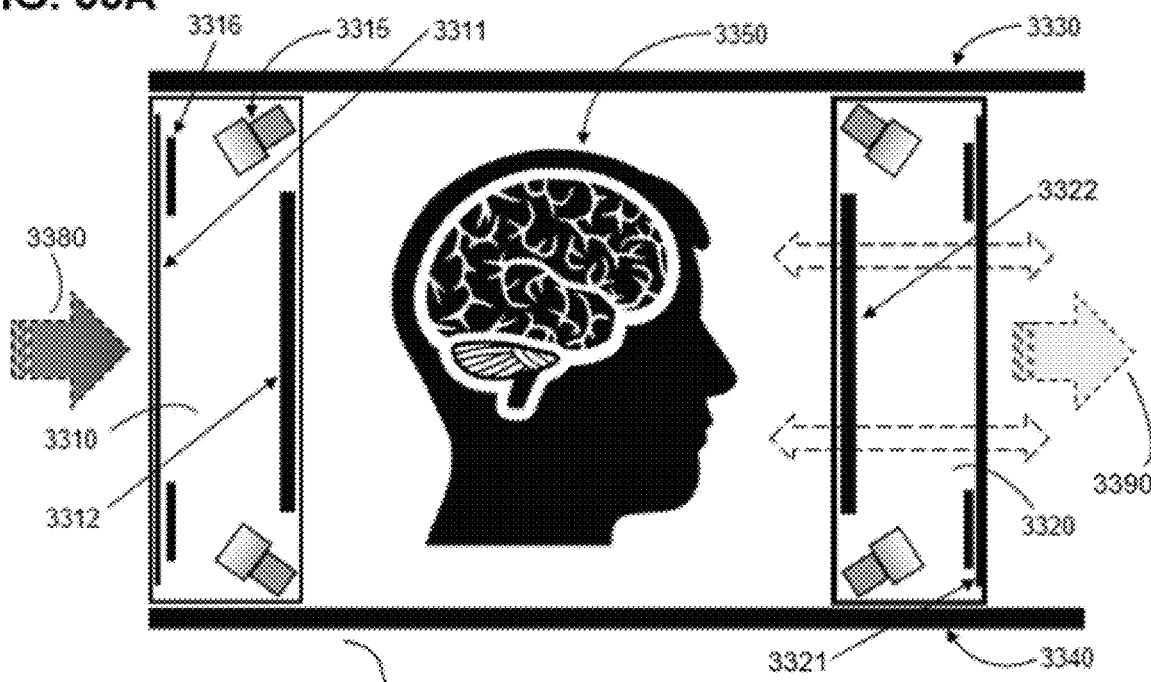
FIGS. 33A-B illustrate a system and method in which an ionizing-radiation beam source with two separated ultra-thin scintillator based multi-camera beam monitors can be used with a patient phantom or material cross-sectional phantom placed between them for patient treatment planning, analysis and quality assurance including 2D measurement of beam scattering, loss of beam quality/sharpness, and beam fluence as the beam penetrates the phantom for both single beam and grid separated multibeam high spatial resolution radiotherapies (RT) such as minibeam-RT and microbeam-RT in accordance to embodiments.
Figure 33B:
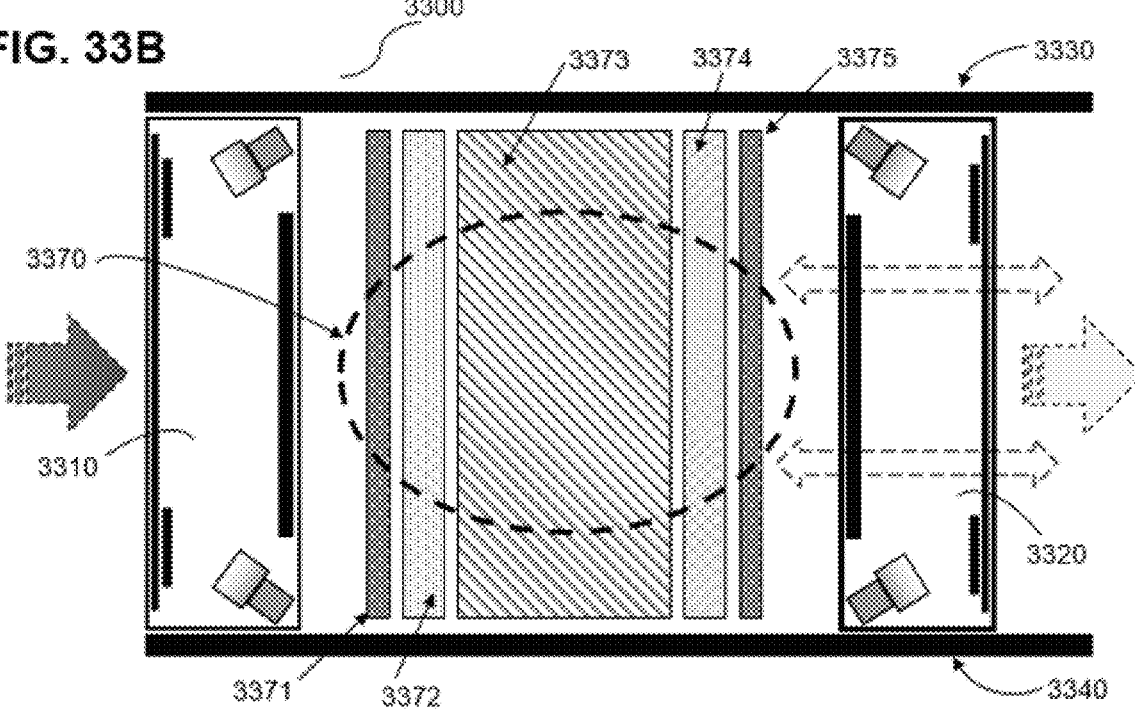

FIGS. 33A-B illustrate a system and method in which an ionizing-radiation beam source with two separated ultra-thin scintillator based multi-camera beam monitors can be used with a patient phantom or material cross-sectional phantom placed between them for patient treatment planning, analysis and quality assurance including 2D measurement of beam scattering, loss of beam quality/sharpness, and beam fluence as the beam penetrates the phantom for both single beam and grid separated multibeam high spatial resolution radiotherapies (RT) such as minibeam-RT and microbeam-RT in accordance to embodiments. The two versions of system 3300 illustrated in FIGS. 33A and 33B are both based on the use of two highly transmissive beam monitors 3310 and 3320 separated by an adjustable air volume/gap as indicated by the two narrow dotted arrows going through the beam monitor 3320 indicating that the beam monitor can be slid back and forth as required on the open frame track/channel structure 3330 and 3340 which also serves to keep the two beam monitors aligned with respect to one another. The space between the two beam monitors is to allow insertion of either a patient specific phantom such as 3350 in FIG. 33A or an adjustable thickness and density phantom 3370 as shown in FIG. 33B that includes one or more material plates that can be of different densities and thicknesses as indicated by plates 3371-3375. In either case, the volume of air between the two beam monitors is minimized by positioning the phantom 3350 or 3370 as close as practical to beam monitor 3310 and then sliding beam monitor 3320 close up to the phantom on the opposite side. The beam of ionizing-radiation, as indicated by the short and wide dotted-dark gray arrow 3380, enters beam monitor 3310 through ultra-thin window 3311 and exits through the scintillator/window module 3312, then passes through the phantom media before entering beam monitor 3320 through the window/scintillator 3322 and exiting through the ultra-thin window 3321 as indicated by the lighter-gray short and wide dotted-arrow 3390. Photons generated by the ionizing-radiation beam 3380 passing through the beam scintillator 3312 are collected and imaged by one or more cameras, such as 3315, viewing the scintillator through a close proximity mirror 3316 at an oblique angle that constitutes a folded optical system located outside of the beam path and with a projection of the camera system optical axis oriented at an angle of incidence of 45°±35° to a surface of the scintillator. The same scintillator and folded optics camera system arrangement is employed for the ionizing-radiation beam as it passes through the exit beam scintillator 3322. The beam monitors themselves can be essentially any of the light-tight enclosure beam monitor embodiments previously described including both single and dual scintillator systems, although for most patient planning, analysis and QA applications the single scintillator embodiments 3310 and 3320 would likely be the most appropriate.

In comparing the machine vision camera captured images of the ionizing-radiation beam generated at the entrance beam monitor 3310 versus at the exit beam monitor 3320 with different phantom media inserted in between the two beam monitors, one can measure in two-dimensions the extent of beam intensity reduction and spatial distortion/smearing including degradation of the beam definition in terms of beam shape/width, sharpness, scattering, intensity profile and fluence. In fact, by inserting a succession of different material plate thicknesses and densities as illustrated by 3370 in FIG. 33B, the progressive degradation of the beam definition and intensity profile can be measured as a function of beam penetration depth through different types of simulated body tissue. This method of analysis in tracking beam degradation through an adjustable plate phantom could prove to be especially useful for patient planning and QA with high spatial resolution ionizing-radiation beam modalities involving both single beams as well as a grid of multiple beams such as employed with minibeam-RT and microbeam-RT.

The range of appropriate material densities for use as the adjustable plate phantom 3370 in FIG. 33B to simulate a patient's body/organs being exposed to an incident ionizing-radiation beam can be realized using a variety of polymers/plastics and even metal plates. The materials used do not have to be optically transparent since the cameras view the scintillators obliquely from the sides. Most fortunately, plastics/polymers are available in a wide range of densities that cover the human body from fat to bones, for example from 0.9 g/cm$^3$ using polypropylene, to 1.8 g/cm$^3$ using PVDF (i.e. polyvinylidene fluoride or Kynar-740). However, a magnesium (Mg) plate has about the same density as PVDF (~1.8 g/cm$^3$) which is close in density to that of the human skull and bones, but with Mg having the benefit of being a metal in the same Periodic Table Group as Ca, with a higher average-Z (i.e. atomic number) than PVDF and a lower-Z than Ca, although a good match to what might be considered the average-Z of the chemical composition of the skull and bones.

In summary, some of the advantages of the novel beam monitoring system technology and embodiments disclosed herein include: (1) a very small monitor thickness in the beam path that combined with its low-Z material and essentially perfect uniformity provide practically negligible interference with the beam and minimal stray radiation in contrast with the existing devices; (2) a large dynamic range or bandwidth of 2D beam fluence/dose measurements that allows for precise beam intensity measurements and dosimetry for low, standard and very high beam rates (a la FLASH); (3) an ultra-fast true 2D beam profile imaging capability with ≤5 μm spatial resolution and ~50 to 100 μs timing resolution which is greatly superior in comparison to existing beam monitors based on ionization chamber arrays and impossible with strip/wire ionization chambers.

As previously disclosed, the beam monitor system 2800 in FIGS. 28A-C includes a camera 2804 mounted in a 4-way-cross open chamber 2815 attached to the 6-way-cross of system 2800. As illustrated in FIGS. 28A-C, the 4-way-cross chamber 2815 is open to the air and capable of actively or passively cooling the camera 2804 in accordance with embodiments. Because the camera chamber is open to the air, it does not need to be in a vacuum chamber enclosure. Embodiments include the camera mounted in any type or shape structure or enclosure, including a plastic or metal box, a modified cylinder, a circular truncated cone, etc. or even a 3D printed plastic enclosure of irregular shape.

For particle beam monitoring applications in a high- to ultra-vacuum environment using any type of vacuum chamber configuration, including the multi-arm crosses shown in FIGS. 9-13 and 27-29, it is beneficial to reduce internal light reflections as much as possible that result in stray photons finding their way into the various light measuring sensor components, such as the cameras, PMTs, etc. The ideal solution is to deposit an ultra-thin black coating (≤2 μm) on the vacuum chamber interior walls, which most often are fabricated using stainless steel. For stainless steel there are at least two types of ultra-thin black coating technologies that are high-vacuum compatible, "black chrome" and "black oxide". For a complex tubular structure like a 6-way-cross, it would be challenging to uniformly coat the insides of the cross using the standard black chrome coating process without introducing additional electrodes inside the cross. On the other hand, the black oxide process is a wet chemical bath process resulting in a uniform coating on all surfaces exposed to the bath. The black oxide is actually magnetite ($Fe_3O_4$) and is chemically formed on the metal surface by chemical reaction with the iron in the stainless steel. The iron black oxide is subject to chemical reaction with air and moisture, but is protected in a vacuum environment. However, to prevent any surface degradation under ambient conditions, the black oxide is typically protected with a very thin layer of oil which is not compatible with vacuum operation. Instead of oil, a very thin layer (≤1 μm) of parylene can be chemically deposited over the iron black oxide. Parylene is considered a very high performance conformal coating and has been approved by NASA for space applications. It has also been shown to be thermally stable under continuous exposure for 10 years at 220° C., so can definitely survive a typical bakeout process at 150-200° C. to eliminate any outgassing of which there would be very little.

The most common pixelated imaging devices and systems are cameras which are based on relatively small (e.g., from ~0.2 cm$^2$ to 10 cm$^2$) CMOS or CCD silicon photosensors. Silicon-based photosensors are most sensitive to visible photons, although their spectral sensitivity typically extends from the near-infrared to the near-ultraviolet. For higher energy ionizing-radiation such as X-ray photons, other types of pixelated sensor systems are used such as flat-panel imagers (FPIs). Most FP's employ an ionizing-radiation detecting conversion medium coupled to a pixelated flat-panel readout backplane of either active-matrix amorphous-silicon (a-Si) thin-film transistors (TFT) or silicon-CMOS. For large-area X-ray FP's (e.g., from ~200 cm$^2$ to 2,000 cm$^2$), a-Si-TFTs are most often used for the pixelated backplane array, although tiled CMOS sensors have also found application in X-ray imaging systems that require faster image processing (i.e., frame rates) than can be achieved with the currently designed a-Si-TFTs. For both types of silicon-based pixelated flat-panel readout backplane array systems, the incident ionizing-radiation is typically converted into electrical signals via the addition of either a direct-conversion or indirect-conversion medium. In other words, the silicon-based pixelated backplane array is transformed into an ionizing-radiation imaging device by adding a radiation detecting conversion media such as a relatively thin photoconductor (i.e., direct-conversion) or a phosphor/scintillator (i.e., indirect-conversion). Of these two types of media, the most common type for most applications is based on indirect conversion primarily via organic or inorganic scintillator materials, although for some specialized applications there are liquid and gaseous scintillators. For direct-conversion, both crystalline and polycrystalline semiconductor materials are most often employed, some examples being: amorphous-selenium (a-Se), cadmium telluride (CdTe), cadmium zinc telluride sometimes referred to as CZT (Cd ZnTe), lead iodide ($PbI_2$), mercuric iodide ($HgI_2$), lead oxide (PbO), thallium bromide (TlBr), and various perovskites with some compositions designed for direct-conversion and other compositions used as scintillators for indirect-conversion. It is noted that for direct-conversion X-ray FPIs, the best materials are relatively high-bandgap (e.g., ≥2 eV) semiconductors that contain elements of high-atomic-number.

In addition to the conventional CMOS or CCD based sensor cameras and flat-panel pixelated imaging systems disclosed above, there are a number of other types of pixelated imaging detectors and devices that can be configured as pixelated imaging systems or cameras. These include various types of multi-pixel photon counters (MPPCs) or pixelated solid state photomultipliers (SSPMs) such as pixelated silicon photomultipliers (SiPMs) which are a high density matrix/array of Geiger-mode-operated avalanche photodiodes (APDs) also called single-photon avalanche photodiodes (SPAD). A relatively new type of pixelated imaging detector/counter is the quanta image sensor (QIS). However, the highest gain (~$10^6$) pixelated imaging detectors are multianode photomultiplier tubes (i.e., pixelated PMTs) such as the ones from Hamamatsu available in either an 8×8 multianode matrix (64 pixels) or a 16×16 multianode matrix format (256 pixels).

Any of the above pixelated imaging detectors can be optically coupled to a suitable imaging lens and with the addition of associated electronics can be used as the "camera" element, in conjunction with the scintillator screen, for the various transmission ionizing-radiation beam monitoring systems described herein. In other words, all of the above imaging detectors could serve the same function as the CMOS or CCD silicon photosensor in a conventional camera. Therefore, when packaged in a light-tight enclosure with appropriate lens mount, lens, supporting electronics and software, the resulting pixelated imaging system would in essence constitute a novel camera system for which a number of embodiments and applications are possible—from medical imaging to non-destructive testing, nuclear physics, high-energy physics, astronomy, etc.

A variety of mostly thin and/or ultra-thin organic scintillators for a number of different transmissive ionizing-radiation beam monitoring system embodiments were disclosed above. However, there are probably more types of inorganic or ceramic based scintillators than organic scintillators, and inorganic scintillators enjoy the advantage of typically being much more light yield efficient (i.e., photons per absorbed MeV) than organic scintillators. Historically, however, inorganic scintillators have not been available as thin scintillators, and certainly not as ultra-thin large-area scintillators, but instead can be considered relatively thin scintillators if having an approximately 1.5 mm or less thickness. The Sigma-Aldrich materials science phosphor and luminescent materials online products pages list more than 300 inorganic phosphor hosts, dopants and products including not only bulk materials such as crystals and powders, but also nanoparticles and about a hundred phosphor dot products. Recently there has been a lot of interest in various types of perovskite inorganic and perovskite hybrid organic-inorganic scintillator materials including double-perovskite scintillator materials. Unfortunately, many inorganic scintillators are hydroscopic which makes them harder to work with when exposed to an ambient environment.

One of the most widely used inorganic scintillators is CsI(Tl), which is only slightly hydroscopic, but even in small sizes of 2 to 4 cm in diagonal the thinnest single crystal polished material available is ~1 mm thick, with larger sizes being considerably thicker. Nevertheless, for large-area X-ray FP's of up to ~60 cm in diagonal, there are several commercially available thin or relatively thin inorganic scintillator screens based on a few scintillator materials, including micro-columnar CsI having vertically-oriented needle structures (either Tl or Na activated), $Gd_2O_2S$ generally known as gadolinium oxysulfide and abbreviated as GOS or Gadox (either Tb or Pr activated), and ZnS (Ag activated). Typically, these scintillators are deposited on a polymer, or glass, or metal substrate (e.g., aluminum, stainless steel, etc.), and incorporate an ultra-thin protective film covering if hydroscopic, such as a polyester, acrylic, or an aromatic polymer (e.g., parylene) of less than 10 μm thickness. The most common such scintillator substrate is a polyester sheet of polyethylene terephthalate (PET) of ~150 to 250 μm thickness. The two most widely used scintillator materials for large-area X-ray FP's are CsI(Tl) or CsI(Na) with phosphor thicknesses from about 0.1 to 0.7 mm, and GOS(Tb) or GOS(Pr) with phosphor thicknesses from about 0.05 to 0.5 mm. It is noted that ZnS(Ag) is also commercially available from at least one vendor in a 0.05 mm phosphor layer thickness on a 250 μm thick polyester substrate.

For X-ray medical radiography including fluoroscopy, the two most popular scintillator screen host materials are CsI and GOS, which are commercially available in sizes up to about 43 cm×43 cm. For security screening and industrial inspection, GOS is available in large sheets up to 1.00 m×1.75 m. Both the GOS and ZnS screens are actually a dispersion of very small phosphor crystals embedded in an organic binder/media (e.g., glue, epoxy, etc.). As a consequence, these types of phosphor layer coatings are sometimes called granular scintillator films. There are a number of other potential applications for these scintillator screens, such as in nuclear and/or high-energy physics for use in ionizing-radiation particle beam tracking, particle beam tuning, spectrometers, hodoscopics, calorimeters, etc. For hodoscopes and calorimeters, a stack of such scintillator screens might be required depending on the type and energy of the incident radiation. This would also be true for calorimeters that might be used for medical applications.

In principle, any of the hundreds of inorganic phosphors can be fabricated in a similar fashion as the above described GOS scintillator screens in which small crystalline particles or nanoparticles are dispersed in an organic matrix (e.g., binder or glue layer) and coated on an appropriate thin substrate, with or without an ultra-thin protective layer. A few such possible scintillator materials (using their abbreviated name designations) activated by Ce include: LSO:Ce, LYSO:Ce, GSO:Ce, YAG:Ce, TAG:Ce, GAGG:Ce, GPS:Ce, etc. It is noted that the GOS based scintillator screens can be used to advantage in a neutron beam monitoring system, as Gd has the highest neutron cross-section of any element on the periodic table. In this regard GSO, GPS and GAGG also contain Gd and could be potential candidate materials for this application. As mentioned previously, boron neutron capture therapy (BNCT) and gadolinium neutron capture therapy (Gd-NCT) are being pursued worldwide for treating some of the most difficult types of cancer tumors by external beam radiation therapy, so use of Gd containing phosphors could prove important for monitoring the incident neutron beam.

The use of shielding materials for neutrons has been previously discussed quite extensively. For X-ray medical radiography, as well as for ionizing-radiation particle beams that generate X-ray photons as they interact with other materials, it is possible to efficiently shield the cameras from such radiation in the light-tight enclosures described herein. For medical diagnostic X-rays, ~0.5 mm of lead or ~0.3 mm of tungsten will absorb/shield ~95-99% of the incident X-ray photons depending upon the X-ray photon energy. For example, in FIG. 8A, FIGS. 14C-D, FIGS. 17A-B, FIGS. 20A-B, and FIGS. 21A-B, a small size lead sheet of this thickness could be placed between each camera and the enclosure wall on the side facing the radiation beam source. Alternatively, the enclosure wall itself on the side facing the radiation beam source could be made from 0.5 mm thick lead.

Embodiments include an ionizing-radiation beamline monitoring system that includes a vacuum chamber structure with vacuum compatible flanges through which an incident ionizing-radiation beam enters the monitoring system.

Embodiments include at least one scintillator within the vacuum chamber structure that can be at least partially translated in the ionizing-radiation beam while oriented at an angle greater than 10 degrees to a normal of the incident ionizing-radiation beam; a machine vision camera coupled to a light-tight structure at atmospheric/ambient pressure that is attached to the vacuum chamber structure by a flange attached to a vacuum-tight viewport window with the camera and lens optical axis oriented at an angle of less than degrees with respect to a normal of the scintillator; and at least one ultraviolet ("UV") illumination source facing the scintillator in the ionizing-radiation beam for monitoring a scintillator stability comprising scintillator radiation damage.

Embodiments further include a wired cable or wireless data interface connection between the machine vision camera and a computer system to process and analyze a train of image data frames streaming in real-time from the machine vision camera. Embodiments further include at least one UV photosensor positioned to monitor the UV illumination source.

In embodiments, the UV illumination source comprises a UV light emitting diode ("LED") with a UV bandpass filter optically coupled in close proximity to each UV-LED and having a maximum spectral transmission in a spectral region of maximum emission from the UV-LED. In embodiments, the vacuum chamber structure comprises a multi-arm cross or other such multi-arm or multi-port chamber.

In embodiments, the scintillator is mounted in a frame and attached to a shaft of a push-pull linear positioner that can be pushed or pulled or nudged through the incident ionizing-radiation beam area from one arm of the cross or chamber either towards or into an opposite arm. In embodiments, the scintillator in its frame is oriented at an angle of 45±35 degrees to the normal of the incident ionizing-radiation beam and concurrently a camera optical axis is oriented at an angle of 45±35 degrees to the normal of the scintillator.

In embodiments, the scintillator comprises a film or sheet of biaxially-oriented polyethylene naphthalate ("BoPEN") falling within a thickness range between 1 μm and 300 μm. In embodiments, the scintillator comprises a sheet of gadolinium oxysulfide ($Gd_2O_2S$) that is typically activated with one or more of a rare earth element such as Tb, Pr, Eu, Ce, etc.

In embodiments, a number of scintillators are mounted in segmented ladder type scintillator holder with each scintillator in its own frame and positioned into the incident ionizing-radiation beam area by means of a push-pull linear positioner. In embodiments, each scintillator frame and the segmented ladder type scintillator holder has an ultra-thin black coating along with possibly some surfaces of the vacuum chamber interior to reduce interior reflections and with the black coating having minimal outgassing.

In embodiments, the camera is located off of one arm or port of the cross or chamber, and a photomultiplier tube ("PMT") or solid state photomultiplier ("SSPM") such as a silicon photomultiplier ("SiPM") is attached via a light-tight structure at atmospheric/ambient pressure to the flange of a second viewport window on the arm or port opposite the camera. In embodiments, a UV blocking and visible transmitting bandpass filter is optically coupled to a camera lens and/or the PMT or SSPM with the bandpass filter having high transmission in a visible spectral emission region of the scintillator.

In embodiments, the camera is replaced by a second PMT or SSPM such that each PMT or SSPM is viewing opposite surfaces of the same scintillator with or without a lens coupled to each PMT or SSPM. In embodiments, a first condensing lens is located in close proximity to the viewport window in the light-tight structure at atmospheric/ambient pressure containing the PMT or SSPM, and a second condensing lens is located on the other side of the same viewport window in the vacuum chamber just below the scintillator frame, with the two condensing lenses separated by the viewport window but facing each other belly-to-belly to capture a relatively large solid angle of light from the scintillator and projecting it onto a light sensitive area of the PMT or SSPM.

In embodiments, a first scintillator in its frame is located in one arm of the cross or chamber and a second scintillator in its frame is located in the opposite arm of the cross or chamber, with each scintillator attached to its own push-pull linear positioner, and wherein the first and second scintillators do not have to be identical either in composition or in thickness.

In embodiments, at least one gate valve is positioned between at least one of the scintillator arms and the flange connected to the main body of the cross or vacuum chamber such that the gate valve can be closed to allow replacement of the scintillator or scintillators without breaking vacuum in the main body of the cross or vacuum chamber or beamline.

In embodiments, the scintillator film in the beam path comprises a small area of a much larger roll-to-roll scintillator feed system in which the scintillator film is wrapped around and stored on a small diameter feeder-spool located inside the vacuum chamber structure and pulled across an incident ionizing-radiation beam axis transit area onto a take-up spool that can be advanced by a stepper-motor rotating a take-up spool spindle to move a new section of scintillator film across the beam axis transit area to replace a previously radiation damaged area as required.

In embodiments, a film of the scintillator is comprised of biaxially-oriented polyethylene naphthalate ("BoPEN"). In embodiments, an entire roll-to-roll scintillator feeder spool and take-up spool system can be mechanically translated into or out of an incident ionizing-radiation beam transit area without breaking vacuum.

Embodiments further perform the monitoring of a beam of ionizing-radiation in a vacuum beamline in real-time. The monitoring includes receiving the ionizing-radiation beam in a scintillator enclosed in a vacuum chamber structure with vacuum compatible flanges through which an incident ionizing-radiation beam enters the vacuum chamber structure, wherein the scintillator can be at least partially translated in the incident ionizing-radiation beam using a push-pull linear positioner while oriented at an angle greater than 10 degrees to a normal of the incident radiation beam, the vacuum chamber structure comprising a machine vision camera attached to the vacuum chamber structure by a flange attached to a vacuum-tight viewport window with the camera and lens at atmospheric/ambient pressure and a camera system optical axis oriented at an angle of less than 80 degrees with respect to a normal of the scintillator; with at least one UV illumination source facing the scintillator for monitoring a scintillator stability comprising scintillator radiation damage. The multitude of emitting photons are created by the ionizing-radiation beam passing through the scintillator, some of which emitted photons are captured by the camera. The monitoring causing a train of image data frames streaming out from the camera to a computer system, wherein the computer system processes and analyzes the image data streaming from the camera in real-time to monitor the beam position, intensity profile and/or shape, beam fluence, and/or a position of single particles.

Many embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. An ionizing-radiation beamline monitoring system comprising:
    a vacuum chamber structure with at least one viewport window;
    at least one scintillator within the vacuum chamber structure attached to a linear positioner;
    a machine vision camera with lens physically coupled to the vacuum chamber structure via the viewport window; and
    a wired cable or wireless data interface connection between the machine vision camera and a computer system to process and analyze a train of image data frames streaming in real-time from the machine vision camera;
    wherein the scintillator can be at least partially translated in an incident ionizing-radiation beam while oriented at an angle greater than 10 degrees to a normal of the incident ionizing-radiation beam;
    wherein the scintillator is mounted in a frame and attached to a shaft of a linear positioner that can be pushed or pulled or nudged through the incident ionizing-radiation beam either manually, or controlled pneumatically, or by a stepper motor, from one location to another location.

2. The ionizing-radiation beamline monitoring system of claim 1, wherein the vacuum chamber structure comprises a multi-arm cross or other such multi-arm or multi-port chamber.

3. The ionizing-radiation beamline monitoring system of claim 1, wherein the scintillator in its frame is oriented at an angle of 45±35 degrees to the normal of the incident ionizing-radiation beam and concurrently a camera optical axis is oriented at an angle of 45±35 degrees to the normal of the scintillator.

4. The ionizing-radiation beamline monitoring system of claim 1, wherein the scintillator comprises a film or sheet of biaxially-oriented polyethylene naphthalate (BoPEN) falling within a thickness range between 1 µm and 300 µm.

5. The ionizing-radiation beamline monitoring system of claim 1, wherein the scintillator comprises a layer of gadolinium oxysulfide (Gd2O2S) crystalline particles that are typically activated with one or more of a rare earth element such as Tb, Pr, Eu, Ce, etc. and dispersed in a host matrix, and coated on a thin substrate.

6. The ionizing-radiation beamline monitoring system of claim 1, wherein a number of scintillators are mounted in a segmented ladder type scintillator holder with each scintillator in its own frame and positioned into the incident ionizing-radiation beam by means of a push-pull linear positioner that can be motor controlled.

7. The ionizing-radiation beamline monitoring system of claim 6, wherein each scintillator frame and the segmented ladder type scintillator holder has an ultra-thin black coating along with possibly some surfaces of the vacuum chamber interior to reduce interior reflections and with the black coating having minimal outgassing.

8. The ionizing-radiation beamline monitoring system of claim 1, wherein the camera is located off of one arm or port of a cross or a chamber, and a photomultiplier tube (PMT) or solid state photomultiplier (SSPM) such as a silicon photomultiplier (SiPM) is attached via a light-tight structure at atmospheric/ambient pressure to a flange of a second viewport window on an arm or port opposite the camera.

9. The ionizing-radiation beamline monitoring system of claim 8, wherein the camera is replaced by a second PMT or SSPM such that each PMT or SSPM is viewing opposite surfaces of the same scintillator with or without a lens coupled to each PMT or SSPM.

10. The ionizing-radiation beamline monitoring system of claim 8, wherein a first condensing lens is located in close proximity to the viewport window in the light-tight structure at atmospheric/ambient pressure containing the PMT or SSPM, and a second condensing lens is located on the other side of the same viewport window in the vacuum chamber just below the scintillator frame, with the two condensing lenses separated by the viewport window but facing each other belly-to-belly to capture a relatively large solid angle of light from the scintillator and projecting it onto a light sensitive area of the PMT or SSPM.

11. The ionizing-radiation beamline monitoring system of claim 1, wherein a first scintillator in its frame is located in one arm of the cross or chamber and a second scintillator in its frame is located in the opposite arm of the cross or chamber, with each scintillator attached to its own push-pull linear positioner, and wherein the first and second scintillators do not have to be identical either in composition or in thickness.

12. The ionizing-radiation beamline monitoring system of claim 11, wherein at least one gate valve is positioned between at least one of the scintillator arms and the flange connected to the main body of the cross or vacuum chamber such that the gate valve can be closed to allow replacement of the scintillator or scintillators without breaking vacuum in the main body of the cross or vacuum chamber or beamline.

13. The ionizing-radiation beamline monitoring system of claim 1, wherein scintillator film in a beam path comprises a small area of a much larger roll-to-roll scintillator feed system in which the scintillator film is wrapped around and stored on a small diameter feeder-spool located inside the vacuum chamber structure and pulled across an incident ionizing-radiation beam axis transit area onto a take-up spool that can be advanced by a stepper-motor rotating a take-up spool spindle to move a new section of scintillator film across the beam axis transit area to replace a previously radiation damaged area as required.

14. The ionizing-radiation beamline monitoring system of claim 13, wherein a film of the scintillator is comprised of biaxially-oriented polyethylene naphthalate (BoPEN).

15. The ionizing-radiation beamline monitoring system of claim 13, wherein an entire roll-to-roll scintillator feeder spool and take-up spool system can be mechanically translated into or out of an incident ionizing-radiation beam transit area without breaking vacuum.

16. The ionizing-radiation beamline monitoring system of claim 1, wherein the machine vision camera is partially shielded from external radiation by extending an optical tube length of the camera system from the beamline and partially compensating for associated light loss by introduction of a relay lens system.

17. A method of monitoring a beam of ionizing-radiation in a vacuum beamline in real-time, the method comprising:
    receiving the ionizing-radiation beam in a scintillator enclosed in a vacuum chamber structure with vacuum compatible flanges through which an incident ionizing-radiation beam enters the vacuum chamber structure, wherein the scintillator can be at least partially translated in the incident ionizing-radiation beam using a push-pull linear positioner while oriented at an angle greater than 10 degrees to a normal of the incident radiation beam, the vacuum chamber structure comprising a machine vision camera attached to the vacuum chamber structure by a flange attached to a vacuum-tight viewport window with the camera and lens at atmospheric/ambient pressure and a camera system optical axis oriented at an angle of less than 80 degrees with respect to a normal of the scintillator;

wherein a multitude of emitting photons are created by the ionizing-radiation beam passing through the scintillator, some of which emitted photons are captured by the camera;

causing a train of image data frames streaming out from the camera to a computer system;

wherein the computer system processes and analyzes the image data streaming from the camera in real-time to monitor the beam position, intensity profile and/or shape, beam fluence, and/or a position of single particles.

* * * * *